(12) United States Patent
Dockter et al.

(10) Patent No.: US 12,382,892 B2
(45) Date of Patent: Aug. 12, 2025

(54) BARLEY WITH INCREASED HYDROLYTIC ENZYME ACTIVITY

(71) Applicant: Carlsberg A/S, Copenhagen (DK)

(72) Inventors: Christoph Dockter, Copenhagen (DK); Pai Rosager Pedas, Copenhagen (DK); Søren Knudsen, Copenhagen (DK); Ole Olsen, Copenhagen (DK); Lucia Marri, Copenhagen (DK); Katarzyna Krucewicz, Copenhagen (DK); Finn Lok, Copenhagen (DK); Toni Wendt, Copenhagen (DK); Massimiliano Carciofi, Copenhagen (DK); Hanne Thomsen, Copenhagen (DK); Magnus Rasmussen, Copenhagen (DK)

(73) Assignee: Carlsberg Breweries A/S, Copenhagen V (DK)

( * ) Notice: Subject to any disclaimer, the term of this patent is extended or adjusted under 35 U.S.C. 154(b) by 308 days.

(21) Appl. No.: 16/958,098

(22) PCT Filed: Dec. 21, 2018

(86) PCT No.: PCT/EP2018/086733
§ 371 (c)(1),
(2) Date: Jun. 25, 2020

(87) PCT Pub. No.: WO2019/129739
PCT Pub. Date: Jul. 4, 2019

(65) Prior Publication Data
US 2021/0395762 A1 Dec. 23, 2021

(30) Foreign Application Priority Data
Dec. 28, 2017 (EP) .................................. 17210964

(51) Int. Cl.
*A01H 6/46* (2018.01)
*A01H 5/10* (2018.01)
*A23L 2/38* (2021.01)
*C07K 14/41* (2006.01)
*C07K 14/415* (2006.01)
*C12C 1/02* (2006.01)
*C12C 1/027* (2006.01)
*C12G 3/02* (2019.01)
*C12G 3/021* (2019.01)
*C12N 9/24* (2006.01)
*C12N 9/32* (2006.01)
*C12N 15/82* (2006.01)

(52) U.S. Cl.
CPC ............ *A01H 6/4624* (2018.05); *A01H 5/10* (2013.01); *A23L 2/382* (2013.01); *C07K 14/415* (2013.01); *C12C 1/027* (2013.01); *C12G 3/021* (2019.02); *C12N 9/2422* (2013.01); *C12N 15/8243* (2013.01); *C12Y 302/01001* (2013.01); *C12C 2200/01* (2013.01)

(58) Field of Classification Search
CPC ...................... C12Y 302/01001; A01H 6/4624
See application file for complete search history.

(56) References Cited

U.S. PATENT DOCUMENTS

| 5,981,729 | A | 11/1999 | Chun et al. |
| 2007/0250961 | A1 | 10/2007 | Blaylock et al. |
| 2014/0205709 | A1 | 7/2014 | Li et al. |

FOREIGN PATENT DOCUMENTS

| AU | 2009321894 A1 | 7/2011 | |
| AU | 2010278678 A1 | 3/2012 | |
| CN | 102291982 A | 12/2011 | |
| CN | 102333440 B | 1/2012 | |
| CN | 103209584 A | 7/2013 | |
| KR | 20160093826 A | 8/2016 | |
| WO | WO-9514099 A2 * | 5/1995 | ......... C12N 15/8222 |
| WO | 0017324 A1 | 3/2000 | |
| WO | 2005080577 A2 | 9/2005 | |
| WO | 2005087934 A2 | 9/2005 | |
| WO | 2007100897 A2 | 9/2007 | |
| WO | 2008132231 A1 | 11/2008 | |
| WO | 2010063288 A2 | 6/2010 | |
| WO | 2010075860 A2 | 7/2010 | |
| WO | 2012103594 A1 | 8/2012 | |
| WO | 2015023639 A2 | 2/2015 | |
| WO | 2018001882 A1 | 1/2018 | |

OTHER PUBLICATIONS

Gubler et al., 1992, Gibberellin-responsive elements in the promoter of a barley high-pI alpha-amylase gene. The Plant Cell, 4(11), 1435-1441. (Year: 1992).*
Zhang et al. ,2022, NCBI protein database, GenBank: KAI5012416. 1, hypothetical protein ZWY2020_024550 [*Hordeum vulgare*], Agricultural College, Yangtze University, Jingmi, Jingzhou, Hubei 434000, China. (Year: 2022).*
Kompella et al., 2017, Introduction of premature stop codons as an evolutionary strategy to rescue signaling network function. ACS Synthetic Biology, 6(3), 446-454. (Year: 2017).*
Krenek et al., 2021, CRISPR/Cas9-induced loss-of-function mutation in the barley mitogen-activated protein kinase 6 gene causes abnormal embryo development leading to severely reduced grain germination and seedling shootless phenotype. Frontiers in Plant Science, 12, 670302. (Year: 2021).*
Raventos et al., 1998, HRT, a novel zinc finger, transcriptional repressor from barley. Journal of Biological Chemistry, 273(36), 23313-23320 (included in IDS filed on Dec. 11, 2020). (Year: 1998).*

(Continued)

*Primary Examiner* — Amjad Abraham
*Assistant Examiner* — Santosh Sharma
(74) *Attorney, Agent, or Firm* — McNeill, PLLC

(57) ABSTRACT

The invention relates to barley plants having a high α-amylase activity. The barley plants of the invention may for example carry a mutation in one or more α-amylase promoters, in the HIRT gene, in the HBL12 gene and/or in the WRKY38 gene. The invention further provides plant products prepared from said barley plants.

11 Claims, 18 Drawing Sheets

Specification includes a Sequence Listing.

(56) References Cited

OTHER PUBLICATIONS

Lawrenson et al.,2015, Induction of targeted, heritable mutations in barley and *Brassica oleracea* using RNA-guided Cas9 nuclease. Genome biology, 16, 1-13. (Year: 2015).*
Kuscu et a., 2017, CRISPR-Stop: gene silencing through base-editing-induced nonsense mutations. Nature methods, 14(7), 710-712. (Year: 2017).*
Bhatty et al., 1996, Production of food malt from hull-less barley. Cereal Chemistry, 73(1), 75-80. (Year: 1996).*
Zhang et al., 2024, Readthrough events in plants reveal plasticity of stop codons. Cell Reports, 43(2). (Year: 2024).*
Agu, R.C., et al., "Malting Performance of Normal Huskless and Acid-Dehusked Barley Samples," The Institute & Guild of Brewing, vol. 108, No. 2, pp. 215-220 (2002).
Bak-Jensen, K., et al., "Spatio-temporal profiling and degradation of alpha-amylase isozymes during barley seed germination," The FEBS Journal, vol. 274, pp. 2552-2565 (2007).
Georg-Kraemer, J.E., et al., "Developmental Expression of Amylases During Barley Malting," Journal of Cereal Science, vol. 33, pp. 279-288 (2001).
O81990_HORVU, Uniprot [online], Nov. 1, 1998, URL: https://www.uniprot.org/uniprotkb/O81990/entry, [retrieved on Apr. 1, 2023].
Kuntz, R., et al., "Time Course for the Development of Enzymes in Barley," Journal of the Institute of Brewing, vol. 113, No. 2, pp. 196-205 (2007).
NCBI: AJ001317.1, published on Nov. 14, 2006, URL: https://www.ncbi.nlm.nih.gov/nuccore/AJ001317.1/ retrieved on Aug. 15, 2023.
Raventos, D., et al., "HRT, a Novel Zinc Finger, Transcriptional Repressor from Barley," The Journal of Biological Chemistry, vol. 273, No. 36, pp. 23313-23320 (1998).
Toffoli, F., et al., "Effects of Pulses of Higher Temperature of the Development of Enzyme Activity During Malting," The Institute & Guild of Brewing, vol. 109, No. 4, pp. 337-341 (2003).
Wijngaard, H.H., et al., "The Effect of Germination Temperature on Malt Quality of Buckwheat," Journal of the American Society of Brewing Chemists, vol. 63, No. 1, pp. 31-36 (2005).
Briggs, Dennis, et al., "Barley characteristics and malting: steeping conditions change according to the maturity of the barley," Malts and Malting, China Light Industry Press, pp. 418-421, May 2005.
Decision on Rejection issued in Chinese Application No. 2018800847442 on Dec. 14, 2023 (8 pages).
English translation of Decision on Rejection issued in Chinese Application No. 2018800847442 on Dec. 14, 2023 (8 pages).
Rasmusson, Donald, et al., "Germination: malting is a process of germination and growth of barley," Barley, China Agriculture Press, p. 545, Mar. 1992.
Chandler et al., "'Overgrowth' mutants in barley and wheat: new alleles and phenotypes of the 'Green Revolution' DELLA gene." J Exp Bot., 64(6), pp. 1603-1613 (2013).
Ellerstrom et al., "Ectopic expression of Effector of Transcription perturbs gibberellin-mediated plant developmental processes." Plant Mol Biol. 59(4), pp. 663-681 (2005).
Green et al., "Grain Development Mutants of Barley", Plant Physiol., 114, pp. 203-212 (1997).
Gubler et al., "Gibberellin-regulated expression of a myb gene in barley aleurone cells: evidence for Myb transactivation of a high-pl alpha-amylase gene promoter.", Plant Cell, 7(11), pp. 1879-1891 (1995).
Hakata et al. "Suppression of a-amylase genes improves quality of rice grain ripened under high temperature." Plant Biotechnol J., 10(9), pp. 1110-1117 (2012).
Harris et al., "Molecular interactions of the y-clade homeodomain-leucine zipper class I transcription factors during the wheat response to water deficit". Plant Mol Biol., 90(4-5), pp. 435-452 (2016).

International Barley Genome Sequencing Consortium, "A physical, genetic and functional sequence assembly of the barley genome." Nature, 491(7426), pp. 711-771 (2012).
Jia et al., "Expression level of a gibberellin 20-oxidase gene is associated with multiple agronomic and quality traits in barley." Theoretical and Applied Genetics, 122(8), pp. 1451-1460 (2011).
Kowalczyk et al., "Gibberellin S—Signal Perception and Transduction", Postepy Biologii Komorki, 27(3), pp. 397-423 (2000).
Lanahan et al., "A gibberellin response complex in cereal alpha-amylase gene promoters." Plant Cell., 4(2), pp. 203-211 (1992).
Mare et al., "Hv-WRKY38: a new transcription factor involved in cold- and drought-response in barley." Plant Mol Biol., 55(3), pp. 399-416 (2004).
Mascher et al., "A chromosome conformation capture ordered sequence of the barley genome.", Nature, 544(7651), pp. 427-433 (2017).
Molina-Cano et al., "A mutant induced in the malting barley cv Triumph with reduced dormancy and ABA response." Theor Appl Genet 98, pp. 347-355 (1999).
Nakata et el., "High Temperature-Induced Expression of Rice_-Amylases in Developing Endosperm Produces Chalky Grains.", Front. Plant Sci. 8:2089 (2017).
Olsson et al., "The homeobox genes ATHB12 and ATHB7 encode potential regulators of growth in response to water deficit in *Arabidopsis*." Plant Mol Biol. 55(5), pp. 663-677 (2004).
Raventos et al., "HRT, a novel zinc finger, transcriptional repressor from barley.", J Biol Chem., 273(36), pp. 23313-23320 (1998).
Re et al., "*Arabidopsis* AtHB7 and AtHB12 evolved divergently to fine tune processes associated with growth and responses to water stress.", BMC Plant Biol., 14:150 (2014).
Rogers et al. "The cis-acting gibberellin response complex in high pl alpha-amylase gene promoters. Requirement of a coupling element for high-level transcription.", Plant Physiol. 105(1), pp. 151-158 (1994).
Rogers et al., "Definition and functional implications of gibberellin and abscisic acid cis-acting hormone response complexes.", Plant Cell., 4(11), pp. 1443-1451 (1992).
Rushton et al., "WRKY transcription factors.", Trends Plant Sci., 15(5), pp. 247-258 (2010).
Schwarz et al., "Preharvest Sprouting in the 2002 Midwestern Barley Crop", Occurrence and Assessment of Methodology. J. Am. Soc. Brew. Chem., 62(4), pp. 147-154 (2004).
Shahpiri et al. "Spatio-temporal appearance of a-amylase and limit dextrinase in barley aleurone layer in response to gibberellic acid, abscisic acid and salicylic acid." J Sci Food Agric., 95(1), pp. 141-147 (2015).
Son et al., "ATHB12, an ABA-inducible homeodomain-leucine zipper (HD-Zip) protein of *Arabidopsis*, negatively regulates the growth of the inflorescence stem by decreasing the expression of a gibberellin 20-oxidase gene.", Plant Cell Physiol., 51(9), pp. 1537-1547 (2010).
Sun et al., "Molecular mechanism of gibberellin signaling in plants." Annu Rev Plant Biol., 55, pp. 197-223 (2004).
Valdes et al., "The homeodomain-leucine zipper (HD-Zip) class I transcription factors ATHB7 and ATHB12 modulate abscisic acid signalling by regulating protein phosphatase 2C and abscisic acid receptor gene activities." Plant molecular biology, 80(4-5), pp. 405-418 (2012).
Woodger et al., "A Mak-like kinase is a repressor of GAMYB in barley aleurone.", Plant J., 33(4), pp. 707-717 (2003).
Zou et al., "Interactions of two transcriptional repressors and two transcriptional activators in modulating gibberellin signaling in aleurone cells.", Plant Physiol., 148(1), 176-186 (2008).
Zhang, X. et al., "Research Progress of alpha-Amylase in Barley," Barley and Cereal Sciences, No. 3, pp. 6-9 (2009).

* cited by examiner

```
                      Modified tandem repeat           W-box
Amy6-4                TAACTGACGGTCGTATTGACCGGTGCCTTCTTATGGAAGGCGAAGGCTGCCTC
(SEQ ID NO: 48)
amy1_1a               TAACTGACGGTCGTATTGACCGGTGCCTTCTTATGGAAGGCGAAGGCTGCCTC
(SEQ ID NO: 49)
amy1_1b               TAACTGACGGTCGTATTGACCGGTGCCTTCTTATGGAAGGCGAAGGCTGCCTC
(SEQ ID NO: 50)
amy1_1c               TAACTGACGGTCGTATTGACCAGTGCCTTCTTATGGAAGGCGAAGGCTGCCTC
(SEQ ID NO: 51)
Amy46                 TAACTGACAGTCGTACTGGCCG-------------------GTGCCTT
(SEQ ID NO: 52)
amy1_2                TAACTGACAGTGGTATTGGCCG-------------------GTGCCTT
(SEQ ID NO: 53)
HENZ-43 amy1_1        TAACTGACGGTCGTATTGATCGGTGCCTTCTTATGGAAGGCGAAGGCTGCCTC
(SEQ ID NO: 96)       *** **** ** *** ** #*                          *****

PYR-box
Amy6-4                CATCTACATCACTTGGGCATTGAATCGCCTTTTGAGCTCACCGTACCGGCCGA
(SEQ ID NO: 54)
amy1_1a               CATCTACATCACTTGGGCATTGAATCGCCTTTTGAGCTCACCGTACCGGCCGA
(SEQ ID NO: 55)
amy1_1b               CATCTACATCACTTGGGCATTGAATCGCCTTTTGAGCTCACCGTACCGGCCGA
(SEQ ID NO: 56)
amy1_1c               CATCTCCATCACTTGGGCATTGAATCGCCTTTTGAGCTCACCGCACCGGCCGA
(SEQ ID NO: 57)
Amy46                 CTTGTCGAAGGCTGGATCCATCAGTCGCCTTTTGAGCTCACCGCACCGGCCGA
(SEQ ID NO: 58)
amy1_2                CTCATCGAAGCCGGTGCTCATCATTCGCCTTTTGAGCTCACCGCACCGGCCGA
(SEQ ID NO: 59)
HENZ-43 amy1_1        CATCTACATCACTTGGGCATTGAATCGCCTTTTGAGCTCACCGTACCGGCCGA
(SEQ ID NO: 97)       *  *  *   *              * * *******************  ***

GARE-box       AMY-box
Amy6-4                TAACAAACTCCGGCCGACATATCCACTGG
(SEQ ID NO: 60)
amy1_1a               TAACAAACTCCGGCCGACATATCCACTGG
(SEQ ID NO: 61)
amy1_1b               TAACAAACTCCGGCCGACATATCCACTGG
(SEQ ID NO: 62)
amy1_1c               TAACAAACTCCGGCCAACATATCCACTGG
(SEQ ID NO: 63)
Amy46                 TAACAAACTCCGGCCGACATATCCATCGA
(SEQ ID NO: 64)
amy1_2                TAACAAACTCCGGCCGACATATCCATCGA
(SEQ ID NO: 65)
HENZ-43 amy1_1        TAACAAACTCCGGCCGACATATCCACTGG
(SEQ ID NO: 98)       ************** ********* *
```

Fig. 11A

```
                            Tandem repeat W-box
amy2_1          GGAATTTGTGCCGGCCCGGATTGACTTGACCATCATCT------GTTG
(SEQ ID NO: 66)
amy2_2          GGAGGCTGTGCCAACCCAGCTTGACTTGACCATCACCAG-----TTAC
(SEQ ID NO: 67)
amy2_3          GGAACTTGTGCCACCCCGGATTGACTTGACCGTCATCGGCTCCGGATG
(SEQ ID NO: 68) ***    ******   *** * ***********  ***  *

PYR-box    GARE-box    AMY-box
amy2_1          CACCTTTTCTCGTAACAGAGTCTGGTATCCATGCAG
(SEQ ID NO: 69)
amy2_2          TCCATTTTCCATAACAGAGGCCGGTACCCATGCAT
(SEQ ID NO: 70)
amy2_3          CACCTTTTATCGTAACAGAGTCCGGTATCCATGCAG
(SEQ ID NO: 71) * ****  * ******* * ****  *******
```

Fig. 11B

A)
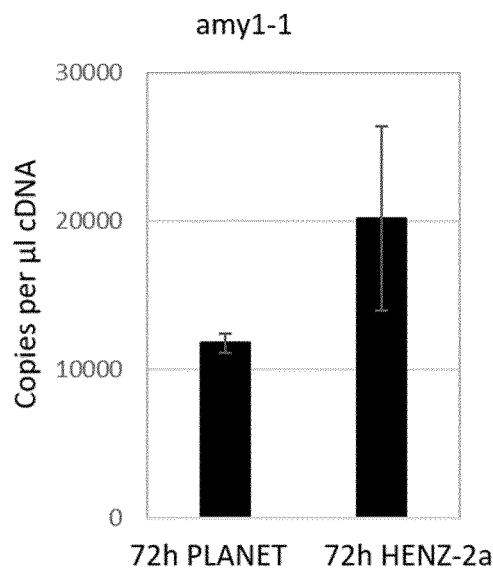
B)
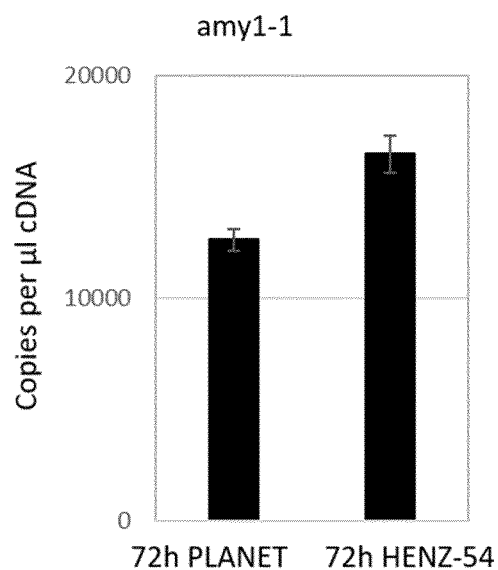
C)
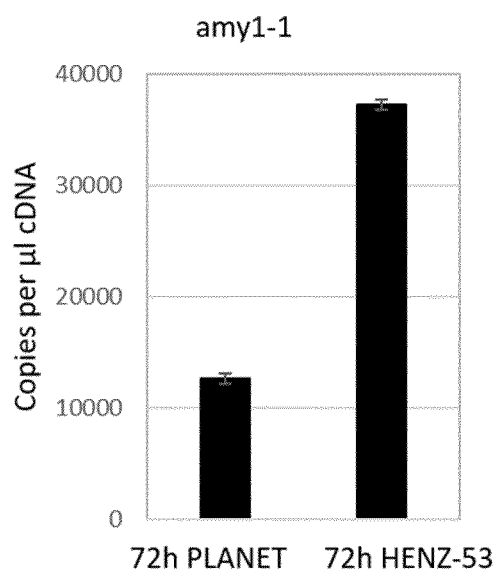
Fig. 17

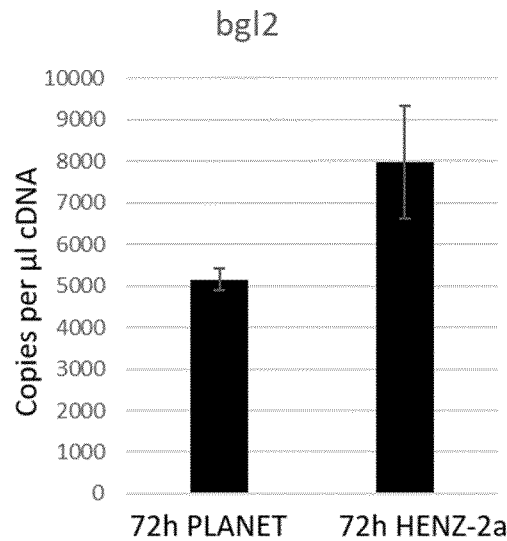
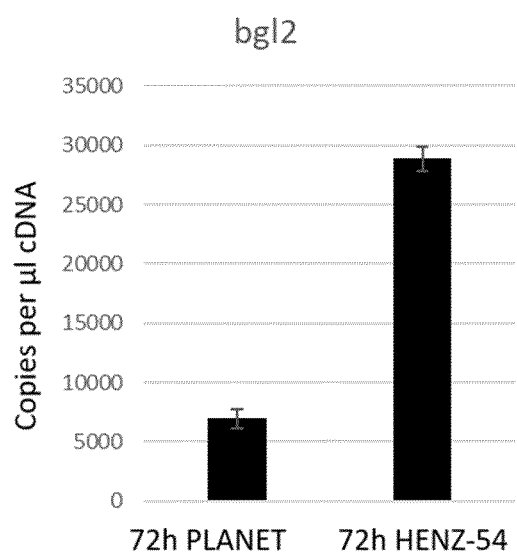
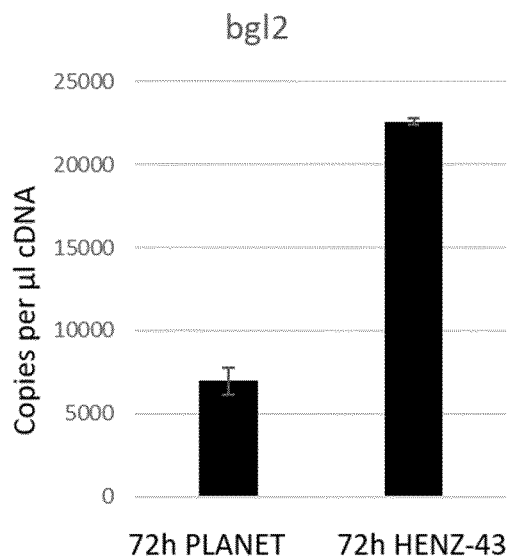
Fig. 20

SEQUENCE LISTING

```
<160> NUMBER OF SEQ ID NOS: 99

<210> SEQ ID NO 1
<211> LENGTH: 1644
<212> TYPE: DNA
<213> ORGANISM: Hordeum vulgare

<400> SEQUENCE: 1
atgcctgcgg tcgccgctgc cagattgaag cgggaggact gcccccgcac caaacacgat      60
tccctcttct ccccatggaa ggttcttgtc gggccgtcgg actgggagga ccactccgcc     120
ggcaaggagg gggtccagag gtatcacaca cgcaacctcc cggacaactt ccctggcctc     180
tacgagctgg gcgttgcaag gccttcctat gatggtgtca gggctcgcag aaatcgatca     240
gttgtcgtcg tggtggtata cctcgggcag gccgataatg tcagggcgag gctccagcag     300
tacgggcgga cagggtcaca cctggacacc gggaatccgt tggctgctgt ctgtaaagct     360
gagatgaacg cgctcacggc aggacctgga ttgttcaggg aagtcttctc cagaggctac     420
tctatgatgt ttcgatgtgc gctgatgggt tccaaaaagg cagctgagaa gactgaaggt     480
cagctactgg gagtatttga ttatgcatgg aataaactgc agaatggtgc gtgtcgtcgc     540
```

```
gaagaaatac tgctcaagtt agaacaggga agcaatagat tatctttgct tagcagagtc    600
cggcacttaa aacagagggt gtttggagag aaagcaggta taaagattaa cagcagtggg    660
tctgttgaga tttcatctag cagtatgaaa aatatgcttc caagagtccg tacgtttgtc    720
ggcttcaggc ctcgtttggt taactctggc gacgatttaa acgaggcaag tgatattcac    780
cgaaaatgca cacctcaggc caatactgct ggtaaacaag cacatagaag gtctgaagga    840
tacaaggtga aaaagatcga tgttattaaa cggcgaactg caccgataag agaagccgaa    900
gctgtttgtg gagtaatgct agaagatggt tcttcttgtt tggaggatcc aatggaagga    960
aggaagaggt gtgagttgca caaggtagag agagtcagag tggcatacag tcgcaaagta   1020
tcctcttcta gctccacttg ccaagttgct attccaactg ttgaatccat acctcaacaa   1080
actgctaatc caagcaaacg agatcaagcc tggcaaacca gtgcagacca atccaaaaat   1140
ctgtccacaa atgcaaagga gccatcttgg caaaggaaca gcttcaaagc aaatgagatg   1200
aaaatcggag aagctcctac agaagatgaa gcatatggaa cctcccatgc agaatctcag   1260
ttccacgaag atgagccttg tggaaggaag tggtttgagc ggctcaaagc acagaaatca   1320
gccaacgcac catcgtcgag aggccaagga tgtcagccaa gagaagcaaa caacgacgca   1380
tcagccttat gtggagtagt gacagataat ggatactgca aactggaacc ggtgatagga   1440
agggaaagat gcgaggagca cagaggaatt gaggtcactg gtgcgtcatc ggcaccatgt   1500
tccggaaggt cggtattgcc atctgtctgt ggagctcggg catccgatgg ttcaccttgc   1560
aagaatcagc caatcgcaag gaggaagaga tgtgcgttgc acaaaggtca agagcgtgc   1620 tgcgcctccg cgccatcagt caaa                                         1644

<210> SEQ ID NO 2
<211> LENGTH: 548
<212> TYPE: PRT
<213> ORGANISM: Hordeum vulgare

<400> SEQUENCE: 2

Met Pro Ala Val Ala Ala Arg Leu Lys Arg Glu Asp Cys Pro Arg
1               5                   10                  15

Thr Lys His Asp Ser Leu Phe Ser Pro Trp Lys Val Leu Val Gly Pro
            20                  25                  30

Ser Asp Trp Glu Asp His Ser Ala Gly Lys Glu Gly Val Gln Arg Tyr
        35                  40                  45

His Thr Arg Asn Leu Pro Asp Asn Phe Pro Gly Leu Tyr Glu Leu Gly
    50                  55                  60

Val Ala Arg Pro Ser Tyr Asp Gly Val Arg Ala Arg Arg Asn Arg Ser
65                  70                  75                  80

Val Val Val Val Val Tyr Leu Gly Gln Ala Asp Asn Val Arg Ala
                85                  90                  95

Arg Leu Gln Gln Tyr Gly Arg Thr Gly Ser His Leu Asp Thr Gly Asn
            100                 105                 110

Pro Leu Ala Ala Val Cys Lys Ala Glu Met Asn Ala Leu Thr Ala Gly
        115                 120                 125

Pro Gly Leu Phe Arg Glu Val Phe Ser Arg Gly Tyr Ser Met Met Phe
    130                 135                 140

Arg Cys Ala Leu Met Gly Ser Lys Lys Ala Ala Glu Lys Thr Glu Gly
145                 150                 155                 160

Gln Leu Leu Gly Val Phe Asp Tyr Ala Trp Asn Lys Leu Gln Asn Gly
                165                 170                 175
```

Ala Cys Arg Arg Glu Glu Ile Leu Leu Lys Leu Glu Gln Gly Ser Asn
            180                 185                 190

Arg Leu Ser Leu Leu Ser Arg Val Arg His Leu Lys Gln Arg Val Phe
            195                 200                 205

Gly Glu Lys Ala Gly Ile Lys Ile Asn Ser Ser Gly Ser Val Glu Ile
            210                 215                 220

Ser Ser Ser Ser Met Lys Asn Met Leu Pro Arg Val Arg Thr Phe Val
225                 230                 235                 240

Gly Phe Arg Pro Arg Leu Val Asn Ser Gly Asp Asp Leu Asn Glu Ala
            245                 250                 255

Ser Asp Ile His Arg Lys Cys Thr Pro Gln Ala Asn Thr Ala Gly Lys
            260                 265                 270

Gln Ala His Arg Arg Ser Glu Gly Tyr Lys Val Lys Lys Ile Asp Val
            275                 280                 285

Ile Lys Arg Arg Thr Ala Pro Ile Arg Glu Ala Glu Ala Val Cys Gly
            290                 295                 300

Val Met Leu Glu Asp Gly Ser Ser Cys Leu Glu Asp Pro Met Glu Gly
305                 310                 315                 320

Arg Lys Arg Cys Glu Leu His Lys Gly Arg Arg Val Arg Val Ala Tyr
            325                 330                 335

Ser Arg Lys Val Ser Ser Ser Ser Thr Cys Gln Val Ala Ile Pro
            340                 345                 350

Thr Val Glu Ser Ile Pro Gln Gln Thr Ala Asn Pro Ser Lys Arg Asp
            355                 360                 365

Gln Ala Trp Gln Thr Ser Ala Asp Gln Ser Lys Asn Leu Ser Thr Asn
370                 375                 380

Ala Lys Glu Pro Ser Trp Gln Arg Asn Ser Phe Lys Ala Asn Glu Met
385                 390                 395                 400

Lys Ile Gly Glu Ala Pro Thr Glu Asp Glu Ala Tyr Gly Thr Ser His
            405                 410                 415

Ala Glu Ser Gln Phe His Glu Asp Glu Pro Cys Gly Arg Lys Trp Phe
            420                 425                 430

Glu Arg Leu Lys Ala Gln Lys Ser Ala Asn Ala Pro Ser Ser Arg Gly
            435                 440                 445

Gln Gly Cys Gln Pro Arg Glu Ala Asn Asn Asp Ala Ser Ala Leu Cys
450                 455                 460

Gly Val Val Thr Asp Asn Gly Tyr Cys Lys Leu Glu Pro Val Ile Gly
465                 470                 475                 480

Arg Glu Arg Cys Glu Glu His Arg Gly Ile Glu Val Thr Gly Ala Ser
            485                 490                 495

Ser Ala Pro Cys Ser Gly Arg Ser Val Leu Pro Ser Val Cys Gly Ala
            500                 505                 510

Arg Ala Ser Asp Gly Ser Pro Cys Lys Asn Gln Pro Ile Ala Arg Arg
            515                 520                 525

Lys Arg Cys Ala Leu His Lys Gly Gln Arg Ala Cys Cys Ala Ser Ala
            530                 535                 540

Pro Ser Val Lys
545

<210> SEQ ID NO 3
<211> LENGTH: 1647
<212> TYPE: DNA
<213> ORGANISM: Artificial sequence
<220> FEATURE:
<223> OTHER INFORMATION: Coding sequence of the HvHRT gene of barley mutant HENZ-2

<400> SEQUENCE: 3

| | | | | | |
|---|---|---|---|---|---|
| atgcctgcgg | tcgccgctgc | cagattgaag | cgggaggact | gccccgcac | caaacacgat | 60 |
| tccctcttct | ccccatggaa | ggttcttgtc | gggccgtcgg | actgggagga | ccactccgcc | 120 |
| ggcaaggagg | gggtccagag | gtatcacaca | cgcaacctcc | cggacaactt | ccctggcctc | 180 |
| tacgagctgg | gcgttgcaag | gccttcctat | gatggtgtca | gggctcgcag | aaatcgatca | 240 |
| gttgtcgtcg | tggtggtata | cctcgggcag | gccgataatg | tcagggcgag | gctccagcag | 300 |
| tacgggcgga | cagggtcaca | cctggacacc | gggaatccgt | tggctgctgt | ctgtaaagct | 360 |
| gagatgaacg | cgctcacggc | aggacctgga | ttgttcaggg | aagtcttctc | cagaggctac | 420 |
| tctatgatgt | ttcgatgtgc | gctgatgggt | tccaaaaagg | cagctgagaa | gactgaaggt | 480 |
| cagctactgg | gagtatttga | ttatgcatgg | aataaactgc | agaatggtgc | gtgtcgtcgc | 540 |
| gaagaaatac | tgctcaagtt | agaacaggga | agcaatagat | tatctttgct | tagcagagtc | 600 |
| cggcacttaa | aacagagggt | gtttggagag | aaagcaggta | taaagattaa | cagcagtggg | 660 |
| tctgttgaga | tttcatctag | cagtatgaaa | aatatgcttc | caagagtccg | tacgtttgtc | 720 |
| ggcttcaggc | ctcgtttggt | taactctggc | gacgatttaa | acgaggcaag | tgatattcac | 780 |
| cgaaaatgca | cacctcaggc | caatactgct | ggtaaacaag | cacatagaag | gtctgaagga | 840 |
| tacaaggtga | aaaagatcga | tgttattaaa | cggcgaactg | caccgataag | agaagccgaa | 900 |
| gctgtttgtg | gagtaatgct | agaagatggt | tcttcttgtt | tggaggatcc | aatggaagga | 960 |
| aggaagaggt | gtgagttgca | caaaggtaga | agagtcagag | tggcatacag | tcgcaaagta | 1020 |
| tcctcttcta | gctccacttg | ccaagttgct | attccaactg | ttgaatccat | acctcaacaa | 1080 |
| actgctaatc | aagcaaacg | agatcaagcc | tggcaaacca | gtgcagacca | atccaaaaat | 1140 |
| ctgtccacaa | atgcaaagga | gccatcttgg | caaaggaaca | gcttcaaagc | aaatgagatg | 1200 |
| aaaatcggag | aagctcctac | agaagatgaa | gcatatggaa | cctcccatgc | agaatctcag | 1260 |
| ttccacgaag | atgagccttg | tggaaggaag | tgatttgagc | ggctcaaagc | acagaaatca | 1320 |
| gccaacgcac | catcgtcgag | aggccaagga | tgtcagccaa | gagaagcaaa | caacgacgca | 1380 |
| tcagccttat | gtggagtagt | gacagataat | ggatactgca | aactggaacc | ggtgatagga | 1440 |
| agggaaagat | gcgaggagca | cagaggaatt | gaggtcactg | gtgcgtcatc | ggcaccatgt | 1500 |
| tccggaaggt | cggtattgcc | atctgtctgt | ggagctcggg | catccgatgg | ttcaccttgc | 1560 |
| aagaatcagc | caatcgcaag | gaggaagaga | tgtgcgttgc | acaaaggtca | aagagcgtgc | 1620 |
| tgcgcctccg | cgccatcagt | caaataa | | | | 1647 |

<210> SEQ ID NO 4
<211> LENGTH: 430
<212> TYPE: PRT
<213> ORGANISM: Artificial sequence
<220> FEATURE:
<223> OTHER INFORMATION: Sequence of mutant HvHRT of barley mutant HENZ-2

<400> SEQUENCE: 4

Met Pro Ala Val Ala Ala Arg Leu Lys Arg Glu Asp Cys Pro Arg
1               5                   10                  15

Thr Lys His Asp Ser Leu Phe Ser Pro Trp Lys Val Leu Val Gly Pro
                20                  25                  30

Ser Asp Trp Glu Asp His Ser Ala Gly Lys Glu Gly Val Gln Arg Tyr
            35                  40                  45

His Thr Arg Asn Leu Pro Asp Asn Phe Pro Gly Leu Tyr Glu Leu Gly
            50                  55                  60

Val Ala Arg Pro Ser Tyr Asp Gly Val Arg Ala Arg Arg Asn Arg Ser
 65                  70                  75                  80

Val Val Val Val Val Tyr Leu Gly Gln Ala Asp Asn Val Arg Ala
                85                  90                  95

Arg Leu Gln Gln Tyr Gly Arg Thr Gly Ser His Leu Asp Thr Gly Asn
            100                 105                 110

Pro Leu Ala Ala Val Cys Lys Ala Glu Met Asn Ala Leu Thr Ala Gly
            115                 120                 125

Pro Gly Leu Phe Arg Glu Val Phe Ser Arg Gly Tyr Ser Met Met Phe
130                 135                 140

Arg Cys Ala Leu Met Gly Ser Lys Lys Ala Ala Glu Lys Thr Glu Gly
145                 150                 155                 160

Gln Leu Leu Gly Val Phe Asp Tyr Ala Trp Asn Lys Leu Gln Asn Gly
            165                 170                 175

Ala Cys Arg Arg Glu Glu Ile Leu Leu Lys Leu Glu Gln Gly Ser Asn
            180                 185                 190

Arg Leu Ser Leu Ser Arg Val Arg His Leu Lys Gln Arg Val Phe
            195                 200                 205

Gly Glu Lys Ala Gly Ile Lys Ile Asn Ser Ser Gly Ser Val Glu Ile
            210                 215                 220

Ser Ser Ser Ser Met Lys Asn Met Leu Pro Arg Val Arg Thr Phe Val
225                 230                 235                 240

Gly Phe Arg Pro Arg Leu Val Asn Ser Gly Asp Asp Leu Asn Glu Ala
                245                 250                 255

Ser Asp Ile His Arg Lys Cys Thr Pro Gln Ala Asn Thr Ala Gly Lys
            260                 265                 270

Gln Ala His Arg Arg Ser Glu Gly Tyr Lys Val Lys Lys Ile Asp Val
            275                 280                 285

Ile Lys Arg Arg Thr Ala Pro Ile Arg Glu Ala Glu Ala Val Cys Gly
            290                 295                 300

Val Met Leu Glu Asp Gly Ser Ser Cys Leu Glu Asp Pro Met Glu Gly
305                 310                 315                 320

Arg Lys Arg Cys Glu Leu His Lys Gly Arg Arg Val Arg Val Ala Tyr
                325                 330                 335

Ser Arg Lys Val Ser Ser Ser Ser Thr Cys Gln Val Ala Ile Pro
            340                 345                 350

Thr Val Glu Ser Ile Pro Gln Gln Thr Ala Asn Pro Ser Lys Arg Asp
            355                 360                 365

Gln Ala Trp Gln Thr Ser Ala Asp Gln Ser Lys Asn Leu Ser Thr Asn
            370                 375                 380

Ala Lys Glu Pro Ser Trp Gln Arg Asn Ser Phe Lys Ala Asn Glu Met
385                 390                 395                 400

Lys Ile Gly Glu Ala Pro Thr Glu Asp Glu Ala Tyr Gly Thr Ser His
                405                 410                 415

Ala Glu Ser Gln Phe His Glu Asp Glu Pro Cys Gly Arg Lys
            420                 425                 430

<210> SEQ ID NO 5
<211> LENGTH: 753
<212> TYPE: DNA
<213> ORGANISM: Hordeum vulgare

<400> SEQUENCE: 5

```
atggagcagg gggaggagga cggggactgg atgatggagc cggcgtcggg gaagaagggc      60
ggggtgatga tcgacaggaa gaagcgcttc agcgaggagc agatcaagtc gctcgagtcc     120
atgttcgcca cgcagaccaa gctggagccc cgccagaagc tgcagctggc ccggagctc      180
ggcctgcagc cgcgccaggt cgccatctgg ttccagaaca agcgcgcgcg ctggaagtcc     240
aagcagctcg agcgccagta cgccgcgctc cgggacgact acgacgccct cctctccagc     300
tacgaccagc tcaagaagga caagcaagcg ctcgtcaacc agctggagaa gctagcagag     360
atgctgcggg agccgggcgg ggccaagtgc ggagataatg ccggcgctgc tgacagggac     420
aacatgcgcc tggccgtggc cggcatgagc atgaaggacg agttcgcgga cgctgccggg     480
gccagcaagc tctactcggc gtctgccgag ggctgcggcg gcagcggcaa gctctccctc     540
ttcggcgagg aggatgacga cgcgggcctc ttcctccggc cctcgctgca gctgccaacc     600
gcgcacgacg gcggcttcac ggcgtcgggg ccggccgagt accagcagca gtcgccgtcg     660
tcgttcccgt ccactcgag ctggccgtcg tccgcgacgg agcagacctg cagcagctcc     720
caatggtggg aattcgagtc cccgagcgag taa                                  753
```

<210> SEQ ID NO 6
<211> LENGTH: 250
<212> TYPE: PRT
<213> ORGANISM: Hordeum vulgare

<400> SEQUENCE: 6

```
Met Glu Gln Gly Glu Glu Asp Gly Asp Trp Met Met Glu Pro Ala Ser
1               5                   10                  15

Gly Lys Lys Gly Gly Val Met Ile Asp Arg Lys Lys Arg Phe Ser Glu
            20                  25                  30

Glu Gln Ile Lys Ser Leu Glu Ser Met Phe Ala Thr Gln Thr Lys Leu
        35                  40                  45

Glu Pro Arg Gln Lys Leu Gln Leu Ala Arg Glu Leu Gly Leu Gln Pro
    50                  55                  60

Arg Gln Val Ala Ile Trp Phe Gln Asn Lys Arg Ala Arg Trp Lys Ser
65                  70                  75                  80

Lys Gln Leu Glu Arg Gln Tyr Ala Ala Leu Arg Asp Asp Tyr Asp Ala
                85                  90                  95

Leu Leu Ser Ser Tyr Asp Gln Leu Lys Lys Asp Lys Gln Ala Leu Val
            100                 105                 110

Asn Gln Leu Glu Lys Leu Ala Glu Met Leu Arg Glu Pro Gly Gly Ala
        115                 120                 125

Lys Cys Gly Asp Asn Ala Gly Ala Ala Asp Arg Asp Asn Met Arg Leu
    130                 135                 140

Ala Val Ala Gly Met Ser Met Lys Asp Glu Phe Ala Asp Ala Ala Gly
145                 150                 155                 160

Ala Ser Lys Leu Tyr Ser Ala Ser Ala Glu Gly Cys Gly Gly Ser Gly
                165                 170                 175

Lys Leu Ser Leu Phe Gly Glu Glu Asp Asp Asp Ala Gly Leu Phe Leu
            180                 185                 190

Arg Pro Ser Leu Gln Leu Pro Thr Ala His Asp Gly Gly Phe Thr Ala
        195                 200                 205

Ser Gly Pro Ala Glu Tyr Gln Gln Gln Ser Pro Ser Ser Phe Pro Phe
    210                 215                 220

His Ser Ser Trp Pro Ser Ser Ala Thr Glu Gln Thr Cys Ser Ser Ser
```

Gln Trp Trp Glu Phe Glu Ser Pro Ser Glu
            245                 250

<210> SEQ ID NO 7
<211> LENGTH: 1546
<212> TYPE: DNA
<213> ORGANISM: Hordeum vulgare

<400> SEQUENCE: 7

```
gagacgggag acccggctac gcatgcacgc caccgcgctc cattggccgc cccgttgcca      60
tcaccgcgcc catcgctcca tcccccgatt aaactactcc atatcgctag taagcagaag    120
cagaatcgat ccatcacacc aagctagcta gcctcctagc tcgctcgctc gcccgcacac    180
ccgcgatcca ttctgcttct tccccttcct tcccactccg gatcaggtgc atgaccaccg    240
gcgagaccta gctaggtagg tagggaggga gggagggatg gagcaggggg aggaggacgg    300
ggactggatg atggagccgg cgtcggggaa gaagggcggg gtgatgatcg acaggaagaa    360
gcgcttcagc gaggagcaga tcaagtcgct agagtccatg ttcgccacgc agaccaagct    420
ggagccccgc cagaagctgc agctggcccg ggagctcggc ctgcagccgc gccaggtcgc    480
catctggttc cagaacaagc gcgcgcgctg gaagtccaag cagctcgagc gccagtacgc    540
cgcgcttcgg gacgactacg acgccctcct ctccagctac gaccagctca agaaggacaa    600
gcaagcgctc gtcaaccagg tatatactcc tatgtctgtc tgtctgtgct acgtaccgtg    660
tgtttctccg tgctctccgc tcggtggcgt ggagctcgtg gtgcctctgg ctaatgcatg    720
gtcgacgggt ttcttgcctt gcgtgtccgt gcagctggag aagctagcag agatgctgcg    780
ggagccgggc ggggccaagt gcggagataa tgccggcgct gctgacaggg acgacgtgcg    840
cctggccgtg gccggcatga gcatgaagga cgagttcgcg gacgctgccg gggccagcaa    900
gctctactcg cgctctgccg agggctgcgg cggcagcggc aagctctccc tcttcggcga    960
ggacgatgac gacgcgggcc tcttcctccg gccctcgctg cagctgccaa ccgcgcacga   1020
cggcggcttc acggcgtcgg ggccggccga gtaccagcag cagtcgccgt cgtcgttccc   1080
gttccactcg agctggccgt cgtccgcgac ggagcagacc tgcagcagct cccaatggtg   1140
ggaattcgag tccccgagcg agtaagtaga gccatcggtc aagcaccatg caaggaatcg   1200
ccgacgtgat cgaccatgca acagatcagt gttcctaaca cagagcacta tactgccgat   1260
cgaatccgtg gagaagacga cggcgcgatc gatcatatgc aaccgaagat ggtggtgtca   1320
agtgtgtaca tagctcgaaa cccaggtctg tccagtccag tacgtccagg cagcctcttc   1380
cttctcaatc agcagtcagc acgccatttt tcttcaccct cttcctcttt aagaatcact   1440
tgctcttgtc aattacctgc cacaccgtgt aatccacagg gaaactagtc acaaaaccaa   1500
attatagaga ccgatcttca gatgcaagtg catgcaacta tttagc                  1546
```

<210> SEQ ID NO 8
<211> LENGTH: 753
<212> TYPE: DNA
<213> ORGANISM: Artificial sequence
<220> FEATURE:
<223> OTHER INFORMATION: Coding sequence of the mutant HvHBL12 gene of
      barley mutant HENZ-10

<400> SEQUENCE: 8

```
atggagcagg ggaggaggga cggggactgg atgatggagc cggcgtcggg gaagaagggc      60
ggggtgatga tcgacaggaa gaagcgcttc agcgaggagc agatcaagtc gctcgagtcc    120
```

```
atgttcgcca cgcagaccaa gctggagccc cgccagaagc tgcagctggc ccgggagctc    180
ggcctgcagc cgcgccaggt cgccatctgg ttccagaaca agcgcgcgcg ctggaagtcc    240
aagcagctcg agcgccagta cgccgcgctc cgggacgact acgacgccct cctctccagc    300
tacgaccagc tcaagaagga caagcaagcg ctcgtcaacc agctggagaa gctagcagag    360
atgctgcggg agccgggcgg ggccaagtgc ggagataatg ccggcgctgc tgacagggac    420
aacatgcgct ggccgtggcc cggcatgagc atgaaggacg agttcgcgga cgctgccggg    480
gccagcaagc tctactcggc gtctgccgag ggctgcggcg gcagcggcaa gctctccctc    540
ttcggcgagg aggatgacga cgcggggcctc ttcctccggc cctcgctgca gctgccaacc    600
gcgcacgacg gcggcttcac ggcgtcgggg ccggccgagt accagcagca gtcgccgtcg    660
tcgttcccgt ccactcgag ctgaccgtcg tccgcgacgg agcagacctg cagcagctcc    720
caatggtggg aattcgagtc cccgagcgag taa                                 753

<210> SEQ ID NO 9
<211> LENGTH: 227
<212> TYPE: PRT
<213> ORGANISM: Artificial sequence
<220> FEATURE:
<223> OTHER INFORMATION: Coding sequence of the mutant HvHBL12 gene of
      barley mutant HENZ-10

<400> SEQUENCE: 9

Met Glu Gln Gly Glu Glu Asp Gly Asp Trp Met Met Glu Pro Ala Ser
1               5                   10                  15

Gly Lys Lys Gly Gly Val Met Ile Asp Arg Lys Lys Arg Phe Ser Glu
                20                  25                  30

Glu Gln Ile Lys Ser Leu Glu Ser Met Phe Ala Thr Gln Thr Lys Leu
            35                  40                  45

Glu Pro Arg Gln Lys Leu Gln Leu Ala Arg Glu Leu Gly Leu Gln Pro
        50                  55                  60

Arg Gln Val Ala Ile Trp Phe Gln Asn Lys Arg Ala Arg Trp Lys Ser
65                  70                  75                  80

Lys Gln Leu Glu Arg Gln Tyr Ala Ala Leu Arg Asp Asp Tyr Asp Ala
                85                  90                  95

Leu Leu Ser Ser Tyr Asp Gln Leu Lys Lys Asp Lys Gln Ala Leu Val
            100                 105                 110

Asn Gln Leu Glu Lys Leu Ala Glu Met Leu Arg Glu Pro Gly Gly Ala
        115                 120                 125

Lys Cys Gly Asp Asn Ala Gly Ala Ala Asp Arg Asp Asn Met Arg Leu
130                 135                 140

Ala Val Ala Gly Met Ser Met Lys Asp Glu Phe Ala Asp Ala Ala Gly
145                 150                 155                 160

Ala Ser Lys Leu Tyr Ser Ala Ser Ala Glu Gly Cys Gly Gly Ser Gly
                165                 170                 175

Lys Leu Ser Leu Phe Gly Glu Glu Asp Asp Asp Ala Gly Leu Phe Leu
            180                 185                 190

Arg Pro Ser Leu Gln Leu Pro Thr Ala His Asp Gly Gly Phe Thr Ala
        195                 200                 205

Ser Gly Pro Ala Glu Tyr Gln Gln Gln Ser Pro Ser Ser Phe Pro Phe
210                 215                 220

His Ser Ser
225
```

<210> SEQ ID NO 10
<211> LENGTH: 1062
<212> TYPE: DNA
<213> ORGANISM: Hordeum vulgare

<400> SEQUENCE: 10

```
atggatccat ggatgggcag ccagccatcc ctgagcctcg acctgcacgt cggcctaccg      60
ccgatggggc acccgcacca ccaccagagc aataccagg cgccgccgat gatcgcgctg      120
gccaagccca agatcctcgt ggaggagaac ttcatgccac tcaagaagga ccctgaggtt     180
gcggttcttg agtcggagct acagcgggtg agcgaggaga accggcggct gggcgagatg     240
ctcagggagg tggcctccaa gtacgaggcc ctgcagggcc agttcaccga cgtggtcacg     300
gccggcggca acaacaacca ctaccacaac cagccgtcct ccgcgtcgga gggcgggtcg     360
gtgtcgccgt cgaggaagcg caagagcgag gagagcctcg gcacgccgcc accgtcgcat     420
actcagcagc agcactatgc cgccggcctc gcgtacgcgg tggcgccgga ccaggcggag     480
tgcacgtccg gcgagccgtg caagcgcatc cgggaggagt gcaagcccgt catctccaag     540
cgctacgtcc acgccgaccc ctccgacctc agcctggtgg tgaaggacgg gtaccaatgg     600
cgcaagtacg gcagaaggt gaccaaggac aacccatgcc ccagagccta cttccggtgc     660
tccttcgccc ccggctgccc cgtcaagaag aaggtgcaga ggagcgccga ggacaagacc     720
atactcgtgg cgacgtacga gggcgagcac aaccacaccc agcccccgcc gtcgcagccg     780
cagcagcaga acgacggctc cggcgccggc aagaacgccg ggaacgggaa gccgccccag     840
gcgccggcca cgcctcacca cccgcagcag cagcacaagc aggaagcggc agcggtcgtc     900
gtcagcggcg aatcggccgc ggcggcgtcc gagctgatcc ggcgcaacct ggcggagcag     960
atggccatga cgctgacgag ggaccccagc ttcaaggcgg cgctggtcac cgcgctctcc     1020
ggccggatcc tcgagctctc gccgaccagg gacatcaatt aa                        1062
```

<210> SEQ ID NO 11
<211> LENGTH: 353
<212> TYPE: PRT
<213> ORGANISM: Hordeum vulgare

<400> SEQUENCE: 11

```
Met Asp Pro Trp Met Gly Ser Gln Pro Ser Leu Ser Leu Asp Leu His
1               5                   10                  15

Val Gly Leu Pro Pro Met Gly His Pro His His Gln Ser Gln Tyr
                20                  25                  30

Gln Ala Pro Pro Met Ile Ala Leu Ala Lys Pro Lys Ile Leu Val Glu
            35                  40                  45

Glu Asn Phe Met Pro Leu Lys Lys Asp Pro Glu Val Ala Val Leu Glu
        50                  55                  60

Ser Glu Leu Gln Arg Val Ser Glu Glu Asn Arg Arg Leu Gly Glu Met
65                  70                  75                  80

Leu Arg Glu Val Ala Ser Lys Tyr Glu Ala Leu Gln Gly Gln Phe Thr
                85                  90                  95

Asp Val Val Thr Ala Gly Gly Asn Asn Asn His Tyr His Asn Gln Pro
            100                 105                 110

Ser Ser Ala Ser Glu Gly Gly Ser Val Ser Pro Ser Arg Lys Arg Lys
        115                 120                 125

Ser Glu Glu Ser Leu Gly Thr Pro Pro Ser His Thr Gln Gln Gln
    130                 135                 140
```

```
His Tyr Ala Ala Gly Leu Ala Tyr Ala Val Ala Pro Asp Gln Ala Glu
145                 150                 155                 160

Cys Thr Ser Gly Glu Pro Cys Lys Arg Ile Arg Glu Glu Cys Lys Pro
            165                 170                 175

Val Ile Ser Lys Arg Tyr Val His Ala Asp Pro Ser Asp Leu Ser Leu
        180                 185                 190

Val Val Lys Asp Gly Tyr Gln Trp Arg Lys Tyr Gly Gln Lys Val Thr
    195                 200                 205

Lys Asp Asn Pro Cys Pro Arg Ala Tyr Phe Arg Cys Ser Phe Ala Pro
210                 215                 220

Gly Cys Pro Val Lys Lys Val Gln Arg Ser Ala Glu Asp Lys Thr
225                 230                 235                 240

Ile Leu Val Ala Thr Tyr Glu Gly Glu His Asn His Thr Gln Pro Pro
                245                 250                 255

Pro Ser Gln Pro Gln Gln Asn Asp Gly Ser Gly Ala Gly Lys Asn
        260                 265                 270

Ala Gly Asn Gly Lys Pro Gln Ala Pro Ala Thr Pro His His Pro
        275                 280                 285

Gln Gln Gln His Lys Gln Glu Ala Ala Val Val Val Ser Gly Glu
    290                 295                 300

Ser Ala Ala Ala Ser Glu Leu Ile Arg Arg Asn Leu Ala Glu Gln
305                 310                 315                 320

Met Ala Met Thr Leu Thr Arg Asp Pro Ser Phe Lys Ala Ala Leu Val
                325                 330                 335

Thr Ala Leu Ser Gly Arg Ile Leu Glu Leu Ser Pro Thr Arg Asp Ile
            340                 345                 350

Asn

<210> SEQ ID NO 12
<211> LENGTH: 353
<212> TYPE: PRT
<213> ORGANISM: Hordeum vulgare

<400> SEQUENCE: 12

Met Asp Pro Trp Met Gly Ser Gln Pro Ser Leu Ser Leu Asp Leu His
1               5                   10                  15

Val Gly Leu Pro Pro Met Gly His Pro His His Gln Ser Gln Tyr
            20                  25                  30

Gln Ala Pro Pro Met Ile Ala Leu Ala Lys Pro Lys Ile Leu Val Glu
            35                  40                  45

Glu Asn Phe Met Pro Leu Lys Lys Asp Pro Glu Val Ala Leu Leu Glu
        50                  55                  60

Ser Glu Leu Gln Arg Val Ser Glu Glu Asn Arg Arg Leu Gly Glu Met
65                  70                  75                  80

Leu Arg Glu Val Ala Ser Lys Tyr Glu Ala Leu Gln Gly Gln Phe Thr
                85                  90                  95

Asp Met Val Thr Ala Gly Gly Asn Asn Asn His Tyr His Asn Gln Pro
            100                 105                 110

Ser Ser Ala Ser Glu Gly Gly Ser Val Ser Pro Ser Arg Lys Arg Lys
        115                 120                 125

Ser Glu Glu Ser Leu Gly Thr Pro Pro Pro Ser His Thr Gln Gln Gln
    130                 135                 140

His Tyr Ala Ala Gly Leu Ala Tyr Ala Val Ala Pro Asp Gln Ala Glu
145                 150                 155                 160
```

```
Cys Thr Ser Gly Glu Pro Cys Lys Arg Ile Arg Glu Glu Cys Lys Pro
                165                 170                 175
Val Ile Ser Lys Arg Tyr Val His Ala Asp Pro Ser Asp Leu Ser Leu
            180                 185                 190
Val Val Lys Asp Gly Tyr Gln Trp Arg Lys Tyr Gly Gln Lys Val Thr
        195                 200                 205
Lys Asp Asn Pro Cys Pro Arg Ala Tyr Phe Arg Cys Ser Phe Ala Pro
    210                 215                 220
Gly Cys Pro Val Lys Lys Val Gln Arg Ser Ala Glu Asp Lys Thr
225                 230                 235                 240
Ile Leu Val Ala Thr Tyr Glu Gly Glu His Asn His Thr Gln Pro Pro
                245                 250                 255
Pro Ser Gln Pro Gln Gln Asn Asp Gly Ser Gly Ala Gly Lys Asn
            260                 265                 270
Ala Gly Asn Gly Lys Pro Pro Gln Ala Pro Ala Thr Pro His His Pro
        275                 280                 285
Gln Gln Gln His Lys Gln Glu Ala Ala Val Val Ser Gly Glu
    290                 295                 300
Ser Ala Ala Ala Ser Glu Leu Ile Arg Arg Asn Leu Ala Glu Gln
305                 310                 315                 320
Met Ala Met Thr Leu Thr Arg Asp Pro Ser Phe Lys Ala Ala Leu Val
                325                 330                 335
Thr Ala Leu Ser Gly Arg Ile Leu Glu Leu Ser Pro Thr Arg Asp Ile
            340                 345                 350
Asn
```

<210> SEQ ID NO 13
<211> LENGTH: 1062
<212> TYPE: DNA
<213> ORGANISM: Artificial sequence
<220> FEATURE:
<223> OTHER INFORMATION: Coding sequence of mutant WRKY38 gene of HENZ-50

<400> SEQUENCE: 13

```
atggatccat ggatgggcag ccagccatcc ctgagcctcg acctgcacgt cggcctaccg      60
ccgatggggc acccgcacca ccaccagagc caataccagg cgccgccgat gatcgcgctg     120
gccaagccca gatcctcgt ggaggagaac ttcatgccac tcaagaagga ccctgaggtt     180
gcggttcttg agtcggagct acagcgggtg agcgaggaga ccggcggct gggcgagatg     240
ctcagggagg tggcctccaa gtacgaggcc ctgcagggcc agttcaccga cgtggtcacg     300
gccggcggca acaacaacca ctaccacaac cagccgtcct ccgcgtcgga gggcgggtcg     360
gtgtcgccgt cgaggaagcg caagagcgag gagagcctcg gcacgccgcc accgtcgcat     420
actcagcagc agcactatgc cgccggcctc gcgtacgcgg tggcgccgga ccaggcggag     480
tgcacgtccg cgagccgtg caagcgcatc cgggaggagt gcaagcccgt catctccaag     540
cgctacgtcc acgccgaccc ctccgacctc agcctggtgg tgaaggacgg gtaccaatga     600
cgcaagtacg gcagaaggt gaccaaggac aacccatgcc cagagccta cttccggtgc     660
tccttcgccc ccggctgccc cgtcaagaag aaggtgcaga ggagcgccga ggacaagacc     720
atactcgtgg cgacgtacga gggcgagcac aaccacaccc agccccgcc gtcgcagccg     780
cagcagcaga cgacggctc cggcgccggc aagaacgccg ggaacgggaa gccgccccag     840
gcgccggcca cgcctcacca cccgcagcag cagcacaagc aggaagcggc agcggtcgtc     900
```

```
gtcagcggcg aatcggccgc ggcggcgtcc gagctgatcc ggcgcaacct ggcggagcag    960
atggccatga cgctgacgag ggaccccagc ttcaaggcgg cgctggtcac cgcgctctcc   1020
ggccggatcc tcgagctctc gccgaccagg gacatcaatt aa                      1062
```

```
<210> SEQ ID NO 14
<211> LENGTH: 199
<212> TYPE: PRT
<213> ORGANISM: Artificial sequence
<220> FEATURE:
<223> OTHER INFORMATION: Protein sequence of mutant WRKY38 from barley
      mutant HENZ-50

<400> SEQUENCE: 14
```

```
Met Asp Pro Trp Met Gly Ser Gln Pro Ser Leu Ser Leu Asp Leu His
1               5                   10                  15

Val Gly Leu Pro Pro Met Gly His Pro His His Gln Ser Gln Tyr
            20                  25                  30

Gln Ala Pro Pro Met Ile Ala Leu Ala Lys Pro Lys Ile Leu Val Glu
            35                  40                  45

Glu Asn Phe Met Pro Leu Lys Lys Asp Pro Glu Val Ala Val Leu Glu
        50                  55                  60

Ser Glu Leu Gln Arg Val Ser Glu Glu Asn Arg Arg Leu Gly Glu Met
65                  70                  75                  80

Leu Arg Glu Val Ala Ser Lys Tyr Glu Ala Leu Gln Gly Gln Phe Thr
                85                  90                  95

Asp Val Val Thr Ala Gly Gly Asn Asn His Tyr His Asn Gln Pro
            100                 105                 110

Ser Ser Ala Ser Glu Gly Gly Ser Val Ser Pro Ser Arg Lys Arg Lys
        115                 120                 125

Ser Glu Glu Ser Leu Gly Thr Pro Pro Ser His Thr Gln Gln Gln
    130                 135                 140

His Tyr Ala Ala Gly Leu Ala Tyr Ala Val Ala Pro Asp Gln Ala Glu
145                 150                 155                 160

Cys Thr Ser Gly Glu Pro Cys Lys Arg Ile Arg Glu Glu Cys Lys Pro
                165                 170                 175

Val Ile Ser Lys Arg Tyr Val His Ala Asp Pro Ser Asp Leu Ser Leu
            180                 185                 190

Val Val Lys Asp Gly Tyr Gln
        195
```

```
<210> SEQ ID NO 15
<211> LENGTH: 17
<212> TYPE: DNA
<213> ORGANISM: Artificial sequence
<220> FEATURE:
<223> OTHER INFORMATION: Primer

<400> SEQUENCE: 15
cacgaagatg agccttg                                                     17

<210> SEQ ID NO 16
<211> LENGTH: 17
<212> TYPE: DNA
<213> ORGANISM: Artificial sequence
<220> FEATURE:
<223> OTHER INFORMATION: Primer

<400> SEQUENCE: 16
ttggctgatt tctgtgc                                                     17
```

```
<210> SEQ ID NO 17
<211> LENGTH: 17
<212> TYPE: DNA
<213> ORGANISM: Artificial sequence
<220> FEATURE:
<223> OTHER INFORMATION: Probe

<400> SEQUENCE: 17
aagtgatttg agcggct                                                      17

<210> SEQ ID NO 18
<211> LENGTH: 17
<212> TYPE: DNA
<213> ORGANISM: Artificial sequence
<220> FEATURE:
<223> OTHER INFORMATION: Probe

<400> SEQUENCE: 18
aggaagtggt ttgagcg                                                      17

<210> SEQ ID NO 19
<211> LENGTH: 15
<212> TYPE: DNA
<213> ORGANISM: Artificial sequence
<220> FEATURE:
<223> OTHER INFORMATION: Primer

<400> SEQUENCE: 19
gtcgtcgttc ccgtt                                                        15

<210> SEQ ID NO 20
<211> LENGTH: 15
<212> TYPE: DNA
<213> ORGANISM: Artificial sequence
<220> FEATURE:
<223> OTHER INFORMATION: Primer

<400> SEQUENCE: 20
ctgcaggtct gctcc                                                        15

<210> SEQ ID NO 21
<211> LENGTH: 15
<212> TYPE: DNA
<213> ORGANISM: Artificial sequence
<220> FEATURE:
<223> OTHER INFORMATION: Probe

<400> SEQUENCE: 21
actcgagctg accgt                                                        15

<210> SEQ ID NO 22
<211> LENGTH: 14
<212> TYPE: DNA
<213> ORGANISM: Artificial sequence
<220> FEATURE:
<223> OTHER INFORMATION: Probe

<400> SEQUENCE: 22
ctcgagctgg ccgt                                                         14

<210> SEQ ID NO 23
<211> LENGTH: 15
<212> TYPE: DNA
<213> ORGANISM: Artificial sequence
<220> FEATURE:
```

<223> OTHER INFORMATION: Primer

<400> SEQUENCE: 23
ctcagcctgg tggtg                                                        15

<210> SEQ ID NO 24
<211> LENGTH: 17
<212> TYPE: DNA
<213> ORGANISM: Artificial sequence
<220> FEATURE:
<223> OTHER INFORMATION: Primer

<400> SEQUENCE: 24
tgtccttggt caccttc                                                      17

<210> SEQ ID NO 25
<211> LENGTH: 17
<212> TYPE: DNA
<213> ORGANISM: Artificial sequence
<220> FEATURE:
<223> OTHER INFORMATION: Probe

<400> SEQUENCE: 25
ccaatgacgc aagtacg                                                      17

<210> SEQ ID NO 26
<211> LENGTH: 17
<212> TYPE: DNA
<213> ORGANISM: Artificial sequence
<220> FEATURE:
<223> OTHER INFORMATION: Probe

<400> SEQUENCE: 26
taccaatggc gcaagta                                                      17

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
aaacagaggt tgaggataac                                                   20

<210> SEQ ID NO 28
<211> LENGTH: 15
<212> TYPE: DNA
<213> ORGANISM: Artificial sequence
<220> FEATURE:
<223> OTHER INFORMATION: Primer

<400> SEQUENCE: 28
gccttcgcct tccat                                                        15

<210> SEQ ID NO 29
<211> LENGTH: 17
<212> TYPE: DNA
<213> ORGANISM: Artificial sequence
<220> FEATURE:
<223> OTHER INFORMATION: Probe

<400> SEQUENCE: 29
aggcaccgat caatacg                                                      17

```
<210> SEQ ID NO 30
<211> LENGTH: 17
<212> TYPE: DNA
<213> ORGANISM: Artificial sequence
<220> FEATURE:
<223> OTHER INFORMATION: Probe

<400> SEQUENCE: 30
aaggcaccgg tcaatac                                                        17

<210> SEQ ID NO 31
<211> LENGTH: 17
<212> TYPE: DNA
<213> ORGANISM: Artificial sequence
<220> FEATURE:
<223> OTHER INFORMATION: Non-standard tandem repeat W-box

<400> SEQUENCE: 31
tgacggtcgt attgacc                                                        17

<210> SEQ ID NO 32
<211> LENGTH: 17
<212> TYPE: DNA
<213> ORGANISM: Artificial sequence
<220> FEATURE:
<223> OTHER INFORMATION: Non-standard tandem repeat W-box

<400> SEQUENCE: 32
tgacagtggt attggcc                                                        17

<210> SEQ ID NO 33
<211> LENGTH: 17
<212> TYPE: DNA
<213> ORGANISM: Artificial sequence
<220> FEATURE:
<223> OTHER INFORMATION: Non-standard tandem repeat W-box

<400> SEQUENCE: 33
tgacagtggt actggcc                                                        17

<210> SEQ ID NO 34
<211> LENGTH: 18
<212> TYPE: DNA
<213> ORGANISM: Artificial sequence
<220> FEATURE:
<223> OTHER INFORMATION: Non-standard tandem repeat W-box

<400> SEQUENCE: 34
gtgacagtgg tattggcc                                                       18

<210> SEQ ID NO 35
<211> LENGTH: 17
<212> TYPE: DNA
<213> ORGANISM: Artificial sequence
<220> FEATURE:
<223> OTHER INFORMATION: Non-standard tandem repeat W-box

<400> SEQUENCE: 35
tgacggtcgt attgatc                                                        17

<210> SEQ ID NO 36
<211> LENGTH: 17
<212> TYPE: DNA
<213> ORGANISM: Artificial sequence
<220> FEATURE:
<223> OTHER INFORMATION: Non-standard tandem repeat W-box
```

```
<400> SEQUENCE: 36
tgaccgtcgt attgatc                                              17

<210> SEQ ID NO 37
<211> LENGTH: 11
<212> TYPE: DNA
<213> ORGANISM: Artificial sequence
<220> FEATURE:
<223> OTHER INFORMATION: Non-standard tandem repeat W-box

<400> SEQUENCE: 37
ttgacttgat c                                                    11

<210> SEQ ID NO 38
<211> LENGTH: 31
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: C or no nucleotide
<220> FEATURE:
<221> NAME/KEY: misc_feature
<222> LOCATION: (6)..(25)
<223> OTHER INFORMATION: n can be absent or any nucleotide

<400> SEQUENCE: 38
tgacnnnnnn nnnnnnnnnn nnnnnttgac c                              31

<210> SEQ ID NO 39
<211> LENGTH: 31
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: G or A
<220> FEATURE:
<221> NAME/KEY: misc_feature
<222> LOCATION: (6)..(25)
<223> OTHER INFORMATION: n can be absent or any nucleotide
<220> FEATURE:
<221> NAME/KEY: misc_feature
<222> LOCATION: (26)..(26)
<223> OTHER INFORMATION: n can be absent or C or T

<400> SEQUENCE: 39
tgacnnnnnn nnnnnnnnnn nnnnnntgrc c                              31

<210> SEQ ID NO 40
<211> LENGTH: 31
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: either G or A
<220> FEATURE:
<221> NAME/KEY: misc_feature
<222> LOCATION: (6)..(25)
<223> OTHER INFORMATION: n can be absent or any nucleotide

<400> SEQUENCE: 40
tgacnnnnnn nnnnnnnnnn nnnnnttgac c                              31
```

<210> SEQ ID NO 41
<211> LENGTH: 30
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: G or A
<220> FEATURE:
<221> NAME/KEY: misc_feature
<222> LOCATION: (6)..(25)
<223> OTHER INFORMATION: n can be absent or any nucleotide

<400> SEQUENCE: 41
tgacnnnnnn nnnnnnnnnn nnnnnttgac                                30

<210> SEQ ID NO 42
<211> LENGTH: 31
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: n can be absent or C
<220> FEATURE:
<221> NAME/KEY: misc_feature
<222> LOCATION: (6)..(25)
<223> OTHER INFORMATION: n can be absent or any nucleotide
<220> FEATURE:
<221> NAME/KEY: misc_feature
<222> LOCATION: (26)..(26)
<223> OTHER INFORMATION: C or T
<220> FEATURE:
<221> NAME/KEY: misc_feature
<222> LOCATION: (29)..(29)
<223> OTHER INFORMATION: G or A

<400> SEQUENCE: 42
tgacnnnnnn nnnnnnnnnn nnnnnntgnc c                              31

<210> SEQ ID NO 43
<211> LENGTH: 31
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: C or no nucleotide
<220> FEATURE:
<221> NAME/KEY: misc_feature
<222> LOCATION: (6)..(25)
<223> OTHER INFORMATION: n can be absent or any nucleotide
<220> FEATURE:
<221> NAME/KEY: misc_feature
<222> LOCATION: (29)..(29)
<223> OTHER INFORMATION: G or A

<400> SEQUENCE: 43
tgacnnnnnn nnnnnnnnnn nnnnnctgnc c                              31

<210> SEQ ID NO 44
<211> LENGTH: 31
<212> TYPE: DNA
<213> ORGANISM: Artificial Sequence
<220> FEATURE:

```
<223> OTHER INFORMATION: W-box
<220> FEATURE:
<221> NAME/KEY: misc_feature
<222> LOCATION: (5)..(5)
<223> OTHER INFORMATION: C or no nucleotide
<220> FEATURE:
<221> NAME/KEY: misc_feature
<222> LOCATION: (6)..(25)
<223> OTHER INFORMATION: n can be absent or any nucleotide
<220> FEATURE:
<221> NAME/KEY: misc_feature
<222> LOCATION: (26)..(26)
<223> OTHER INFORMATION: C or T

<400> SEQUENCE: 44
tgacnnnnnn nnnnnnnnnn nnnnnntggc c                              31

<210> SEQ ID NO 45
<211> LENGTH: 31
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: C or no nucleotide
<220> FEATURE:
<221> NAME/KEY: misc_feature
<222> LOCATION: (6)..(25)
<223> OTHER INFORMATION: n can be absent or any nucleotide

<400> SEQUENCE: 45
tgacnnnnnn nnnnnnnnnn nnnnnctgac c                              31

<210> SEQ ID NO 46
<211> LENGTH: 31
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: C or no nucleotide
<220> FEATURE:
<221> NAME/KEY: misc_feature
<222> LOCATION: (6)..(25)
<223> OTHER INFORMATION: n can be absent or any nucleotide

<400> SEQUENCE: 46
tgacnnnnnn nnnnnnnnnn nnnnnttggc c                              31

<210> SEQ ID NO 47
<211> LENGTH: 31
<212> TYPE: DNA
<213> ORGANISM: Artificial Sequence
<220> FEATURE:
<223> OTHER INFORMATION: W-box
<220> FEATURE:
<221> NAME/KEY: misc_feature
<222> LOCATION: (5)..(5)
<223> OTHER INFORMATION: C or no nucleotide
<220> FEATURE:
<221> NAME/KEY: misc_feature
<222> LOCATION: (6)..(25)
<223> OTHER INFORMATION: n can be absent or any nucleotide

<400> SEQUENCE: 47
tgacnnnnnn nnnnnnnnnn nnnnnttgat c                              31
```

```
<210> SEQ ID NO 48
<211> LENGTH: 53
<212> TYPE: DNA
<213> ORGANISM: Artificial Sequence
<220> FEATURE:
<223> OTHER INFORMATION: (Amy6-4)
<220> FEATURE:
<221> NAME/KEY: misc_feature
<222> LOCATION: (1)..(53)
<223> OTHER INFORMATION: (Amy6-4)

<400> SEQUENCE: 48
taactgacgg tcgtattgac cggtgccttc ttatggaagg cgaaggctgc ctc        53

<210> SEQ ID NO 49
<211> LENGTH: 53
<212> TYPE: DNA
<213> ORGANISM: Artificial Sequence
<220> FEATURE:
<223> OTHER INFORMATION: amy1_1a
<220> FEATURE:
<221> NAME/KEY: misc_feature
<222> LOCATION: (1)..(53)
<223> OTHER INFORMATION: amy1_1a

<400> SEQUENCE: 49
taactgacgg tcgtattgac cggtgccttc ttatggaagg cgaaggctgc ctc        53

<210> SEQ ID NO 50
<211> LENGTH: 53
<212> TYPE: DNA
<213> ORGANISM: Artificial Sequence
<220> FEATURE:
<223> OTHER INFORMATION: amy1_1b
<220> FEATURE:
<221> NAME/KEY: misc_feature
<222> LOCATION: (1)..(53)
<223> OTHER INFORMATION: amy1_1b

<400> SEQUENCE: 50
taactgacgg tcgtattgac cggtgccttc ttatggaagg cgaaggctgc ctc        53

<210> SEQ ID NO 51
<211> LENGTH: 53
<212> TYPE: DNA
<213> ORGANISM: Artificial Sequence
<220> FEATURE:
<223> OTHER INFORMATION: amy1_1c
<220> FEATURE:
<221> NAME/KEY: misc_feature
<222> LOCATION: (1)..(53)
<223> OTHER INFORMATION: amy1_1c

<400> SEQUENCE: 51
taactgacgg tcgtattgac cagtgccttc ttatggaagg cgaaggctgc ctc        53

<210> SEQ ID NO 52
<211> LENGTH: 29
<212> TYPE: DNA
<213> ORGANISM: Artificial Sequence
<220> FEATURE:
<223> OTHER INFORMATION: Amy46
<220> FEATURE:
<221> NAME/KEY: misc_feature
<222> LOCATION: (1)..(29)
<223> OTHER INFORMATION: Amy46

<400> SEQUENCE: 52
taactgacag tcgtactggc cggtgcctt                                   29
```

```
<210> SEQ ID NO 53
<211> LENGTH: 29
<212> TYPE: DNA
<213> ORGANISM: Artificial Sequence
<220> FEATURE:
<223> OTHER INFORMATION: amy1_2
<220> FEATURE:
<221> NAME/KEY: misc_feature
<222> LOCATION: (1)..(29)
<223> OTHER INFORMATION: amy1_2

<400> SEQUENCE: 53
taagtgacag tggtattggc cggtgcctt                                         29

<210> SEQ ID NO 54
<211> LENGTH: 53
<212> TYPE: DNA
<213> ORGANISM: Artificial Sequence
<220> FEATURE:
<223> OTHER INFORMATION: Amy6-4
<220> FEATURE:
<221> NAME/KEY: misc_feature
<222> LOCATION: (1)..(53)
<223> OTHER INFORMATION: Amy6-4

<400> SEQUENCE: 54
catctacatc acttgggcat tgaatcgcct tttgagctca ccgtaccggc cga             53

<210> SEQ ID NO 55
<211> LENGTH: 53
<212> TYPE: DNA
<213> ORGANISM: Artificial Sequence
<220> FEATURE:
<223> OTHER INFORMATION: amy1_1a
<220> FEATURE:
<221> NAME/KEY: misc_feature
<222> LOCATION: (1)..(53)
<223> OTHER INFORMATION: amy1_1a

<400> SEQUENCE: 55
catctacatc acttgggcat tgaatcgcct tttgagctca ccgtaccggc cga             53

<210> SEQ ID NO 56
<211> LENGTH: 53
<212> TYPE: DNA
<213> ORGANISM: Artificial Sequence
<220> FEATURE:
<223> OTHER INFORMATION: amy1_1b
<220> FEATURE:
<221> NAME/KEY: misc_feature
<222> LOCATION: (1)..(53)
<223> OTHER INFORMATION: amy1_1b

<400> SEQUENCE: 56
catctacatc acttgggcat tgaatcgcct tttgagctca ccgtaccggc cga             53

<210> SEQ ID NO 57
<211> LENGTH: 53
<212> TYPE: DNA
<213> ORGANISM: Artificial Sequence
<220> FEATURE:
<223> OTHER INFORMATION: amy1_1c
<220> FEATURE:
<221> NAME/KEY: misc_feature
<222> LOCATION: (1)..(53)
<223> OTHER INFORMATION: amy1_1c

<400> SEQUENCE: 57
catctccatc acttgggcat tgaatcgcct tttgagctca ccgcaccggc cga             53
```

<210> SEQ ID NO 58
<211> LENGTH: 53
<212> TYPE: DNA
<213> ORGANISM: Artificial Sequence
<220> FEATURE:
<223> OTHER INFORMATION: Amy46
<220> FEATURE:
<221> NAME/KEY: misc_feature
<222> LOCATION: (1)..(53)
<223> OTHER INFORMATION: Amy46

<400> SEQUENCE: 58
cttgtcgaag gctggatcca tcagtcgcct tttgagctca ccgcaccggc cga        53

<210> SEQ ID NO 59
<211> LENGTH: 53
<212> TYPE: DNA
<213> ORGANISM: Artificial Sequence
<220> FEATURE:
<223> OTHER INFORMATION: amy1_2
<220> FEATURE:
<221> NAME/KEY: misc_feature
<222> LOCATION: (1)..(53)
<223> OTHER INFORMATION: amy1_2

<400> SEQUENCE: 59
ctcatcgaag ccggtgctca tcattcgcct tttgagctca ccgcaccggc cga        53

<210> SEQ ID NO 60
<211> LENGTH: 29
<212> TYPE: DNA
<213> ORGANISM: Artificial Sequence
<220> FEATURE:
<223> OTHER INFORMATION: Amy6-4
<220> FEATURE:
<221> NAME/KEY: misc_feature
<222> LOCATION: (1)..(29)
<223> OTHER INFORMATION: Amy6-4

<400> SEQUENCE: 60
taacaaactc cggccgacat atccactgg                                   29

<210> SEQ ID NO 61
<211> LENGTH: 29
<212> TYPE: DNA
<213> ORGANISM: Artificial Sequence
<220> FEATURE:
<223> OTHER INFORMATION: amy1_1a
<220> FEATURE:
<221> NAME/KEY: misc_feature
<222> LOCATION: (1)..(29)
<223> OTHER INFORMATION: amy1_1a

<400> SEQUENCE: 61
taacaaactc cggccgacat atccactgg                                   29

<210> SEQ ID NO 62
<211> LENGTH: 29
<212> TYPE: DNA
<213> ORGANISM: Artificial Sequence
<220> FEATURE:
<223> OTHER INFORMATION: amy1_1b
<220> FEATURE:
<221> NAME/KEY: misc_feature
<222> LOCATION: (1)..(29)
<223> OTHER INFORMATION: amy1_1b

<400> SEQUENCE: 62

-continued taacaaactc cggccgacat atccactgg                                29

<210> SEQ ID NO 63
<211> LENGTH: 29
<212> TYPE: DNA
<213> ORGANISM: Artificial Sequence
<220> FEATURE:
<223> OTHER INFORMATION: amy1_1c
<220> FEATURE:
<221> NAME/KEY: misc_feature
<222> LOCATION: (1)..(29)
<223> OTHER INFORMATION: amy1_1c

<400> SEQUENCE: 63
taacaaactc cggccaacat atccactgg                                29

<210> SEQ ID NO 64
<211> LENGTH: 29
<212> TYPE: DNA
<213> ORGANISM: Artificial Sequence
<220> FEATURE:
<223> OTHER INFORMATION: Amy46
<220> FEATURE:
<221> NAME/KEY: misc_feature
<222> LOCATION: (1)..(29)
<223> OTHER INFORMATION: Amy46

<400> SEQUENCE: 64
taacaaactc cggccgacat atccatcga                                29

<210> SEQ ID NO 65
<211> LENGTH: 29
<212> TYPE: DNA
<213> ORGANISM: Artificial Sequence
<220> FEATURE:
<223> OTHER INFORMATION: amy1_2
<220> FEATURE:
<221> NAME/KEY: misc_feature
<222> LOCATION: (1)..(29)
<223> OTHER INFORMATION: amy1_2

<400> SEQUENCE: 65
taacaaactc cggccgacat atccatcga                                29

<210> SEQ ID NO 66
<211> LENGTH: 42
<212> TYPE: DNA
<213> ORGANISM: Artificial Sequence
<220> FEATURE:
<223> OTHER INFORMATION: amy2_1
<220> FEATURE:
<221> NAME/KEY: misc_feature
<222> LOCATION: (1)..(42)
<223> OTHER INFORMATION: amy2_1

<400> SEQUENCE: 66
ggaatttgtg ccggcccgga ttgacttgac catcatctgt tg                 42

<210> SEQ ID NO 67
<211> LENGTH: 43
<212> TYPE: DNA
<213> ORGANISM: Artificial Sequence
<220> FEATURE:
<223> OTHER INFORMATION: amy2_2
<220> FEATURE:
<221> NAME/KEY: misc_feature
<222> LOCATION: (1)..(43)
<223> OTHER INFORMATION: amy2_2

<400> SEQUENCE: 67

```
ggaggctgtg ccaacccagc ttgacttgac catcaccagt tac        43
```

<210> SEQ ID NO 68
<211> LENGTH: 48
<212> TYPE: DNA
<213> ORGANISM: Artificial Sequence
<220> FEATURE:
<223> OTHER INFORMATION: amy2_3
<220> FEATURE:
<221> NAME/KEY: misc_feature
<222> LOCATION: (1)..(48)
<223> OTHER INFORMATION: amy2_3

<400> SEQUENCE: 68

```
ggaacttgtg ccaccccgga ttgacttgac cgtcatcggc tccggatg    48
```

<210> SEQ ID NO 69
<211> LENGTH: 36
<212> TYPE: DNA
<213> ORGANISM: Artificial Sequence
<220> FEATURE:
<223> OTHER INFORMATION: amy2_1
<220> FEATURE:
<221> NAME/KEY: misc_feature
<222> LOCATION: (1)..(36)
<223> OTHER INFORMATION: amy2_1

<400> SEQUENCE: 69

```
caccttttct cgtaacagag tctggtatcc atgcag              36
```

<210> SEQ ID NO 70
<211> LENGTH: 36
<212> TYPE: DNA
<213> ORGANISM: Artificial Sequence
<220> FEATURE:
<223> OTHER INFORMATION: amy2_2
<220> FEATURE:
<221> NAME/KEY: misc_feature
<222> LOCATION: (1)..(36)
<223> OTHER INFORMATION: amy2_2

<400> SEQUENCE: 70

```
tccatttttc cataacagag gccggtaccc atgcat              36
```

<210> SEQ ID NO 71
<211> LENGTH: 36
<212> TYPE: DNA
<213> ORGANISM: Artificial Sequence
<220> FEATURE:
<223> OTHER INFORMATION: amy2_3
<220> FEATURE:
<221> NAME/KEY: misc_feature
<222> LOCATION: (1)..(36)
<223> OTHER INFORMATION: amy2_3

<400> SEQUENCE: 71

```
cacctttat cgtaacagag tccggtatcc atgcag               36
```

<210> SEQ ID NO 72
<211> LENGTH: 18
<212> TYPE: DNA
<213> ORGANISM: Artificial Sequence
<220> FEATURE:
<223> OTHER INFORMATION: amy1_1 cluster
<220> FEATURE:
<221> NAME/KEY: misc_feature
<222> LOCATION: (1)..(18)
<223> OTHER INFORMATION: amy1_1

```
<400> SEQUENCE: 72
ctgacggtcg tattgatc                                              18

<210> SEQ ID NO 73
<211> LENGTH: 19
<212> TYPE: DNA
<213> ORGANISM: Artificial Sequence
<220> FEATURE:
<223> OTHER INFORMATION: HENZ-53 target specific Forward Primer
<220> FEATURE:
<221> NAME/KEY: misc_feature
<222> LOCATION: (1)..(19)
<223> OTHER INFORMATION: HENZ-53

<400> SEQUENCE: 73
gtcagctact gggagtatt                                             19

<210> SEQ ID NO 74
<211> LENGTH: 15
<212> TYPE: DNA
<213> ORGANISM: Artificial Sequence
<220> FEATURE:
<223> OTHER INFORMATION: HENZ-53 Target Specific Reverse Primer
<220> FEATURE:
<221> NAME/KEY: misc_feature
<222> LOCATION: (1)..(15)
<223> OTHER INFORMATION: HENZ-53 Rev Primer

<400> SEQUENCE: 74
tcttcgcgac gacac                                                 15

<210> SEQ ID NO 75
<211> LENGTH: 20
<212> TYPE: DNA
<213> ORGANISM: Artificial Sequence
<220> FEATURE:
<223> OTHER INFORMATION: HENZ-53 Mutant specific probe
<220> FEATURE:
<221> NAME/KEY: misc_feature
<222> LOCATION: (1)..(20)
<223> OTHER INFORMATION: HENZ-53 Mutant specific probe

<400> SEQUENCE: 75
tgcatgaaat aaactgcaga                                            20

<210> SEQ ID NO 76
<211> LENGTH: 19
<212> TYPE: DNA
<213> ORGANISM: Artificial Sequence
<220> FEATURE:
<223> OTHER INFORMATION: HENZ-53 Reference specific detection probe
<220> FEATURE:
<221> NAME/KEY: misc_feature
<222> LOCATION: (1)..(19)
<223> OTHER INFORMATION: HENZ-53 Reference specific detection probe

<400> SEQUENCE: 76
tgcatggaat aaactgcag                                             19

<210> SEQ ID NO 77
<211> LENGTH: 18
<212> TYPE: DNA
<213> ORGANISM: Artificial Sequence
<220> FEATURE:
<223> OTHER INFORMATION: HENZ-54 Target specific forward primer
<220> FEATURE:
<221> NAME/KEY: misc_feature
<222> LOCATION: (1)..(18)
<223> OTHER INFORMATION: HENZ-54 target specific forward primer
```

<400> SEQUENCE: 77
tgctaatcca agcaaacg                                                      18

<210> SEQ ID NO 78
<211> LENGTH: 20
<212> TYPE: DNA
<213> ORGANISM: Artificial Sequence
<220> FEATURE:
<223> OTHER INFORMATION: HENZ-54 Target specific reverse primer
<220> FEATURE:
<221> NAME/KEY: misc_feature
<222> LOCATION: (1)..(20)
<223> OTHER INFORMATION: HENZ-54 Target specific reverse primer

<400> SEQUENCE: 78
tttgtggaca gatttttgga                                                    20

<210> SEQ ID NO 79
<211> LENGTH: 17
<212> TYPE: DNA
<213> ORGANISM: Artificial Sequence
<220> FEATURE:
<223> OTHER INFORMATION: HENZ-54 mutant specific detection probe
<220> FEATURE:
<221> NAME/KEY: misc_feature
<222> LOCATION: (1)..(17)
<223> OTHER INFORMATION: HENZ-54 Reference specific detection probe

<400> SEQUENCE: 79
agcctgacaa accagtg                                                       17

<210> SEQ ID NO 80
<211> LENGTH: 16
<212> TYPE: DNA
<213> ORGANISM: Artificial Sequence
<220> FEATURE:
<223> OTHER INFORMATION: HENZ-54 Reference specific detection probe
<220> FEATURE:
<221> NAME/KEY: misc_feature
<222> LOCATION: (1)..(16)
<223> OTHER INFORMATION: HENZ-54 Reference specific detection probe

<400> SEQUENCE: 80
aagcctggca aaccag                                                        16

<210> SEQ ID NO 81
<211> LENGTH: 15
<212> TYPE: DNA
<213> ORGANISM: Artificial Sequence
<220> FEATURE:
<223> OTHER INFORMATION: amy1-1 Foward primer
<220> FEATURE:
<221> NAME/KEY: misc_feature
<222> LOCATION: (1)..(15)
<223> OTHER INFORMATION: primer

<400> SEQUENCE: 81
gactggggcc tgaag                                                         15

<210> SEQ ID NO 82
<211> LENGTH: 15
<212> TYPE: DNA
<213> ORGANISM: Artificial Sequence
<220> FEATURE:
<223> OTHER INFORMATION: amy1-1 reverse primer
<220> FEATURE:
<221> NAME/KEY: misc_feature
<222> LOCATION: (1)..(15)

```
<223> OTHER INFORMATION: primer

<400> SEQUENCE: 82
gtgccgggtc ctgac                                                           15

<210> SEQ ID NO 83
<211> LENGTH: 19
<212> TYPE: DNA
<213> ORGANISM: Artificial Sequence
<220> FEATURE:
<223> OTHER INFORMATION: amy1-1 probe
<220> FEATURE:
<221> NAME/KEY: misc_feature
<222> LOCATION: (1)..(19)
<223> OTHER INFORMATION: probe

<400> SEQUENCE: 83
agatcgatcg cctggtgtc                                                       19

<210> SEQ ID NO 84
<211> LENGTH: 17
<212> TYPE: DNA
<213> ORGANISM: Artificial Sequence
<220> FEATURE:
<223> OTHER INFORMATION: amy1-2 foward primer
<220> FEATURE:
<221> NAME/KEY: misc_feature
<222> LOCATION: (1)..(17)
<223> OTHER INFORMATION: primer

<400> SEQUENCE: 84
agatcgatcg tctggtg                                                         17

<210> SEQ ID NO 85
<211> LENGTH: 18
<212> TYPE: DNA
<213> ORGANISM: Artificial Sequence
<220> FEATURE:
<223> OTHER INFORMATION: amy-1-2 reverse sequence
<220> FEATURE:
<221> NAME/KEY: misc_feature
<222> LOCATION: (1)..(18)
<223> OTHER INFORMATION: primer

<400> SEQUENCE: 85
tccatgatct gcagcttg                                                        18

<210> SEQ ID NO 86
<211> LENGTH: 19
<212> TYPE: DNA
<213> ORGANISM: Artificial Sequence
<220> FEATURE:
<223> OTHER INFORMATION: amy1-2 probe
<220> FEATURE:
<221> NAME/KEY: misc_feature
<222> LOCATION: (1)..(19)
<223> OTHER INFORMATION: probe

<400> SEQUENCE: 86
tcaatcagga cccgacagg                                                       19

<210> SEQ ID NO 87
<211> LENGTH: 16
<212> TYPE: DNA
<213> ORGANISM: Artificial Sequence
<220> FEATURE:
<223> OTHER INFORMATION: amy2 forward primer
<220> FEATURE:
<221> NAME/KEY: misc_feature
```

```
<222> LOCATION: (1)..(16)
<223> OTHER INFORMATION: primer

<400> SEQUENCE: 87
cgagctcaag gagtgg                                                      16

<210> SEQ ID NO 88
<211> LENGTH: 17
<212> TYPE: DNA
<213> ORGANISM: Artificial Sequence
<220> FEATURE:
<223> OTHER INFORMATION: amy2 reverse primer
<220> FEATURE:
<221> NAME/KEY: misc_feature
<222> LOCATION: (1)..(17)
<223> OTHER INFORMATION: primer

<400> SEQUENCE: 88
cgtcgatgta caccttg                                                     17

<210> SEQ ID NO 89
<211> LENGTH: 18
<212> TYPE: DNA
<213> ORGANISM: Artificial Sequence
<220> FEATURE:
<223> OTHER INFORMATION: amy2 probe
<220> FEATURE:
<221> NAME/KEY: misc_feature
<222> LOCATION: (1)..(18)
<223> OTHER INFORMATION: probe

<400> SEQUENCE: 89
aagagcgacc tcggcttc                                                    18

<210> SEQ ID NO 90
<211> LENGTH: 18
<212> TYPE: DNA
<213> ORGANISM: Artificial Sequence
<220> FEATURE:
<223> OTHER INFORMATION: Bgl2 forward primer
<220> FEATURE:
<221> NAME/KEY: misc_feature
<222> LOCATION: (1)..(18)
<223> OTHER INFORMATION: primer

<400> SEQUENCE: 90
taccagaacc tgttcgac                                                    18

<210> SEQ ID NO 91
<211> LENGTH: 16
<212> TYPE: DNA
<213> ORGANISM: Artificial Sequence
<220> FEATURE:
<223> OTHER INFORMATION: Bgl2 reverse primer
<220> FEATURE:
<221> NAME/KEY: misc_feature
<222> LOCATION: (1)..(16)
<223> OTHER INFORMATION: primer

<400> SEQUENCE: 91
acaccaccag cttcac                                                      16

<210> SEQ ID NO 92
<211> LENGTH: 18
<212> TYPE: DNA
<213> ORGANISM: Artificial Sequence
<220> FEATURE:
<223> OTHER INFORMATION: Bgl2 probe
<220> FEATURE:
```

```
<221> NAME/KEY: misc_feature
<222> LOCATION: (1)..(18)
<223> OTHER INFORMATION: probe

<400> SEQUENCE: 92
accgtggacg ccttctac                                                 18

<210> SEQ ID NO 93
<211> LENGTH: 18
<212> TYPE: DNA
<213> ORGANISM: Artificial Sequence
<220> FEATURE:
<223> OTHER INFORMATION: LD forward primer
<220> FEATURE:
<221> NAME/KEY: misc_feature
<222> LOCATION: (1)..(18)
<223> OTHER INFORMATION: primer

<400> SEQUENCE: 93
cttcgatggg gtttgaac                                                 18

<210> SEQ ID NO 94
<211> LENGTH: 18
<212> TYPE: DNA
<213> ORGANISM: Artificial Sequence
<220> FEATURE:
<223> OTHER INFORMATION: LD reverse primer
<220> FEATURE:
<221> NAME/KEY: misc_feature
<222> LOCATION: (1)..(18)
<223> OTHER INFORMATION: primer

<400> SEQUENCE: 94
ccgatttcct caccaaag                                                 18

<210> SEQ ID NO 95
<211> LENGTH: 21
<212> TYPE: DNA
<213> ORGANISM: Artificial Sequence
<220> FEATURE:
<223> OTHER INFORMATION: LD probe
<220> FEATURE:
<221> NAME/KEY: misc_feature
<222> LOCATION: (1)..(21)
<223> OTHER INFORMATION: probe

<400> SEQUENCE: 95
cctgtgcagg tgaattcatc a                                             21

<210> SEQ ID NO 96
<211> LENGTH: 53
<212> TYPE: DNA
<213> ORGANISM: Artificial Sequence
<220> FEATURE:
<223> OTHER INFORMATION: HENZ-43 amy1_1
<220> FEATURE:
<221> NAME/KEY: misc_feature
<222> LOCATION: (1)..(53)
<223> OTHER INFORMATION: HENZ-43 amy1_1

<400> SEQUENCE: 96
taactgacgg tcgtattgat cggtgccttc ttatggaagg cgaaggctgc ctc           53

<210> SEQ ID NO 97
<211> LENGTH: 53
<212> TYPE: DNA
<213> ORGANISM: Artificial Sequence
<220> FEATURE:
<223> OTHER INFORMATION: HENZ-43 amy1_1
```

```
<220> FEATURE:
<221> NAME/KEY: misc_feature
<222> LOCATION: (1)..(53)
<223> OTHER INFORMATION: HENZ-43 amy1_1

<400> SEQUENCE: 97
catctacatc acttgggcat tgaatcgcct tttgagctca ccgtaccggc cga          53

<210> SEQ ID NO 98
<211> LENGTH: 29
<212> TYPE: DNA
<213> ORGANISM: Artificial Sequence
<220> FEATURE:
<223> OTHER INFORMATION: HENZ-43 amy1_1
<220> FEATURE:
<221> NAME/KEY: misc_feature
<222> LOCATION: (1)..(29)
<223> OTHER INFORMATION: HENZ-43 amy1_1

<400> SEQUENCE: 98
taacaaactc cggccgacat atccactgg                                    29

<210> SEQ ID NO 99
<211> LENGTH: 24
<212> TYPE: PRT
<213> ORGANISM: Artificial Sequence
<220> FEATURE:
<223> OTHER INFORMATION: HRTdb consensus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 99

Val Cys Gly Xaa Asp Gly Xaa Cys Xaa Cys Xaa Pro Val Xaa Arg Lys
1               5                   10                  15

Arg Cys Xaa His Lys Gly Xaa Arg
            20
```

BARLEY WITH INCREASED HYDROLYTIC ENZYME ACTIVITY

CROSS-REFERENCE TO RELATED APPLICATIONS

This application is a national phase entry pursuant to 35 U.S.C. § 371 of International Application No. PCT/EP2018/086733 filed Dec. 21, 2018, which claims the benefit of priority to European Application No. 17210964.7 filed Dec. 28, 2017, the content of each of which is incorporated by reference herein in their entirety for all purposes.

SEQUENCE LISTING

The present application contains a Sequence Listing which has been submitted in ASCII format via EFS-Web and is incorporated herein by reference in its entirety. The ASCII copy, created on Oct. 19, 2023, is named "2023-10-19_01130-0013-00US_Replacement Sequence Listing ST0 25.txt" and is 55,295 bytes in size.

TECHNICAL FIELD

The present invention relates to barley plants having increased hydrolytic enzyme activity. In particular, the barley plants of the invention may have increased hydrolytic enzyme activity in the early phases of germination.

BACKGROUND

In commercial malting processes, barley grains are germinated, or malted, under controlled conditions that allow partial mobilization of the starch and protein reserves of the starchy endosperm over a period of 4-6 days. The malting process is typically initiated by immersing the dry barley grain in water. This process is known as steeping where the objective is not only to clean the grain, but also to raise its moisture content to about 40% (w/w) so that the endosperm mobilization step that follows will occur more quickly. During steeping, the water is drained once to allow re-aeration of the grain. This step is known as the 'air rest' and is considered necessary, primarily because the submerged grain becomes starved of oxygen after about 16 h. After an 'air rest' of about 8 h, the grain is re-immersed in water to complete the steeping treatment over another 8-h period—or in a series of re-steeping steps. The two-step steeping process to increase the moisture content of the dry grain to 40%, or higher, takes about 32 h overall.

The steeped grain is spread for germination, during which enzymes secreted from aleurone and scutellar epithelial cells—together with some that pre-exist in the starchy endosperm cells—degrade cell walls, starch and protein. Under normal conditions of germination, the phytohormone gibberellic acid (GA) is believed to be synthesized in the nodal region, or elsewhere in the embryo, from where it diffuses along the water gradient.

The maltster usually aims to rapidly induce synthesis of as many of the starch-degrading enzymes in the grains as possible. In many commercial malting programs, GA may be added to speed up the process of enzyme secretion from the aleurone layer. The starch-degrading enzymes-which include α- and β-amylases, starch debranching enzymes (e.g. limit dextrinase) and α-glucosidases-partially depolymerize the starch reserves of the grain to monosaccharides, oligosaccharides, and glucose. The depolymerization products of starch are subsequently used by yeast cells as a carbon source and are fermented into beer ethanol.

α-amylases have a primary role in degradation of starch in endosperm. The expression of α-amylases is tightly regulated in cereal plants. In wild type barley, there is very little expression of α-amylase genes during endosperm growth and maturation consistent with the extensive accumulation of starch during this period. During germination α-amylase activity is increased. The tight regulation of α-amylase activity is important because aberrant α-amylase activity may have severe consequences on plant health. For example, in certain barley varieties premature germination may occur. This may be associated with shoot and root growth, high α-amylase production, and shriveling of the grain at maturity (Green et al., 1997). Also, it has been found that α-amylase activity frequently is increased in shrivelled grains compared to normal grains (Green et al., 1997). Cv. Himalaya barley carrying the sin1 mutation has also consistently been demonstrated to have both premature sprouting and high α-amylase production (Green et al., 1997). Over-expression of α-amylase genes in developing endosperm of rice produced various degrees of "chalky" grains, i.e. grains comprising immature, loosely packed starch granules (Nakata et al. 2017). Maltsters also try to induce high levels of enzymes that degrade cell wall polysaccharides in the barley grain, in particular the (1,3;1,4)-β-glucans and arabinoxylans. Incompletely degraded (1,3;1,4)-β-glucans can be especially troublesome for brewers, because these can be extracted from the malt in soluble forms that form highly viscous aqueous solutions that slow filtration processes in the brewery and contribute to undesirable haze in the final beer. Thus, low levels of soluble (1,3;1,4)-β-glucan represent an important malting quality parameter, while high levels of (1,3;1,4)-β-glucanase enzymes remain important measures of malt quality.

As noted above, the germination process typically takes about 4-to-5 days. Following the controlled germination steps, the wet malt is dried from about a moisture content of 40% to 4-to-5%. This drying process, termed kilning, is very energy consuming and represents a major cost for the industry. The entire process including kiln drying is typically 6-7 days.

In the brewery, the kiln-dried malt is milled to break open the grain, and the resulting content is extracted with hot water in a process known as mashing. The extracted material includes partially degraded starch, protein and cell wall molecules as described above, and these are further degraded by endogenous grain enzymes that were extracted from the malt. At this stage, some brewers add additional—and generally cheaper carbon sources (adjuncts)—to support the subsequent yeast fermentation process and to offset the higher costs of malt. Said adjuncts can be barley, rice, wheat or other cereal flours from un-germinated grain, but their addition may necessitate the concomitant addition of hydrolytic enzymes, because there are insufficient endogenous enzymes in the malt to degrade the components of the adjunct. The added enzymes are usually from unpurified and relatively cheap extracts of fungal and/or bacterial cultures. The addition of exogenous enzymes is not legal in some countries, particularly where beer must be produced under tightly regulated settings.

Further degradation of the starch, and other endosperm components extracted in hot water, proceed in a process known as saccharification. Following mashing, the extracts are filtered, often in a lauter tun, and cooled. The extract may be boiled in the presence of hops or hop extracts, and upon cooling yeast cultures are added for the fermentation of

SUMMARY

As outlined above, one of the time and energy consuming steps of beer production is malting. A rate limiting step in the malting procedure is the synthesis of sufficient starch-degrading enzymes in the grains. Accordingly, there is a need for the provision of materials and methods, which can reduce the time required for malting. In particular, there is a need for methods, allowing germination of cereal grains comprising sufficient starch-degrading enzymes shortly after the initiation of germination.

However, as noted above high α-amylase activity is associated with unwanted effects on plant fitness. In particular, high α-amylase activity may be associated with reduced grain starch content and/or pre-harvest sprouting. Pre-harvest sprouting is the phenomenon where physiologically mature kernels on a plant start behaving as a germinating seed rather than a starch-storing grain. Pre-harvest sprouting is characterized by the precocious germination of grains before harvest with consequent reductions in seed viability and end-use value. Thus, pre-harvest sprouting predisposes barley to a relatively rapid loss of seed viability, and since the malting process requires germination, its occurrence is highly undesirable in malting barley crops. Pre-harvest sprouting is most often associated with rainfall and prolonged wet weather after full grain maturity. α-Amylase activity correlates with pre-germination and premature sprouting and can be used as indicator of sprout damage (Schwarz et al., 2004).

There is thus a need for barley plants having a high level of starch-degrading enzyme activity shortly after initiation of germination, but which never-the-less have grains with a high starch content, that produces a high yield and/or have low occurrence of pre-harvest sprouting.

The present invention provides barley plants having a high level of starch-degrading enzyme activity shortly after initiation of germination, in particular, said barley plants have high levels of α-amylase and limit dextrinase activity. Such barley plants are particularly useful for methods of production of cereal based beverages with reduced germination time.

One technical problem solved by the present invention is the provision of barley plants having a high α-amylase and limit dextrinase activity shortly after initiation of germination, for example already after 72 h or even as early as 48 h after initiation of germination, wherein the barley plants at the same time have acceptable agronomical traits. In one aspect the invention provides barley plants carrying a mutation in the HRT gene. The invention surprisingly demonstrates that barley plants having a loss of HRT function are viable, are agronomical sound and have yields comparable with other barley cultivars. At the same time such barley plants have high α-amylase and limit dextrinase activities already 48 h after initiation of germination. Another technical problem solved by the present invention is the provision of barley plants with sufficient germination even under conditions with reduced oxygen. Interestingly, barley plants having a loss of HRT function also solve this technical problem.

Raventos et al., 1998 have described that the full-length protein product of the barley gene HvREPRESSOR OF TRANSCRIPTION (HvHRT) acts as transcriptional repressor on a variety of different promoters when tested in plant cells after transient expression. Transient expression typically leads to expression levels, which are much higher than natural expression levels, and it is thus not possible to finally conclude the function of a protein using transient expression assays. In these artificial settings, transient expression of HRT lead to reduced expression of a reporter gene under control of different α-amylase promoters (Amy2 and Amy1), but also to reduced expression from the constitutive CaMV 35S promoter (Raventos et al. 1998). Thus, based on Raventos et al. HRT, a protein with three DNA binding domains, can bind and influence the expression from different promoter sequences. A mutant with a loss of HRT function could have aberrant transcription from numerous genes. Furthermore, Raventos et al. describes that HRT mRNA accumulates in immature tissues, for example in immature seeds, immature embryos and immature endosperm/aleurone. In contrast, HRT mRNA is barely detectable in layers from germinating seeds. On this basis, HRT could potentially be involved in securing that α-amylase is not expressed at time points in the development of barley, where high α-amylase activity is undesirable. High α-amylase activity during plant development is undesirable, because it may impair proper grain filling, may lead to reduced grain starch and result in pre-harvest sprouting. The present invention demonstrates that such barley mutants are never-the-less healthy and viable. Furthermore, even though Raventos et al. discloses that HRT mRNA is barely detectable on layers from germinating seeds, the present invention surprisingly shows that loss of HRT function leads to increased α-amylase activity in germinating seeds.

The effect of a loss-of-function mutation of a putative repressor is generally difficult to predict. First of all, it cannot be conclusively predicted, whether the repressor is in fact a repressor in in vivo settings based on transient expression studies. Furthermore, the mutation of a repressor may influence a plethora of genes, and thus the effect cannot be predicted. In addition, it can also not be predicted whether a mutation will in fact lead to increased expression of target genes. For example, KGM has been described to specifically repress alpha-amylase promoter activity at the level of GAMYB function upon transient transfection (Woodger et al., 2003). Never-the-less two different mutations in the gene encoding for KGM, one of which was a mutation introducing a premature stop codon did not result in increased α-amylase activity.

The present invention further describes the identification of the barley gene HBL12 (HomeoBoxLike12). The barley gene is also referred to as HvHBL12 herein. Mascher et al., 2017 described the sequencing of the barley genome. In addition, Mascher et al., 2017 provides a transcriptome of the barley model cv. Morex comprising a total of 123,875 corrected sequences. Based on this information, the inventors found that HvHBL12 is expressed in several tissues including the embryo tissue of germinating grain.

*Arabidopsis thaliana* comprises a gene with limited sequence identity to HvHBL12. Thus, the ATHB12 (*Arabidopsis thaliana* homeobox 12) gene of *Arabidopsis thaliana* has about 70% DNA sequence identity with HvHBL12. ATHB12 is a homeodomain-leucine zipper (HD-Zip) class I transcription factor discovered and studied in the model plant *Arabidopsis thaliana*. Valdés et al. (2012) reported that ATHB12 expression is induced by the hormone ABA. Son et al. (2010) reported that the gene product ATHB12 represses a gene of the GA biosynthetic pathway, the GA20oxidase 1 (GA20ox1) in *Arabidopsis* stems. *Arabidopsis thaliana* plants having a loss-of-function mutation of ATHB12 have a longer stem. Neither Valdés et al., 2012 nor Son et al., 2010 discusses a role for ATHB12 during early germination.

As noted above one technical problem solved by the present invention is the provision of barley plants having a high α-amylase and limit dextrinase activity shortly after initiation of germination, for example already after 72 h or even as early as 48 h after initiation of germination, wherein the barley plants at the same time have acceptable agronomical traits. In one aspect the invention provides barley plants carrying a mutation in the HvHBL12 gene. The invention surprisingly demonstrates that barley plants having a loss of HvHBL12 function are viable, are agronomical sound, have stems of a length comparable to wild type barley and have yields comparable with other barley cultivars. At the same time such barley plants have high α-amylase and limit dextrinase activities already 48 h after initiation of germination. Another technical problem solved by the present invention is the provision of barley plants having lower sensitivity for oxygen and hypoxic conditions during grain germination. Interestingly, barley plants having a loss of HvHBL12 function also solve this technical problem.

Zou et al., 2008 suggests that expression of Amy32b is modulated by protein complexes and that the relative amounts of repressor or activator complexes regulate expression. Zou et al., 2008 further suggests that HvWRKY38 and BPBF may act as transcriptional repressors. However, these suggestions are based on data from very artificial settings using a GUS reporter gene under control of an Amy32b promoter. Further, based on Zou et al., 2008 it is impossible to predict which relative amounts of repressor or activator will result in modulation of Amy32b expression. As noted above, the effect of a loss-of-function mutation of a putative repressor is generally difficult to predict.

As noted above one technical problem solved by the present invention is the provision of barley plants having a high α-amylase and limit dextrinase activity shortly after initiation of germination, wherein the barley plants at the same time have acceptable agronomical traits. In one aspect the invention provides barley plants carrying a mutation in the WRKY38 gene.

Thus, it is one aspect of the invention to provide barley plants or a part thereof with high α-amylase activity, wherein said barley plant.

carries a mutation in the HvHRT gene leading to loss of HvHRT function; and/or carries at least one α-amylase gene comprising a mutant α-amylase promoter comprising a mutation in the GARE box; and/or carries at least four α-amylase genes comprising a GARE box of the sequence TAACAAA; and/or carries at least one α-amylase gene in the amy2 cluster comprising a mutant α-amylase promoter comprising a mutation in the GARE box or which has the sequence TAACAAA; and/or carries a mutation in the HvHBL12 gene leading to loss of HvHBL12 function; and/or carries at least four α-amylase genes comprising an α-amylase promoter comprising a non-standard tandem repeat W-box, wherein said non-standard tandem repeat W-box comprises the sequence $(TGAC(C)_n(X)_m TTGACC)$ (SEQ ID NO: 38), wherein one or more of the specific nucleotides have been substituted or deleted, and wherein X may be any nucleotide, n is 0 or 1 and m is an integer in the range of 0 to 20; and/or carries at least one α-amylase gene in the amy2 cluster comprising an α-amylase promoter comprising a non-standard tandem repeat W-box;

carries a mutation in the WRKY38 gene leading to loss of WRKY38 function.

DESCRIPTION OF DRAWINGS

FIG. 11 shows an alignment of the parts of the α-amylase promoter containing the regulatory boxes from different α-amylase genes of the amy1_1 and amy1_2 clusters as well as from the amy1_1 of the HENZ-43 mutant (FIG. 11A), as well as from α-amylase genes of the amy2 cluster (FIG. 11B). The mutation of the HENZ-43 mutant is marked by #.

FIG. 13 shows α-amylase activity in barley grains germinating under submersion in water with an airflow of 9 L/h at 48 h and 72 h after start of germination. FIG. 13A shows the α-amylase activity of barley mutant HENZ-2 and control homozygous barley plants (WT) whereas

FIG. 15 upper panel shows the α-amylase activity of barley mutant HENZ-2a and wild type barley of cv. Planet, FIG. 15 middle panel shows α-amylase activity of barley mutant HENZ-54 and wild type barley of cv. Planet and FIG. 15 lower panel shows α-amylase activity of barley mutant HENZ-43 and wild type barley of cv. Planet.

FIG. 17 shows gene expression after 72 h of α-amylase mRNA encoded by α-amylase genes of the amy1_1 cluster as determined by RT ddPCR in germinating grains of barley mutant HENZ-2a and wild type barley of cv Planet (FIG. 17A), of barley mutant HENZ-54 and wild type barley of cv Planet (FIG. 17B) and of barley mutant HENZ-43 and wild type barley of cv Planet (FIG. 17C).

FIG. 20 shows gene expression after 72 h from the Bgl2 gene as determined by RT ddPCR in germinating grains of barley mutant HENZ-2a and wild type barley of cv Planet (FIG. 20A), of barley mutant HENZ-54 and wild type barley of cv Planet (FIG. 20B) and of barley mutant HENZ-43 and wild type barley of cv Planet (FIG. 20C).

DETAILED DESCRIPTION

Definitions

Figure 1:
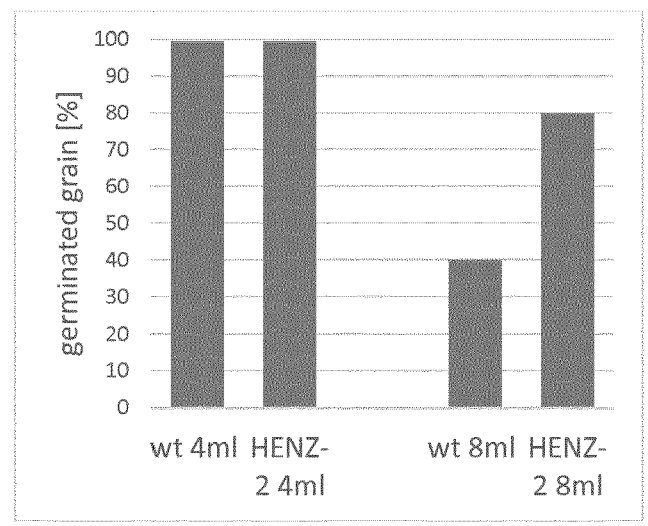
FIG. 1 shows % germinated grains of cv. Paustian (wt) and barley mutant HENZ-2 after standard germination test in the presence of either 4 ml (left columns) or 8 ml (right columns) of water.

As used herein, "a" can mean one or more, depending on the context in which it is used.

As used herein the term "α-amylase" refers to an enzyme having α-amylase activity. In particular, an α-amylase according to the invention is an enzyme capable of catalyzing endohydrolysis of (1→4)-α-D-glucosidic linkages in polysaccharides containing three or more (1→4)-α-linked D-glucose units. α-amylase activity may be determined by K-CERA 01/12 (protocol and kit available from Megazyme, Ireland).

The term "adjunct" as used herein refers to carbon-rich raw material sources added during preparation of beer. The adjunct may be an ungerminated cereal grain, which may be milled together with the germinated grains prepared according to the invention. The adjunct may also be a syrup, sugar or the like.

The term "approximately" when used herein in relation to numerical values preferably means ±10%, more preferably ±5%, yet more preferably ±1%.

The term "amino acid" as used herein refers to a proteinogenic amino acid. Preferably, the proteinogenic amino acids is one of the 20 amino acids encoded by the standard genetic code. The IUPAC one and three letter codes are used to name amino acids.

The term "amino acid corresponding to X" is used herein to describe amino acids of a given polypeptide (e.g. a mutant HRT, HBL12 or WRKY38 polypeptide) in relation to amino acids of a reference polypeptide (e.g. any of the polypeptides of SEQ ID NO:2, 6, 11 or 12). Following alignment between said polypeptide and the reference polypeptide, an amino acid is corresponding to X if it is in the same position as X in said alignment.

The term "amylose" refers to homopolymers of α-D-glucose. Amylose has a linear molecular structure, as its glucose units are almost exclusively linked by α-1-4-glycosidic bonds.

The term "amylopectin" refers to homopolymers of α-D-glucose. Amylopectin molecules contain frequent α-1-6-glycosidic linkages. These introduce branch points into the otherwise α-1-4-linked glucose chains resulting in clusters of parallel chains appearing in regular intervals along the molecule's axis.

The term "barley flour" as used herein refers to milled barley kernels.

The term β-amylase refers to an enzyme catalysing hydrolysis of (1→4)-alpha-D-glucosidic linkages in polysaccharides so as to remove successive maltose units from the non-reducing ends of the chains. β-amylase activity may be determined by the K-BETA3 (protocol and kit available from Megazyme, Ireland).

The term "chit" as used herein refers to the embryonic growing bud that is visible during the germination phase of a cereal grain.

As used herein the term "high yield" refers to a yield comparable to the yield of high yielding barley cultivars. In particular, a "high yield" may be a yield which is at least 95%, such as at least 98%, for example at least 100% of the yield of a barley plant of cv. Planet grown under the same conditions.

The term "barley" in reference to the process of making barley based beverages, such as beer, particularly when used to describe the malting process, means barley kernels. In all other cases, unless otherwise specified, "barley" means the barley plant (*Hordeum vulgare*, L.), including any breeding line or cultivar or variety, whereas part of a barley plant may be any part of a barley plant, for example any tissue or cells.

A "cereal" plant, as defined herein, is a member of the Poaceae plant family, cultivated primarily for their starch-containing seeds or kernels. Cereal plants include, but are not limited to barley (*Hordeum*), wheat (*Triticum*), rice (*Oryza*), maize (*Zea*), rye (*Secale*), oat (*Avena*), sorghum (Sorghum), and Triticale, a rye-wheat hybrid.

By "encoding" or "encoded", in the context of a specified nucleic acid, is meant comprising the information for translation into the specified protein. A nucleic acid or polynucleotide encoding a protein may comprise non-translated sequences, e.g. introns, within translated regions of the nucleic acid, or may lack such intervening non-translated sequences, e.g. in cDNA. The information by which a protein is encoded is specified by the use of codons.

As used herein, "expression" in the context of nucleic acids is to be understood as the transcription and accumulation of mRNA. "Expression" used in the context of proteins refers to translation of mRNA into a polypeptide.

The term "gene" means the segment of DNA involved in producing a polypeptide chain; it includes regions preceding and following the coding region (promoter and terminator). Furthermore, plant genes generally consist of exons interrupted by introns.

The term "initiation of germination" as used herein refers to the time point at which barley grains with a water content of less than 15% is contacted with sufficient water to initiate germination.

The term "malting" as used herein refers to a controlled germination of cereal kernels (in particular barley kernels) taking place under controlled environmental conditions. In some embodiments "malting" may further comprise a step of drying said germinated cereal kernels, e.g. by kiln drying.

The term "germinated grain" as used herein refers to a grain having developed a visible chit and a visible stem.

The term "green malt" as used herein refers germinated cereal kernels, which have not been subjected to a step of kiln drying. In general, said cereal kernels have been germinated under controlled environmental conditions. In some embodiments the green malt is milled green malt.

The term "kiln dried malt" as used herein refers germinated cereal kernels, which have been dried by kiln drying. In general, said cereal kernels have been germinated under controlled environmental conditions. In some embodiments the kiln dried malt is milled kiln dried malt.

The term "Limit dextrinase" as used herein refers to an enzyme capable of catalysing the hydrolysis of (1->6)-alpha-D-glucosidic linkages in alpha- and beta-limits dextrins of amylopectin and glycogen, in amylopectin and pullulan. In particular, a limit dextrinase may be an enzyme classified under EC 3.2.1.142. Limit-dextrinase activity is determined by the T-LDZ1000 (protocol and kit available from Megazyme, Ireland).

"Mashing" is the incubation of milled malt (e.g. green malt or kiln dried malt) and/or ungerminated cereal kernels in water. Mashing is preferably performed at specific temperature(s), and in a specific volume of water.

The term "milled" refers to material (e.g. barley kernels or malt), which has been finely divided, e.g. by cutting, milling, grinding or crushing. The barley kernels can be milled while moist using e.g. a grinder or a wet mill. Milled barley kernels or milled malt is sufficiently finely divided to render the material useful for aqueous extracts. Milled barley kernels or milled malt cannot be regenerated into an intact plant by essentially biological methods.

"Mutations" include deletions, insertions, substitutions, transversions, and point mutations in the coding and non-coding regions of a gene. Deletions may be of the entire gene, or of only a portion of the gene. Point mutations may concern changes of one base pair, and may result in premature stop codons, frameshift mutations, mutation of a splice site or amino acid substitutions. A gene comprising a mutation may be referred to as a "mutant gene". If said mutant gene encodes a polypeptide with a sequence different to the wild type, said polypeptide may be referred to as a "mutant polypeptide". A mutant polypeptide may be described as carrying a mutation, when it comprises an amino acid sequence differing from the wild type sequence. The nomenclature "XnnnY" indicates that amino acid or nucleotide X at position nnn has been replaced by Y. Thus, for example XnnnStop indicates that the codon encoding amino acid X at position nnn has been replaced by a stop codon.

By the term "plant product" is meant a product resulting from the processing of a plant or plant material. Said plant product may thus, for example, be green malt, kiln dried malt, wort, a fermented or non-fermented beverage, a food, or a feed product.

By the term "progeny" as used herein is meant a plant, which directly or indirectly is off-spring of a given plant. Thus, progeny is not confined to direct off-spring but also includes off-spring after numerous generations. In general, progeny of a barley plant carrying a specific mutation also carries that specific mutation.

The term "sequence identity" as used herein refers to the % of identical amino acids or nucleotides between a candidate sequence and a reference sequence following alignment. Thus, a candidate sequence sharing 80% amino acid identity with a reference sequence requires that, following alignment, 80% of the amino acids in the candidate sequence are identical to the corresponding amino acids in the reference sequence. Identity according to the present invention is determined by aid of computer analysis, such as, without limitations, the Clustal Omega computer alignment program for alignment of polypeptide sequences (Sievers et al. (2011 Oct. 11) *Molecular Systems Biology* 7:539, PMID: 21988835; Li et al. (2015 April 06) *Nucleic Acids Research* 43 (W1): W580-4 PMID: 25845596; McWilliam et al., (2013 May 13) *Nucleic Acids Research* 41 (Web Server issue): W597-600 PMID: 23671338, and the default parameters suggested therein. The Clustal Omega software is available from EMBL-EBI at ebi.ac.uk/Tools/msa/clustalo/. Using this program with its default settings, the mature (bioactive) part of a query and a reference polypeptide are aligned. The number of fully conserved residues are counted and divided by the length of the reference polypeptide. The MUSCLE or MAFFT algorithms may be used for alignment of nucleotide sequences. Sequence identities may be calculated in a similar way as indicated for amino acid sequences.

Sequence identity as provided herein is thus calculated over the entire length of the reference sequence.

The term "steeping" as used herein refers to the process of increasing the water content of a cereal kernel.

The term "starch" as used herein refers to a composition of one or both of the discrete macromolecules: amylose and amylopectin.

The term "splice site" as used herein refers to consensus sequences acting as splice signals for the splicing process. A splice site mutation is a genetic mutation that inserts, deletes or changes a number of nucleotides in the specific site at which splicing takes place during the splicing process, i.e. the processing of precursor messenger RNA into mature messenger RNA (mRNA). Splice site consensus sequences that drive exon recognition are typically located at the very termini of introns.

The term "stop codon" as used herein refers to a nucleotide triplet in the genetic code, which within mRNA results in termination of translation. The term "stop codon" as used herein also refers to a nucleotide triplet within a gene encoding the stop codon in mRNA. The stop codon in DNA typically has one of the following sequences: TAG, TAA or TGA.

The term "water content" of a grain as used herein refers to the % of $H_2O$ w/w in said grain.

Enzyme activities of cereal grains as used herein refer to the activities measured in flour prepared from the specified grain type. For example, 10 U/g of xx-amylase activity per gram cereal grain refers to said «x-amylase activity (10 U) measured in an aqueous extract derived from 1 g of flour (dry matter) from said cereal.

The volume of a gas as indicated herein refers to the volume of said gas at 1 atm and 20° C.

The volume of $O_2$ as indicated herein refers to the volume of $O_2$ at 1 atm and 20° C. In embodiments of the invention where $O_2$ is comprised in a mixture of gasses, then the total volume of the gas mixture may be determined, and the volume of $O_2$ may be calculated as the percentage of the total volume constituted by $O_2$. By way of example then atmospheric air comprises 21% $O_2$. Thus the volume of $O_2$ within atmospheric air as used herein is 21% of the total volume of atmospheric air.

By the term "wort" is meant a liquid extract of malt and/or cereal kernels, such as milled malt and/or milled cereal kernels and optionally additional adjuncts. Wort is in general obtained by mashing, optionally followed by "sparging", in a process of extracting residual sugars and other compounds from spent grains after mashing with hot water. Sparging is typically conducted in a lauter tun, a mash filter, or another apparatus to allow separation of the extracted water from spent grains. The wort obtained after mashing is generally referred to as "first wort", while the wort obtained after sparging is generally referred to as the "second wort". If not specified, the term wort may be first wort, second wort, or a combination of both. During conventional beer production, wort is boiled together with hops. Wort without hops, may also be referred to as "sweet wort", whereas wort boiled with hops may be referred to as "boiled wort" or simply as wort.

α-Amylase and Barley Plants Carrying a Mutation in an α-Amylase Promoter

The term α-amylase as used herein refers to an enzyme which is capable of catalyzing hydrolysis of alpha bonds within alpha-linked polysaccharides, such as starch. α-amylase is typically enzymes classified under EC 3.2.1.1. α-amylase is also known as alpha-amylase.

Cereal plants may comprise more than one gene encoding α-amylase. Accordingly, the barley plant according to the present invention may comprise more than one gene encoding α-amylase. Frequently, the genes encoding α-amylase may be organised in gene clusters.

An α-amylase according to the present invention may in particular be a polypeptide of a sequence with accession number HORVU6Hr1G078330.1, HORVU6Hr1G078360.1, HORVU6Hr1G078420.1, HORVU6Hr1G080790.1, HORVU7Hr1G091150.1, HORVU7Hr1G091240.1, or HORVU7Hr1G091250.3 or a functional homologue thereof sharing at least 90%, such as at least 95% sequence identity therewith, wherein said accession numbers are accession numbers from the barley genome sequencing project published by Mascher et al., 2017. The sequences are also available in the BARLEX database:

apex.ipk-gatersleben.de/apex/f?p=284:10.

Thus, the barley plant according to the invention may comprise at least 1, preferably at least 2, such as at least 3, for example 3 α-amylase gene clusters. In particular, the barley plant may comprise an amy1_1 cluster, an amy1_2 cluster and an amy2 cluster. The amy1_2 cluster frequently only comprises one gene, however for the sake of simplicity it is never-the-less referred to as the amy1_2 cluster herein. In addition to the aforementioned clusters, the barley plant may contain additional α-amylase genes/clusters (e.g. the amy 3, amy4_1 and amy4_2 genes). Each of these clusters may comprise one or more α-amylase genes.

Examples of sequences of α-amylase genes are available from the barley genome project published by Mascher et al., 2017:

| Mascher 2017 name | gene ID |
| --- | --- |
| amy1_1a | HORVU6Hr1G078330.1 |
| amy1_1b | HORVU6Hr1G078360.1 |
| amy1_1c | HORVU6Hr1G078420.1 |
| amy1_1d | HORVU0Hr1G032700.1 |
| amy1_1e | HORVU0Hr1G032850.5 |
| amy1_2 | HORVU6Hr1G080790.1 |
| amy2_1 | HORVU7Hr1G091150.1 |
| amy2_2 | HORVU7Hr1G091240.1 |
| amy2_3 | HORVU7Hr1G091250.3 |
| amy3 | HORVU5Hr1G068350.1 |
| amy4_1 | HORVU2Hr1G071710.5 |
| amy4_2 | HORVU3Hr1G067620.1 |

Each α-amylase gene in general comprises a promoter region (herein denoted α-amylase promoter), a coding region and one or more introns. As used herein the α-amylase promoter comprises or consists of the sequence of 1000 nucleotides, such as the 800 nucleotides immediately upstream of the start codon (ATG) of the coding sequence of the α-amylase gene. The exact sequences of the single gene copies within each cluster and in-between different barley cultivars may show significant differences in the α-amylase promoters, however certain regulatory boxes are conserved amongst multiple α-amylase genes. In particular, said regulatory boxes may be conserved amongst α-amylase genes of the amy1_1 cluster, the amy1_2 cluster and the amy2 cluster. FIG. 11 shows an alignment of the parts of the α-amylase promoter containing said regulatory boxes from different α-amylase genes of the amy1_1 and amy1_2 clusters (FIG. 11A), as well as from α-amylase genes of the amy2 cluster (FIG. 11B).

In particular, one or more of the α-amylase genes of the barley plants of the invention may comprise a GARE box with the sequence TAACARA, wherein R is G or A. This is in particular the case for α-amylase genes of the amy1_1 cluster, the amy1_2 cluster or the amy2 cluster. In general, each α-amylase promoter comprises at the most one GARE box. α-amylase genes of the amy3 and amy4 clusters frequently do not contain a GARE box.

In one embodiment of the invention it is preferred that the barley plant comprises one or more α-amylase genes comprising α-amylase promoters comprising a mutated GARE box. In other words, one or more α-amylase promoters may comprise no wild type GARE box, but instead a mutant GARE box, wherein one or more of the nucleotides TAACARA have been either substituted or deleted. Preferably, said mutant GARE box, is a GARE box wherein only one of the nucleotides TAACARA has been either substituted or deleted. In particular, the barley plant may comprise one or more α-amylase genes of the amy1_1 cluster, the amy1_2 cluster or the amy2 cluster comprising α-amylase promoters comprising a mutated GARE box.

In another embodiment it is preferred that the barley plant of the invention comprises one or more α-amylase gene, preferably at least 4, such as at least 5, for example at least 6 α-amylase genes, such as at least 7 α-amylase genes comprising α-amylase promoters comprising one GARE box with the sequence TAACAAA. In particular, said α-amylase genes may be α-amylase genes of the amy1_1 cluster, the amy1_2 cluster or the amy2 cluster. Said α-amylase gene may also contain a PYR box. The term "PYR box" as used herein refers to the sequence CMTTTT, wherein M is C or A.

Furthermore, one or more of the α-amylase genes of the barley plants of the invention may comprise a tandem repeat W-box. The standard tandem repeat W-box has the sequence (TGAC(C)$_n$(X)$_m$TTGACC) (SEQ ID NO: 38), wherein each X individually may be any nucleotide, n is 0 or 1 and m is an integer in the range of 0 to 20. It is understood that within any given tandem repeat W-box the individual Xs may be the same or different nucleotides. In general, each α-amylase promoter comprises only one tandem repeat W-box.

In one embodiment of the invention it is preferred that the barley plant comprises one or more α-amylase genes comprising α-amylase promoters comprising a non-standard tandem repeat W-box. In other words, one or more α-amylase promoters may comprise no standard tandem repeat W-box, but instead a non-standard tandem repeat W-box, wherein one or more of the nucleotides of the standard tandem repeat W-box (TGAC(C)$_n$(X)$_m$TTGACC) (SEQ ID NO: 38) have been either substituted or deleted. It is understood that said one or more nucleotides, which have been substituted or deleted are one or more of the specific nucleotides of the standard tandem repeat W-box (i.e. not any of the Xs).

In one embodiment the barley plant of the invention comprises one or more α-amylase genes, for example at least 4, such as at least 5, for example at least 6, such as at least 7 α-amylase genes comprising α-amylase promoters comprising a non-standard tandem repeat W-box individually selected from the group consisting of the following sequences:
  (TGACR(X)$_m$YTGRCC) (SEQ ID NO: 39), wherein R is either G or A and Y is either C or T and m is an integer in the range of 0 to 20; or
  (TGACR(X)$_m$TTGACC) (SEQ ID NO:40), wherein R is either G or A and m is an integer in the range of 0 to 20; or
  (TGACR(X)$_m$TTGAC) (SEQ ID NO:41), wherein R is either G or A and m is an integer in the range of 0 to 20; or
  (TGAC(C)$_n$(X)$_m$YTGRCC) (SEQ ID NO: 42), wherein R is either G or A and Y is either C or T, n is 0 or 1 and m is an integer in the range of 0 to 20; or
  (TGAC(C)$_n$(X)$_m$CTGRCC) (SEQ ID NO: 43), wherein R is either G or A, n is 0 or 1 and m is an integer in the range of 0 to 20;
  (TGAC(C)$_n$(X)$_m$YTGGCC) (SEQ ID NO: 44), and wherein Y is either C or T, n is 0 or 1 and m is an integer in the range of 0 to 20; or
  (TGAC(C)$_n$(X)$_m$CTGACC) (SEQ ID NO: 45), wherein n is 0 or 1 and m is an integer in the range of 0 to 20;
  (TGAC(C)$_n$(X)$_m$TTGGCC) (SEQ ID NO: 46), wherein n is 0 or 1 and m is an integer in the range of 0 to 20
  (TGAC(C)$_n$(X)$_m$TTGATC) (SEQ ID NO: 47), wherein N IS 0 OR 1 and m is an integer in the range of 0 to 20; or.

As mentioned above, m may be an integer in the range of 0 to 20, preferably m is an integer in the range of 0 to 10, even more preferably m is an integer in the range of 0 to 6.

In one embodiment the barley plant of the invention comprises one or more α-amylase genes, for example at least 5 α-amylase genes comprising α-amylase promoters comprising a non-standard tandem repeat W-box individually selected from non-standard tandem repeat W-boxes of the following sequences:

TGACGGTCGTATTGACC; (SEQ ID NO: 31)

TGACAGTGGTATTGGCC; (SEQ ID NO: 32)

TGACAGTGGTACTGGCC; (SEQ ID NO: 33)

GTGACAGTGGTATTGGCC; (SEQ ID NO: 34)

TGACGGTCGTATTGATC; (SEQ ID NO: 35)

TGACCGTCGTATTGATC; (SEQ ID NO: 36)
and

TTGACTTGATC. (SEQ ID NO: 37)

Database searches and promoter re-sequencing provided herein demonstrates that α-amylase promoters of the α-amylase genes of the amy1_1, amy1_2 and amy2 clusters comprise GARE box sequences. In particular, the α-amylase genes of the amy2 cluster in wild type barley comprise a GARE box of the sequence TAACAGA.

The amy1_1 cluster may comprise 1 to 5 α-amylase genes, however not all α-amylase genes are necessarily expressed. Thus, in some barley plants (e.g. in cv. Barke or progeny thereof) the amy1_1 cluster comprises at least three major copies, whereas other barley plants (e.g. cv. Planet or progeny thereof) may comprise three α-amylase genes in the amy1_1 cluster of which only two might be expressed. For example some α-amylase promoter lack the PYR box and are therefore believed not to be expressed. An α-amylase according to the invention may be an α-amylase encoded by a gene of the amy1_1 cluster. For example, the α-amylase may be a polypeptide with the sequence with accession number AAA98790.1 or BAK03603.1 or a functional homologue thereof sharing at least 90%, such as at least 95% sequence identity therewith, wherein said accession numbers are accession numbers of the NCBI database. The α-amylase may also be polypeptide having a sequence with accession number HORVU6Hr1G078330.1, HORVU6Hr1G078360.1, HORVU6Hr1G078420.1, HORVUOHr1G032700.1, or HORVUOHr1G032850.5 or a functional homologue thereof sharing at least 90%, such as at least 95% sequence identity therewith, wherein said accession numbers are accession numbers of the BARLEX database (apex.ipk-gatersleben.de/apex/f?p=284:10) and published by Mascher et al., 2017.

The barley plant of the invention comprises an amy1_1 cluster, wherein at least one of the α-amylase promoters, preferably all of the α-amylase promoters comprises:
  only a mutated GARE box, wherein one of the nucleotides of the GARE box (TAACARA) have been either substituted or deleted; and/or
  a GARE box with the sequence TAACAAA.; and/or
  only a non-standard tandem repeat W-box, wherein one or more of the specific nucleotides of the standard tandem repeat W-box (TGAC(C)$_n$(X)$_m$TTGACC) (SEQ ID NO: 38) have been either substituted or deleted, for example said non-standard tandem repeat W-box may have any of non-standard tandem repeat W-box sequences described herein above. In addition said α-amylase promoters may comprise a PYR box.

The term "only a mutated GARE box" as used herein refers to said promoter comprising only one GARE box, wherein said GARE box is mutated, i.e. that said promoter does not contain a wild type GARE box in addition to said mutated GARE box. Similarly, the term "only a non-standard tandem repeat W-box" as used herein refers to said promoter comprising only one tandem repeat W-box, wherein said tandem repeat W-box is a non-standard tandem repeat W-box, i.e. that said promoter does not contain a standard tandem repeat W-box in addition to said non-standard tandem repeat W-box.

As shown by the present invention, a GARE box with the sequence TAACAAA has lower HRT binding compared to a GARE box with the sequence TAACAGA. Similarly, it is believed that WRKY38 has lower binding to a non-standard tandem repeat W-box than to the standard tandem repeat W-box. In a world panel of 96 malting barleys (2-row spring barley, 2-row winter-barley, 6-row winter barley), six unique amy1_1 clusters can be found. Out of this panel, barleys with the highest α-amylase activity have always a amy1_1 cluster comprising at least three α-amylase genes comprising an α-amylase promoter comprising a GARE box with the sequence TAACAAA.

Unfortunately, the barley plants with the highest α-amylase activity tested in the panel did not have the highest yield. In one embodiment, the present invention provides barley plants with both high yields and high α-amylase activity.

In one embodiment, the barley plant comprises an amy1_1 cluster, wherein at least one of the α-amylase promoters comprises a non-standard tandem repeat W-box comprising the sequence TTGATC. For example, the barley plant may comprise an amy1_1 cluster, wherein at least one of the α-amylase promoters comprises a non-standard tandem repeat W-box comprising the sequence CIGACGGTCGTATTGATC (SEQ ID NO 72). In particular, the barley plant may comprise an α-amylase promoter comprising the sequence shown as "HENZ-43 amy1_1" in FIG. 11A. Said barley plant may for example be HENZ-43 or progeny thereof. For example, the barley plant may be a barley plant identified as described in Example 13A or progeny thereof.

The amy1_2 cluster in general comprises only a single α-amylase gene. The amy1_2 cluster is typically closely linked to the amy1_1 cluster in the barley genome. An α-amylase according to the invention may be an α-amylase encoded by a gene of the amy1_2 cluster. For example, the α-amylase may be polypeptide having a sequence with accession number AAA98615.1 or a functional homologue thereof sharing at least 90%, such as at least 95% sequence identity therewith, wherein said accession numbers are accession numbers of the NCBI database. The α-amylase may also be polypeptide having a sequence with accession number HORVU6Hr1G080790.1 or a functional homologue thereof sharing at least 90%, such as at least 95% sequence identity therewith, wherein said accession numbers are accession numbers of the BARLEX database (apex.ipk-gatersleben.de/apex/f?p=284:10) and described in Mascher et al., 2017.

Frequently, the α-amylase gene of the amy1_2 cluster comprises an α-amylase promoter comprising a GARE box of the sequence TAACAAA. The barley plant of the invention may comprise an amy1_2 cluster, comprising an α-amylase with an α-amylase promoter comprising:

only a mutated GARE box, wherein one of the nucleotides of the GARE box (TAACARA) have been either substituted or deleted; and/or
a GARE box with the sequence TAACAAA.; and/or
only a non-standard tandem repeat W-box, wherein one or more of the specific nucleotides of the standard tandem repeat W-box (TGAC(C)$_n$(X)$_m$TTGACC) (SEQ ID NO: 38) have been either substituted or deleted, for example said non-standard tandem repeat W-box may have any of non-standard tandem repeat W-box sequences described herein above.

The amy2 cluster may consist of three expressed copies of the α-amylase gene. This is for example the case in cv. Morex. In wild type barley each α-amylase gene of the amy2 cluster may comprise a GARE box of the sequence TAACAGA.

An α-amylase according to the invention may be an α-amylase encoded by a gene of the amy2 cluster. For example, the α-amylase may be polypeptide having a sequence with accession number HORVU7Hr1G091150.1, HORVU7Hr1G091240.1, HORVU7Hr1G091250.3 or a functional homologue thereof sharing at least 85%, such as at least 90% sequence identity therewith, wherein said accession numbers are accession numbers of the BARLEX database (apex.ipk-gatersleben.de/apex/f?p=284:10) and described in Mascher et al., 2017).

In contrast, the barley plants of the invention may comprise an amy2 cluster comprising one or more α-amylase genes with α-amylase promoters comprising:

only a mutated GARE box, wherein one or more of the nucleotides TAACARA have been either substituted or deleted,
a GARE box with the sequence TAACAAA,
only a non-standard tandem repeat W-box, wherein one or more of the specific nucleotides of the standard tandem repeat W-box (TGAC(C)$_n$(X)$_m$TTGACC) (SEQ ID NO: 38) have been either substituted or deleted, for example said non-standard tandem repeat W-box may have any of non-standard tandem repeat W-box sequences described herein above.

In particular, the barley plant may comprise an amy2 cluster comprising one or more α-amylase genes with α-amylase promoters comprising a mutated tandem repeat W-box comprising the sequence TTGACTTGACC wherein at least one nucleotide has been substituted or deleted.
HRT The full-length protein product of the barley gene HvRE-PRESSOR OF TRANSCRIPTION (HvHRT) acts as transcriptional repressor on a variety of different promoters when tested in plant cells after transient expression. In these very artificial settings, transient expression of HRT leads to reduced expression of a reporter gene under control of different α-amylase promoters (Amy2 and Amy1), but also to reduced expression from the constitutive CaMV 35S promoter. The repression of the Amy2 promoter was found to be stronger in this system (Raventos et al. 1998). HRT binds to and blocks the so-called "GARE (GA responsive element) box", which is also the binding site of the putative activator of α-amylase gene expression, HvGAMyb (Gubler et al. 1995).

The wild type coding sequence of barley HRT is provided herein as SEQ ID NO:1. Multiple sequence alignment of HvHRT CDS sequences AK362734.1 (cv. Haruna Nijo). AK252040.1 (Haruna Nijo), HORVU2Hr1G035630.1 (cv. Morex), AJ001317.1 (Himalaya), and manually assembled sequences for cvs. Bowman and Barke derived from genomic DNA contigs in IBSC2012 (available in the BAR- LEX database (apex.ipk-gatersleben.de/apex/f?p=284:10) demonstrated 100% sequence identity between the CDS sequences. The protein sequence of wild type barley HRT is provided herein as SEQ ID NO:2. Multiple sequence alignment of HvHRT protein sequences AK362734.1 (cv. Haruna Nijo), AK252040.1 (Haruna Nijo), HORVU2Hr1G035630.1 (cv. Morex), AJ001317.1/CAA04677.1 (Himalaya), and manually assembled and translated sequences for cvs. Bowman and Barke derived from genomic DNA contigs in IBSC2012 demonstrated 100% sequence identity between the protein sequences. The HvHRT protein contains two putative nuclear localization sites (NLS). Thus, amino acids 276 to 292 of SEQ ID NO:2 (Arg276-Arg292), and amino acids 527 to 530 of SEQ ID NO:2 (Arg527-Arg530) constitute putative NLS (Raventos et al., 1998). Furthermore, HvHRT contains three putative DNA-binding domains reminiscent of zinc fingers (herein also referred to HRTdb), containing the following consensus sequence:

$VCG_{X4}DG_{X2}C_{X2}C_{X3}PV_{X2}RKRC_{X2}HKG_{X}R$ (SEQ ID NO: 99), wherein X may be any amino acid. Thus amino acids 302 to 331 of SEQ ID NO:2, amino acids 463 to 491 of SEQ ID NO:2 and amino acids 509 to 539 of SEQ ID NO:2 constitute putative DNA binding domains.

Barley Plant Carrying a Mutation in the HRT Gene

In one embodiment the present invention provides a barley plant carrying a mutation in the HRT gene leading to a loss of HRT function, and in particular to a total loss of HRT function. Loss of HRT function may be determined by determining the expression level of HRT either on the mRNA level or on the protein level. In one embodiment, a barley plant is considered to have a loss of HRT function when the barley plant comprises less than 50%, preferably less than 25%, and even more preferably less than 10% mutant or wild type HvHRT mRNA compared to the level of HvHRT mRNA in a barley plant comprising a wild type HvHRT gene, but otherwise of the same genotype. A barley plant may be considered to have a total loss of HRT function when the barley plant comprises less than 5%, preferably less than 1% mutant or wild type HvHRT mRNA compared to a barley plant comprising a wild type HvHRT gene, but otherwise of the same genotype. Said mutant HvHRT is mRNA encoded by a mutated HvHRT gene carrying a mutation in the mRNA coding region. HvHRT mRNA is RNA encoding a polypeptide of SEQ ID NO:2 or a functional homologue thereof, and a wild type HvHRT gene is a gene encoding the polypeptide of SEQ ID NO:2 or a functional homologue thereof. Said functional homologue preferably shares at least 95% sequence identity with SEQ ID NO:2. In one embodiment a barley plant with total loss of HRT function may contain no detectable mutant or wild type HvHRT mRNA, when determined by conventional quantitative RT-PCR.

In one embodiment, a barley plant is considered to have a loss of HRT function when the barley plant comprises less than 50%, preferably less than 25%, and even more preferably less than 10% mutant or wild type HvHRT protein compared to the level of HvHRT protein in a barley plant comprising a wild type HvHRT gene, but otherwise of the same genotype. A barley plant may be considered to have a total loss of HRT function when the barley plant comprises less than 5%, preferably less than 1% mutant or wild type HvHRT protein compared to a barley plant comprising a wild type HvHRT gene, but otherwise of the same genotype. Said mutant HvHRT protein is a polypeptide encoded by a mutated HvHRT gene carrying a mutation in the coding region. HvHRT protein is a polypeptide of SEQ ID NO:2 or a functional homologue thereof, and a wild type HvHRT gene is a gene encoding the polypeptide of SEQ ID NO: 2 or a functional homologue thereof. Said functional homologue preferably shares at least 95% sequence identity with SEQ ID NO:2. In one embodiment a barley plant with total loss of HRT function may contain no detectable mutant or wild type HvHRT protein as detected by conventional Western blotting.

In one embodiment, a barley plant is considered to have a loss of HRT function when an increased expression from a promoter comprising a GARE box can be observed. Thus, loss of HRT function may be determined by transient transfection of a reporter construct comprising a reporter gene (e.g. luciferase) under the control of an α-amylase promoter from the Amy2 cluster, for example the construct described in Raventos et al., 1998 on p. 23314 in the section "*Transient Gene Expression Assays in Onion Epidermal and Barley Aleurone Cells*". An increase in luciferase activity of at least 10%, such as at least 25% after transfection of said reporter construct to a given barley plant compared to transfection of said reporter construct to a barley plant with a wild type HvHRT gene, but otherwise of the same genotype, is indicative of said barley plant having a loss of HRT function.

In one embodiment, a barley plant is considered to have a loss of HRT function if said barley plant carries a mutation resulting in an HRT gene encoding a mutant HvHRT protein lacking one or more of the following domains:

NLS1: R276-R292 of SEQ ID NO:2
NLS2: R527-R530 of SEQ ID NO:2
HRTdb1: V302-R331 of SEQ ID NO:2
HRTdb2: L463-E491 of SEQ ID NO:2
HRTdb3: V509-A539 of SEQ ID NO:2

The barley plant carrying a mutation in the HRT gene leading to a loss of HRT function may carry different types of mutations, e.g. any of the mutations described herein in this section.

In one embodiment the barley plant carries a mutation in the promoter region of the HvHRT gene or in an intron of the HvHRT gene leading to aberrant transcription of HvHRT mRNA and/or aberrant translation of HvHRT protein. Such barley plants may in particular have reduced HvHRT mRNA levels as described herein above in this section and/or reduced HvHRT protein levels as described herein above in this section.

In one embodiment the barley plant of the invention carries a mutation resulting in deletion of the HvHRT gene. The genomic sequence of the HvHRT gene differs amongst different barley varieties; however the coding region is highly conserved. Examples of genomic sequences of the HvHRT barley gene includes the sequence with accession number ID #AJ001317.1 in NCBI. Furthermore, the majority of the genome sequence of the HvHRT gene can be found in morex_contig_368180 and morex_contig_1570244 (cv. Morex) (IBSC, 2012), however these contigs are not overlapping and part of the intron sequence is missing. The coding sequence of HRT of several wild type barley plants is provided herein as SEQ ID NO:1.

In one embodiment, the barley plant of the invention carries a mutation resulting in a mutant HvHRT gene encoding a mutant HvHRT protein. In one embodiment the mutation may be a mutation resulting in formation of a premature stop codon. In another embodiment the mutation is a mutation in a splice site of the HvHRT gene. Said mutation may lead to aberrant splicing of HvHRT mRNA.

In one embodiment, the barley plant of the invention carries a mutation resulting in a mutant HvHRT gene encoding a mutant HvHRT protein lacking at least the amino acids corresponding to amino acids 527 to 530 of SEQ ID NO:2. It is understood that a mutant HvHRT lacking at least amino acids XX to YY may lack other amino acids in addition to amino acids XX to YY.

In one embodiment, the barley plant may comprise a mutant HvHRT gene encoding a mutant HvHRT protein lacking at least amino acids 463 to 491 of SEQ ID NO:2, for example said a mutant HvHRT protein may lack at least amino acids 463 to 491 and amino acids 527 to 530 of SEQ ID NO:2.

In one embodiment, the barley plant may comprise a mutant HvHRT gene encoding a mutant HvHRT protein lacking at least amino acids 509 to 539 of SEQ ID NO:2.

In one embodiment the barley plant of the invention may comprise a mutant HvHRT gene encoding a mutant HvHRT protein lacking at least the 21 most C-terminal amino acids, for example at least the 39 most C-terminal amino acids, such as at least the 85 most C-terminal amino acids, for example at least the 100 most C-terminal amino acids of SEQ ID NO:2. For example, the barley plant may comprise a mutant HvHRT gene encoding a mutant HvHRT protein lacking at least the 118 most C-terminal amino acids of SEQ ID NO:2.

In one embodiment the barley plant of the invention may comprises a mutant HvHRT gene encoding a truncated HvHRT protein comprising an N-terminal fragment of HvHRT comprising at the most the 526 N-terminal amino acids of SEQ ID NO:2, for example at the most the 508 N-terminal amino acids of SEQ ID NO:2, such as at the most the 462 N-terminal amino acids of SEQ ID NO:2, preferably at the most the 431 N-terminal amino acids of SEQ ID NO:2.

In one embodiment, the barley plant of the invention may comprises a mutant HvHRT gene carrying a premature stop codon in any one of codons 1 to 527, for example in any one of codons, 1 to 509, such as in any one of codons 1 to 463, for example in any one of codons 1 to 431. For example, the barley plant may comprise a mutant HvHRT gene carrying a premature stop codon in codon 431. Codons are numbered according to SEQ ID NO: 1 starting at the 5' end, wherein 3 nucleotides constitutes one codon.

In one embodiment the barley plant of the invention comprises a mutant HvHRT gene encoding a mutant HvHRT protein having a W431stop mutation of SEQ ID NO: 2. In one preferred embodiment, the barley plant of the invention comprises a mutant HvHRT gene encoding the polypeptide of SEQ ID NO:4. In particular said barley plant may comprise a G→A mutation of the nucleotide 1293 of the HvHRT coding sequence of SEQ ID NO:1. For example, the barley plant may comprise a mutant HvHRT gene comprising the coding sequence of SEQ ID NO:3.

In one embodiment the barley plant of the invention comprises a mutant HvHRT gene encoding a mutant HvHRT protein having a W170stop mutation of SEQ ID NO: 2. For example, the barley plant may comprise a mutant HvHRT gene carrying a premature stop codon in codon 170 (codon numbering in relation to SEQ ID NO:1 as explained above). In particular said barley plant may comprise a G-A mutation of the nucleotide 510 of the HvHRT coding sequence of SEQ ID NO:1. Said barley plant may for example be HENZ-53 or progeny thereof. For example, the barley plant may be a barley plant identified as described in Example 14 or progeny thereof.

In one embodiment the barley plant of the invention comprises a mutant HvHRT gene encoding a mutant HvHRT protein having a W371stop mutation of SEQ ID NO: 2. For example, the barley plant may comprise a mutant HvHRT gene carrying a premature stop codon in codon 371 (codon numbering in relation to SEQ ID NO:1 as explained above). In particular said barley plant may comprise a G→A mutation of the nucleotide 1113 of the HvHRT coding sequence of SEQ ID NO:1. Said barley plant may for example be HENZ-54 or progeny thereof. For example, the barley plant may be a barley plant identified as described in Example 14 or progeny thereof.

For the purposes of this patent application seeds of barley plant (*Hordeum vulgare*) designated "HENZ-2" has been deposited with NCIMB Ltd. Ferguson Building, Craibstone Estate, Bucksburn, Aberdeen, AB21 9YA Scotland under the provisions of the Budapest Treaty. The HENZ-2 barley plant was deposited on 12 Nov. 2018 and has received the accession number NCIMB 43270.

In one embodiment, the barley plant of the invention is the barley plant (*Hordeum vulgare*) deposited on 12 Nov. 2018 with NCIMB under the accession number NCIMB 43270 and referred to as "HENZ-2"; or progeny thereof. Thus, the barley plant of the invention may be barley plant HENZ-2 deposited with NCIMB on 12 Nov. 2018 and having accession number NCIMB 43270 or any progeny barley plant thereof, wherein the progeny barley plant carries a G→A mutation of nucleotide 1293 of the HvHRT coding sequence of SEQ ID NO:1 and/or wherein the HvHRT gene of said barley plant encodes a mutant HvHRT protein comprising a W431stop mutation of SEQ ID NO: 2.

HvHBL12

The barley gene HvHBL12 has not been described previously. The coding sequence of a HvHBL12 gene from barley cultivar Haruna Nijo is provided herein as SEQ ID NO: 5. The sequence of the HvHBL12 protein encoded by this sequence is provided herein as SEQ ID NO:6. An additional coding sequence is available from Haruna Nijo, however this sequence carries a stop codon at codon 216. The inventors believe this to be a non-functional copy. Two sequences of HvHBL12 have been deposited in the NCBI database under the accession numbers AK376953.1 and AK361212.1. The sequences encodes proteins with various polymorphisms compared to SEQ ID NO:6 including the following: N141D, M142V and E184D. The polypeptide of SEQ ID NO:6, as well as polypeptides of SEQ ID NO:6 with any of the polymorphisms N141D, M142V and E184D are all considered wild type HvHBL12 proteins herein.

The genomic sequence of the HvHBL12 gene may differ amongst different barley varieties. Examples of genomic sequences of the HvHBL12 barley gene is found on morex_contig_56855 (cv. Morex) (IBSC, 2012), and the sequences with accession number AK376953.1 and AK361212.1 in the NCBI database (partial sequences). However, the start of the coding sequence indicated in the NCBI database is probably incorrect. The coding sequence of the HvHBL12 gene also differs somewhat between different barley varieties. Preferably, the coding sequence of a functional HvHBL12 gene has the sequence provided herein as SEQ ID NO:5 or a sequence sharing at least 90%, preferably at least 95% sequence identity thereto, wherein said sequence encodes the polypeptide of SEQ ID NO:6 or a functional homologue thereof sharing at least 95% sequence identity thereto. Examples of coding sequences of the HvHBL12 gene in barley includes the sequence provided herein as SEQ ID NO:5, or the sequence with accession number HORVU5Hr1G081090.1 (Mascher et al., 2017).

A protein sequence blast using the HvHBL12 protein sequence shows that HvHBL12 has some homology with homeobox-leucine zipper proteins.

Amino acids 26 to 79 of SEQ ID NO:6 constitute a putative homeobox domain, whereas amino acids 81 to 122 of SEQ ID NO:6 constitute a putative homeobox associated leucine zipper.

Barley Plant Carrying a Mutation in the HvHBL12 Gene

In one embodiment the present invention provides a barley plant carrying a mutation in the HvHBL12 gene leading to a loss of HvHBL12 function, and in particular to a total loss of HvHBL12 function. Loss of HvHBL12 function may be determined by determining the expression level of HvHBL12 either on the mRNA level or on the protein level. In one embodiment, a barley plant is considered to have a loss of HvHBL12 function when the barley plant comprises less than 50%, preferably less than 25%, and even more preferably less than 10% mutant or wild type HvHBL12 mRNA compared to the level of HvHBL12 mRNA in a barley plant comprising a wild type HvHBL12 gene, but otherwise of the same genotype. A barley plant may be considered to have a total loss of HvHBL12 function when the barley plant comprises less than 5%, preferably less than 1% mutant or wild type HvHBL 12 mRNA compared to a barley plant comprising a wild type HvHBL12 gene, but otherwise of the same genotype. Said mutant HvHBL12 is mRNA encoded by a mutated HvHBL12 gene carrying a mutation in the mRNA coding region. HvHBL12 mRNA is RNA encoding a polypeptide of SEQ ID NO:6 or a functional homologue thereof, and a wild type HvHBL12 gene is a gene encoding the polypeptide of SEQ ID NO:6 or a functional homologue thereof. Said functional homologue preferably shares at least 95% sequence identity with SEQ ID NO:6. In one embodiment a barley plant with total loss of HvHBL 12 function may contain no detectable mutant or wild type HvHBL12 mRNA, when determined by conventional quantitative RT-PCR.

In one embodiment, a barley plant is considered to have a loss of HvHBL12 function when the barley plant comprises less than 50%, preferably less than 25%, and even more preferably less than 10% mutant or wild type HvHBL12 protein compared to the level of HvHBL 12 protein in a barley plant comprising a wild type HvHBL12 gene, but otherwise of the same genotype. A barley plant may be considered to have a total loss of HvHBL 12 function when the barley plant comprises less than 5%, preferably less than 1% mutant or wild type HvHBL12 protein compared to a barley plant comprising a wild type HvHBL12 gene, but otherwise of the same genotype. Said mutant HvHBL12 protein is a polypeptide encoded by a mutated HvHBL12 gene carrying a mutation in the coding region. HvHBL 12 protein is a polypeptide of SEQ ID NO: 6 or a functional homologue thereof, and a wild type HvHBL12 gene is a gene encoding the polypeptide of SEQ ID NO:6 or a functional homologue thereof. Said functional homologue preferably shares at least 95% sequence identity with SEQ ID NO: 6. In one embodiment a barley plant with total loss of HvHBL 12 function may contain no detectable mutant or wild type HvHBL12 protein as detected by conventional Western blotting.

In one embodiment, a barley plant is considered to have a loss of HvHBL12 function if said barley plant carry a mutation resulting in an HvHBL12 gene encoding a mutant HvHBL 12 protein lacking one or more of the following domains:

Homeobox domain: amino acid 26 to 79 of SEQ ID NO:6
Homeobox associated leucine zipper: amino acids 81 to 122 of SEQ ID NO:6
C-terminal part: amino acids 228 to 250 of SEQ ID NO:6

The barley plant carrying a mutation in the HvHBL 12 gene leading to a loss of HvHBL12 function may carry different types of mutations, e.g. any of the mutations described herein in this section.

In one embodiment the barley plant carries a mutation in the promoter region of the HvHBL 12 gene or in an intron of the HvHBL12 gene leading to aberrant transcription of HvHBL12 mRNA and/or aberrant translation of HvHBL12 protein. Such barley plants may in particular have reduced HvHBL12 mRNA levels as described herein above in this section and/or reduced HvHBL12 protein levels as described herein above in this section.

In one embodiment the barley plant of the invention carries a mutation resulting in deletion of the HvHBL12 gene.

In one embodiment, the barley plant of the invention carries a mutation resulting in a mutant HvHBL12 gene encoding a mutant HvHBL12 protein. In one embodiment the mutation may be a mutation resulting in formation of a premature stop codon. In another embodiment the mutation is a mutation in a splice site of the HvHBL12 gene. Said mutation may lead to aberrant splicing of HvHBL12 mRNA.

In one embodiment, the barley plant of the invention carries a mutation resulting in a mutant HvHBL12 gene encoding a mutant HvHBL12 protein lacking one or more amino acids of SEQ ID NO:6 or a functional homologue thereof sharing at least 95% sequence identity thereto.

In one embodiment, the barley plant may comprise a mutant HvHBL12 gene encoding a mutant HvHBL 12 protein lacking at least amino acids 26 to 79 of SEQ ID NO:6 or of SEQ ID NO:6 carrying one or more of the polymorphism N141D, M142V or E184D; or amino acids 81 to 122 of SEQ ID NO:6 or of SEQ ID NO:6 carrying one or more of the polymorphism N141D, M142V or E184D; or amino acids 228 to 250 of SEQ ID NO:6 or of SEQ ID NO:6 carrying one or more of the polymorphism N141D, M142V or E184D.

It is understood that a mutant HvHBL12 lacking at least amino acids XX to YY may lack other amino acids in addition to amino acids XX to YY.

In one embodiment the barley plant of the invention may comprise a mutant HvHBL12 gene encoding a mutant HvHBL12 protein lacking at least the 5 most C-terminal amino acids, for example at least the 10 most C-terminal amino acids, such as at least the 15 most C-terminal amino acids, for example at least the 20 most C-terminal amino acids of SEQ ID NO:6 or a functional homologue thereof sharing at least 95% sequence identity thereto. For example, the barley plant may comprise a mutant HvHBL12 gene encoding a mutant HvHBL12 protein lacking at least the 22 most C-terminal amino acids of SEQ ID NO:6 or a functional homologue thereof sharing at least 95% sequence identity thereto.

In one embodiment the barley plant of the invention may comprises a mutant HvHBL12 gene encoding a truncated HvHBL 12 protein comprising an N-terminal fragment of HvHBL12 comprising at the most the 245 N-terminal amino acids of SEQ ID NO: 6 or a functional homologue thereof sharing at least 95% sequence identity thereto, for example at the most the 240 N-terminal amino acids of SEQ ID NO:6 or a functional homologue thereof sharing at least 95% sequence identity thereto, such as at the most the 235 N-terminal amino acids of SEQ ID NO:6 or a functional homologue thereof sharing at least 95% sequence identity thereto, preferably at the most the 227 N-terminal amino acids of SEQ ID NO:6 or a functional homologue thereof sharing at least 95% sequence identity thereto.

In one embodiment, the barley plant of the invention may comprises a mutant HvHBL 12 gene carrying a premature stop codon in any one of codons 1 to 245, for example in any one of codons, 1 to 240, such as in any one of codons 1 to 235, for example in any one of codons 1 to 228. For example, the barley plant may comprise a mutant HvHBL12 gene carrying a premature stop codon in codon 228. Codons are numbered according to SEQ ID NO:5 starting at the 5' end, wherein 3 nucleotides constitutes one codon.

In one embodiment the barley plant of the invention comprises a mutant HvHBL12 gene encoding a mutant HvHRT protein having a W228stop mutation of SEQ ID NO: 6. In one preferred embodiment, the barley plant of the invention comprises a mutant HvHBL12 gene encoding the polypeptide of SEQ ID NO:9 or of SEQ ID NO:9 carrying one or more of the polymorphism N141D, M142V or E184D. In particular said barley plant may comprise a G→A mutation of the nucleotide 684 of the HvHBL12 coding sequence of SEQ ID NO:5. For example, the barley plant may comprise a mutant HvHBL12 gene comprising the coding sequence of SEQ ID NO:8.

The functional homologue may of SEQ ID NO:6 referred to in this section may in particular be SEQ ID NO:6 carrying one or more of the following polymorphisms: N141D, M142V and E184.

For the purposes of this patent application seeds of barley plant (*Hordeum vulgare*) designated "HENZ-10" has been deposited with NCIMB Ltd. Ferguson Building, Craibstone Estate, Bucksburn, Aberdeen, AB21 9YA Scotland under the provisions of the Budapest Treaty. The HENZ-10 barley plant was deposited on 12 Nov. 2018 and has received the accession number NCIMB 43271.

In one embodiment, the barley plant of the invention is the barley plant (*Hordeum vulgare*) deposited on 12 Nov. 2018 with NCIMB under the accession number NCIMB 43271 and referred to as "HENZ-10"; or progeny thereof. Thus, the barley plant of the invention may be barley plant HENZ-10 deposited with NCIMB on 12 Nov. 2018 and having accession number NCIMB 43271, or any progeny barley plant thereof, wherein the barley plant carries a G->A mutation of nucleotide 684 of the HvHBL12 coding sequence of SEQ ID NO:5 and/or wherein the HvHBL12 gene of said barley plant encodes a mutant HvHBL12 protein comprising a W228stop mutation of SEQ ID NO: 6.

HvWRKY38

The full-length protein product of the barley gene HvWRKY38 is believed to act as transcriptional repressor by binding to tandem repeat W-boxes. HvWRKY38 is a member of the group II WRKY transcription factors, which contain only one WRKY domain. Zou et al., 2008 has suggested that HvWRKY38 and BPBF may act as transcriptional repressors of Amy32b.

One wild type coding sequence of barley WRKY38 is provided herein as SEQ ID NO: 10. Multiple sequence alignment of HvWRKY38 CDS sequences derived from the sequences with accession numbers AJ536667.1 (cv. Ingrid), AK360269.1 (cv. Haruna Nijo), AY541586.1 (cv. Nure), MLOC_60890.1 (cv. Morex) and sequences from contig_242376 of cv Bowman (IBSC, 2012) demonstrated very high sequence identity between the CDS sequences with 2 polymorphisms at nucleotides 159 and 292 of SEQ ID NO:10. The protein sequence of wild type barley HVWRKY38 is provided herein as SEQ ID NO: 11 OR SEQ ID NO:12. Multiple sequence alignment of HVWRKY38 protein sequences translated from aforementioned genomic sequences demonstrated that all HvWRKY38 proteins have the sequence set forth as SEQ ID NO: 11 OR SEQ ID NO: 12 herein, wherein amino acid 98 may be either Val or Met. Both of these sequences are considered wild type HvWRKY38 sequences herein. The HvWRKY38 protein contains a WRKY domain at amino acids 200 to 206 of SEQ ID NO: 11 OR SEQ ID NO:12, the conserved hydrophobic residues Leu63, Val70, Leu77. Val84 and Leu91 in the leucine-zipper motif of SEQ ID NO: 11 OR SEQ ID NO: 12 and a putative zinc-finger-like motif (CX4-5CX22-23HX1H) including Cys220, Cys226, His250 and His252 of SEQ ID NO: 11 OR SEQ ID NO: 12.

The genomic sequence of the WRKY38 gene may differ amongst different barley varieties. Examples of genomic sequences of the WRKY38 barley gene is accession number AY541586.1 of the NCBI database as well as morex_contig_44877 (cv. Morex) (IBSC, 2012), and bowman_contig_242376 (cv. Bowman) available in the BARLEX database (apex.ipk-gatersleben.de/apex/f?p=284:10).

Barley Plant Carrying a Mutation in the WRKY38 Gene

In one embodiment the present invention provides a barley plant carrying a mutation in the HvWRKY38 gene leading to a loss of HVWRKY38 function, and in particular to a total loss of HvWRKY38 function. Loss of HvWRKY38 function may be determined by determining the expression level of HvWRKY38 either on the mRNA level or on the protein level. In one embodiment, a barley plant is considered to have a loss of HVWRKY38 function when the barley plant comprises less than 50%, preferably less than 25%, and even more preferably less than 10% mutant or wild type HvWRKY38 mRNA compared to the level of HVWRKY38 mRNA in a barley plant comprising a wild type HvWRKY38 gene, but otherwise of the same genotype. A barley plant may be considered to have a total loss of HVWRKY38 function when the barley plant comprises less than 5%, preferably less than 1% mutant or wild type HVWRKY38 mRNA compared to a barley plant comprising a wild type HvWRKY38 gene, but otherwise of the same genotype. Said mutant HvWRKY38 is mRNA encoded by a mutated HvWRKY38 gene carrying a mutation in the mRNA coding region. HVWRKY38 mRNA is RNA encoding a polypeptide of SEQ ID NO: 11 OR SEQ ID NO: 12 or a functional homologue thereof, and a wild type HvWRKY38 gene is a gene encoding the polypeptide of SEQ ID NO: 11 OR SEQ ID NO: 12 or a functional homologue thereof. Said functional homologue preferably shares at least 95% sequence identity with SEQ ID NO: 11 OR SEQ ID NO: 12. In one embodiment a barley plant with total loss of HVWRKY38 function may contain no detectable mutant or wild type HvWRKY38 mRNA, when determined by conventional quantitative RT-PCR.

In one embodiment, a barley plant is considered to have a loss of HVWRKY38 function when the barley plant comprises less than 50%, preferably less than 25%, and even more preferably less than 10% mutant or wild type HvWRKY38 protein compared to the level of HVWRKY38 protein in a barley plant comprising a wild type HVWRKY38 gene, but otherwise of the same genotype. A barley plant may be considered to have a total loss of HVWRKY38 function when the barley plant comprises less than 5%, preferably less than 1% mutant or wild type HVWRKY38 protein compared to a barley plant comprising a wild type HVWRKY38 gene, but otherwise of the same genotype. Said mutant HvWRKY38 protein is a polypeptide encoded by a mutated HVWRKY38 gene carrying a mutation in the coding region. HvWRKY38 protein is a polypeptide of SEQ ID NO: 11 OR SEQ ID NO: 12 or a functional homologue thereof, and a wild type HvWRKY38 gene is a gene encoding the polypeptide of SEQ ID NO: 11 OR SEQ ID NO: 12 or a functional homologue thereof. Said functional homologue preferably shares at least 95% sequence identity with SEQ ID NO: 11 OR SEQ ID NO: 12. In one embodiment a barley plant with total loss of HvWRKY38 function may contain no detectable mutant or wild type HVWRKY38 protein as detected by conventional Western blotting.

In one embodiment, a barley plant is considered to have a loss of HvWRKY38 function when an increased expression from a promoter comprising a tandem repeat W-box can be observed. Thus, loss of HvWRKY38 function may be determined by transient transfection of a reporter construct comprising a reporter gene (e.g. luciferase) under the control of an α-amylase promoter from e.g. the Amy2-1 gene. Such a construct may be prepared in the same manner as the constructs described in Raventos et al., 1998 on p. 23314 in the section "*Transient Gene Expression Assays in Onion Epidermal and Barley Aleurone Cells*". An increase in luciferase activity of at least 10%, such as at least 25% after transfection of said reporter construct to a given barley plant compared to transfection of said reporter construct to a barley plant with a wild type HvWRKY38 gene, but otherwise of the same genotype, is indicative of said barley plant having a loss of HvWRKY38 function.

In one embodiment, a barley plant is considered to have a loss of HvWRKY38 function if said barley plant carries a mutation resulting in an HvWRKY38 gene encoding a mutant HvWRKY38 protein lacking one or more of the following amino acids:
  amino acids 200 to 206 of SEQ ID NO: 11 OR SEQ ID NO:12
  amino acid 63 (Leu) of SEQ ID NO: 11 OR SEQ ID NO: 12
  amino acid 70 (Val) of SEQ ID NO: 11 OR SEQ ID NO:12
  amino acid 77 (Leu) of SEQ ID NO: 11 OR SEQ ID NO: 12
  amino acid 84 (Val) of SEQ ID NO: 11 OR SEQ ID NO:12
  amino acid 91 (Leu) of SEQ ID NO: 11 OR SEQ ID NO:12
  amino acid 220 (Cys) of SEQ ID NO: 11 OR SEQ ID NO:12
  amino acid 226 (Cys) of SEQ ID NO: 11 OR SEQ ID NO:12
  amino acid 250 (His) of SEQ ID NO: 11 OR SEQ ID NO:12
  amino acid 252 (His) of SEQ ID NO: 11 OR SEQ ID NO:12

The barley plant carrying a mutation in the HvWRKY38 gene leading to a loss of HVWRKY38 function may carry different types of mutations, e.g. any of the mutations described herein in this section.

In one embodiment the barley plant carries a mutation in the promoter region of the HVWRKY38 gene or in an intron of the HvWRKY38 gene leading to aberrant transcription of HvWRKY38 mRNA and/or aberrant translation of HvWRKY38 protein. Such barley plants may in particular have reduced HvWRKY38 mRNA levels as described herein above in this section and/or reduced HvWRKY38 protein levels as described herein above in this section.

In one embodiment the barley plant of the invention carries a mutation resulting in deletion of the HvWRKY38 gene.

In one embodiment, the barley plant of the invention carries a mutation resulting in a mutant HvWRKY38 gene encoding a mutant HvWRKY38 protein. In one embodiment the mutation may be a mutation resulting in formation of a premature stop codon. In another embodiment the mutation is a mutation in a splice site of the HvWRKY38 gene. Said mutation may lead to aberrant splicing of HvWRKY38 mRNA.

In one embodiment, the barley plant of the invention carries a mutation resulting in a mutant HvWRKY38 gene encoding a mutant HvWRKY38 protein lacking at least one the amino acids corresponding to amino acids 200 to 206, 220, 226, 250 and/or 252 of SEQ ID NO: 11 OR SEQ ID NO: 12. It is understood that a mutant HvWRKY38 lacking at least amino acids XX to YY may lack other amino acids in addition to amino acids XX to YY.

In one embodiment, the barley plant may comprise a mutant HvWRKY38 gene encoding a mutant HvWRKY38 protein lacking at least amino acids 200 to 206 of SEQ ID NO: 11 OR SEQ ID NO:12. In one embodiment, the barley plant may comprise a mutant HvWRKY38 gene encoding a mutant HvWRKY38 protein lacking at least one of amino acids 220, 226, 250 and/or 252 of SEQ ID NO: 11 OR SEQ ID NO: 12.

In one embodiment, the barley plant may comprise a mutant HvWRKY38 gene encoding a mutant HVWRKY38 protein lacking at least one of amino acids 63, 70, 77, 84 and/or 91 of SEQ ID NO: 11 OR SEQ ID NO: 12.

In one embodiment the barley plant of the invention may comprise a mutant HVWRKY38 gene encoding a mutant HvWRKY38 protein lacking at least the 102 most C-terminal amino acids, for example at least the 104 most C-terminal amino acids, such as at least the 128 most C-terminal amino acids, for example at least the 134 most C-terminal amino acids of SEQ ID NO: 11 OR SEQ ID NO: 12. For example, the barley plant may comprise a mutant HvWRKY38 gene encoding a mutant HVWRKY38 protein lacking at least the 154 most C-terminal amino acids of SEQ ID NO: 11 OR SEQ ID NO: 12.

In one embodiment the barley plant of the invention may comprises a mutant HVWRKY38 gene encoding a truncated HvWRKY38 protein comprising an N-terminal fragment of HvWRKY38 comprising at the most the 251 N-terminal amino acids of SEQ ID NO: 11 OR SEQ ID NO:12, for example at the most the 249 N-terminal amino acids of SEQ ID NO: 11 OR SEQ ID NO: 12, such as at the most the 225 N-terminal amino acids of SEQ ID NO: 11 OR SEQ ID NO: 12, for example at the most the 219 N-terminal amino acids of SEQ ID NO: 11 OR SEQ ID NO: 12, preferably at the most the 199 N-terminal amino acids of SEQ ID NO: 11 OR SEQ ID NO: 12.

In one embodiment, the barley plant of the invention may comprises a mutant HVWRKY38 gene carrying a premature stop codon in any one of codons 1 to 252, for example in any one of codons, 1 to 250, such as in any one of codons 1 to 226, for example in any one of codons 1 to 220, preferably in any one of codons 1 to 200. For example, the barley plant may comprise a mutant HvWRKY38 gene carrying a premature stop codon in codon 200. Codons are numbered according to SEQ ID NO: 10 starting at the 5' end, wherein 3 nucleotides constitutes one codon.

In one embodiment the barley plant of the invention comprises a mutant HvWRKY38 gene encoding a mutant HvWRKY38 protein having a W200stop mutation of SEQ ID NO: 11 or 12. In one preferred embodiment, the barley plant of the invention comprises a mutant HvWRKY38 gene encoding the polypeptide of SEQ ID NO: 14 or of SEQ ID NO:14, wherein amino acid 98 is Met. In particular said barley plant may comprise a G->A mutation of the nucleotide 600 of the HvWRKY38 coding sequence of SEQ ID NO: 10. For example, the barley plant may comprise a mutant HvWRKY38 gene comprising the coding sequence of SEQ ID NO: 13.

Barley Plant

The barley plant carrying a mutation in one or more α-amylase promoters, in the HRT gene, in the HBL12 gene and/or in the WRKY38 gene according to the invention may be any plant of the species *Hordeum vulgare*, including any breeding line or cultivar or variety.

"Wild barley", *Hordeum vulgare* ssp. *spontaneum*, is considered the progenitor of today's cultivated forms of barley. Domesticated, but heterogeneous mixtures of barley are referred to as barley landraces. Today, most of the landraces have been displaced in advanced agricultures by pure line cultivars. Compared with landraces, modern barley cultivars have numerous improved properties (Nevo, 1992; Pelger et al., 1992).

Within the present invention, the term "barley plant" comprises any barley plant, such as barley landraces or modern barley cultivars. Thus, the invention relates to any barley plant comprising a mutation in one or more α-amylase promoters, in the HRT gene, in the HBL12 gene and/or in the WRKY38 gene, e.g. any of the mutations described herein.

However, preferred barley plants for use with the present invention are modern barley cultivars or pure lines. The barley cultivar to be used with the present invention may, for example, be selected from the group consisting of Paustian, Sebastian, Quench, Celeste, Lux, Prestige, Saloon, Neruda, Harrington, Klages, Manley, Schooner, Stirling, Clipper, Franklin, Alexis, Blenheim, Ariel, Lenka, Maresi, Steffi, Gimpel, Cheri, Krona, Camargue, Chariot, Derkado, Prisma, Union, Beka, Kym, Asahi 5, KOU A, Swan Hals, Kanto Nakate Gold, Hakata No. 2, Kirin-choku No. 1, Kanto late Variety Gold, Fuji Nijo, New Golden, Satukio Nijo, Seijo No. 17, Akagi Nijo, Azuma Golden, Amagi Nijpo, Nishino Gold, Misato golden, Haruna Nijo, Scarlett, Rosalina and Jersey preferably from the group consisting of Haruna Nijo, Sebastian, Quench, Celeste, Lux, Prestige, Saloon, Neruda and Power, preferably from the group consisting of Paustian, Harrington, Klages, Manley, Schooner, Stirling, Clipper, Franklin, Alexis, Blenheim, Ariel, Lenka, Maresi, Steffi, Gimpel, Cheri, Krona, Camargue, Chariot, Derkado, Prisma, Union, Beka, Kym, Asahi 5, KOU A, Swan Hals, Kanto Nakate Gold, Hakata No. 2, Kirin-choku No. 1, Kanto late Variety Gold, Fuji Nijo, New Golden, Satukio Nijo, Seijo No. 17, Akagi Nijo, Azuma Golden, Amagi Nijpo, Nishino Gold, Misato golden, Haruna Nijo, Scarlett and Jersey preferably from the group consisting of Paustian, Haruna Nijo, Sebastian, Tangent, Lux, Prestige, Saloon, Neruda, Power, Quench, NFC Tipple, Barke, Class, Vintage, Applaus, Bowie, Broadway, Champ, Chanson, Charles, Chimbon, Cosmopolitan, Crossway, Dragoon, Ellinor, Embrace, Etoile, Evergreen, Flair, Highway, KWS Beckie, KWS Cantton, KWS Coralie, KWS Fantex, KWS Irina, KWS Josie, KWS Kellie, LG Diablo, LG Figaro, LG Nabuco, LG Tomahawk, Laureate, Laurikka, Lauxana, Luther, Odyssey, Ovation, Prospect, RGT Elysium, RGT Observer, RGT Planet, Rotator, Sarbi, Scholar, Subway and Golden Promise.

The barley plant may be in any suitable form. For example, the barley plant according to the invention may be a viable barley plant, a dried plant, a homogenized plant, or a milled barley kernel. The plant may be a mature plant, an embryo, a kernel, a germinated kernel, a malted kernel (e.g. in the form of green malt or kiln dried malt), a milled malted kernel, a milled kernel or the like.

Parts of barley plants may be any suitable part of the plant, such as kernels, embryos, leaves, stems, roots, flowers, or fractions thereof. A fraction may, for example, be a section of a kernel, embryo, leaf, stem, root, or flower. Parts of barley plants may also be a fraction of a homogenate or a fraction of a milled barley plant or kernel.

In one embodiment of the invention, parts of barley plants may be cells of said barley plant, such as viable cells that may be propagated in vitro in tissue cultures. In other embodiments, however, the parts of barley plants may be viable cells that are not capable of maturing into an entire barley plant, i.e. cells that are not a reproductive material.

Characteristics of Barley Plants of the Invention

The invention provides barley plants carrying a mutation in one or more α-amylase promoters, in the HRT gene, in the HBL12 gene and/or in the WRKY38 gene. One major advantage of such barley plants is an increase in α-amylase activity. In particular, said barley plants may have an increase in α-amylase activity in the kernels early during germination.

α-amylase activity of barley plants is tightly regulated. During germination α-amylase activity aids in conversion of starch to sugar. However, at other time points during plant development, e.g. during grain filling, α-amylase activity is undesired, because it may result in reduced grain filling, reduced starch content, shrivelled grains and/or pre-harvest sprouting.

The barley plants of the invention are however preferably further characterized by having good agronomical qualities, such as agronomical qualities comparable to the wild type barley. Thus, for example it may be preferred that the barley plants have a high yield, e.g. a yield comparable to the yield of high yielding modern cultivars, such as cv. Planet.

Accordingly, it is an aspect of the invention to provide barley plants, which have increased α-amylase activity during germination, but which never-the-less have good plant fitness.

In particular, barley plants of the invention carrying any of the mutations described herein may have a yield, which is at least 90% of the yield of a barley plant not comprising said mutation, but otherwise of the same genotype. Barley plants of the invention carrying a mutation in the HvHRT gene may for example have a yield, which is at least 90%, preferably at least 95% of the yield of a barley plant comprising a wild type HvHRT gene, but otherwise of the same genotype. Barley plants of the invention carrying a mutation in the HvHBL12 gene may for example have a yield, which is at least 90% of the yield of a barley plant comprising a wild type HvHBL12 gene, but otherwise of the same genotype.

Thus, barley plants according to the invention may have a 1000 kernel weight (TKW) of at least 38 g, such as of at least 40 g. In particular, barley plants of the invention carrying any of the mutations described herein may have a TKW, which is at least 90% of the TKW of a barley plant not comprising said mutation, but otherwise of the same genotype. Barley plants of the invention carrying a mutation in the HvHRT gene may for example have a TKW, which is at least 90%, such as at least 95% of the TKW of a barley plant comprising a wild type HvHRT gene, but otherwise of the same genotype. Barley plants of the invention carrying a mutation in the HvHBL12 gene may for example have a TKW, which is at least 90%, such as at least 95% of the TKW of a barley plant comprising a wild type HvHBL12 gene, but otherwise of the same genotype.

Barley plants according to the invention may have a starch content of at least 55% w/w, such as at least 60% w/w. The percentage is provided as % dry weight starch of total grain dry weight. In particular, barley plants of the invention carrying any of the mutations described herein may have a starch content, which is at least 90% of the starch content of a barley plant not comprising said mutation, but otherwise of the same genotype. Barley plants of the invention carrying a mutation in the HvHRT gene may for example have a starch content, which is at least 90%, such as at least 95% of the starch content of a barley plant comprising a wild type HvHRT gene, but otherwise of the same genotype. Barley plants of the invention carrying a mutation in the HvHBL12 gene may for example have a starch content, which is at least 90%, such as at least 95% of the starch content of a barley plant comprising a wild type HvHBL12 gene, but otherwise of the same genotype.

Barley plants according to the invention may have a protein content of at least 9.5% w/w. The percentage is provided as % dry weight protein of total grain dry weight. In particular, barley plants of the invention carrying any of the mutations described herein may have a protein content, which is at least 90% of the protein content of a barley plant not comprising said mutation, but otherwise of the same genotype. Barley plants of the invention carrying a mutation in the HvHRT gene may for example have a protein content, which is at least 90%, such as at least 95% of the protein content of a barley plant comprising a wild type HvHRT gene, but otherwise of the same genotype. Barley plants of the invention carrying a mutation in the HvHBL12 gene may for example have a protein content, which is at least 90%, such as at least 95% of the protein content of a barley plant comprising a wild type HvHBL12 gene, but otherwise of the same genotype.

Barley plants of the invention carrying any of the mutations described herein may have a height, which is at least 90% of the height of a barley plant not comprising said mutation, but otherwise of the same genotype. Barley plants of the invention carrying a mutation in the HvHRT gene may for example have a height, which is at least 90%, such as at least 95% of the height of a barley plant comprising a wild type HvHRT gene, but otherwise of the same genotype. Barley plants of the invention carrying a mutation in the HvHBL12 gene may for example have a height, which is at least 90%, such as at least 95% of the height of a barley plant comprising a wild type HvHBL12 gene, but otherwise of the same genotype.

Reduction in levels of gibberellic acid in barley plants has been described to be associated with a higher number of ears. Thus, barley mutant sdw1/denso has reduced GA biosynthetic gene expression and increased number of ears per area (Jia et al., 2011). Consequently, there is a risk, that barley plants with increased GA levels have a reduced number of ears. However, the barley plants of the invention preferably have approx. the same number of ears as wild type barley plants. Thus, barley plants of the invention carrying any of the mutations described herein may have a number of ears/m$^2$, which is at least 90% of the number of ears/m$^2$ of a barley plant not comprising said mutation, but otherwise of the same genotype. Barley plants of the invention carrying a mutation in the HvHRT gene may for example have a number of ears/m$^2$, which is at least 90%, such as at least 95% of the number of ears/m$^2$ of a barley plant comprising a wild type HvHRT gene, but otherwise of the same genotype. Barley plants of the invention carrying a mutation in the HvHBL12 gene may for example have a number of ears/m$^2$, which is at least 90%, such as at least 95% of the number of ears/m$^2$ of a barley plant comprising a wild type HvHBL12 gene, but otherwise of the same genotype.

Barley plants according to the invention carrying any of the mutations described herein are preferably not subject to pre-harvest sprouting. In particular, barley plants of the invention have a rate of germination of kernels harvested from barley plants having been subjected to regular spraying with water for 20 days, which is the same or higher than the rate of germination of the same kind of barley plant not subjected to said spraying and harvested at maturity. In particular, the barley plants according to the invention are preferably not subject to pre-harvest sprouting, when determined as described herein below in Example 3B.

In one embodiment, the barley plant of the invention has an α-amylase activity of at least 16 U/g 48 h after initiation of germination.

In one embodiment, the barley plant of the invention has an α-amylase activity of at least 4 U/g 48 h and/or of at least 7 U/g 72 h after initiation of germination, when said barley plants have been germinated while submerged in water with an airflow of 9 L/h. This may for example be the case for barley plants carrying a mutation in the HvHRT gene.

In one embodiment, the barley plant of the invention has an α-amylase activity of at least 15 U/g 48 h and/or of at least 20 U/g 72 h after initiation of germination, when said barley plants have been germinated while submerged in water with an airflow of 9 L/h. This may for example be the case for barley plants carrying a mutation in the HvHBL12 gene.

In one embodiment, the barley plant of the invention has an α-amylase activity of at least 6 U/g 72 h after initiation of germination, when said barley plants have been germinated while submerged in water without airflow. This may for example be the case for barley plants carrying a mutation in the HvHRT gene.

In one embodiment, the barley plant of the invention has an α-amylase activity of at least 4 U/g 48 h and/or of at least 14 U/g 72 h after initiation of germination, when said barley plants have been germinated while submerged in water without airflow. This may for example be the case for barley plants carrying a mutation in the HvHBL12 gene or barley plants carrying at least four α-amylase genes comprising an α-amylase promoter comprising a non-standard tandem repeat W-box.

In one embodiment the barley plant of the invention has an α-amylase activity 48 h after initiation of germination, which is at least 105%, such as at least 110%, for example at least 120% of the α-amylase activity a barley plant, which does not carry said mutation but is otherwise of the same genotype.

In one embodiment the barley plant of the invention has an α-amylase activity 72 h after initiation of germination, which is at least 120%, such as at least 150%, for example at least 170% of the α-amylase activity a barley plant, which does not carry said mutation but is otherwise of the same genotype. This may in particular be the case for barley plants carrying a mutation in HvHRT such as any of the mutation described herein.

In one embodiment the barley plant of the invention has an α-amylase activity 72 h after initiation of germination, which is at least 120%, for example at least 150%, such as at least 170% of the α-amylase activity a barley plant, which does not carry said mutation but is otherwise of the same genotype, when germinated while submerged in water without aeration. This may in particular be the case for barley plants carrying a mutation in HvHBL12 such as any of the mutation described herein.

In one embodiment the barley plant of the invention has an α-amylase activity 72 h after initiation of germination, which is at least 150%, such as at least 200%, for example at least 300% of the α-amylase activity a barley plant, which does not carry said mutation but is otherwise of the same genotype, when germinated while submerged in water without aeration. This may in particular be the case for barley plants carrying at least four α-amylase genes comprising an α-amylase promoter comprising a non-standard tandem repeat W-box, such as any of these described herein.

In one embodiment the barley plant of the invention is a hull-less barley plant and said barley plant has an α-amylase activity of at least 140 U/g, such as at least 150 U/g, for example at least 160 U/g, such as at least 170 U/G 48 h after initiation of germination. In one embodiment, the barley plant is a hull-less barley plant and said barley plant has an α-amylase activity of at least 100 U/g, such as at least 110 U/g 48 h after initiation of germination.

In one embodiment, the barley plant is a hull-less barley plant and has a limit dextrinase of at least 30 mU/g, such as at least 35 mU/g, for example at least 40 mU/g 48 h after initiation of germination. In one embodiment, the barley plant of the invention has a limit dextrinase activity of at least 20 mU/g 48 h after initiation of germination.

In one embodiment, the barley plant is a hulled barley plant, which has an α-amylase activity of at least 140 U/g, such as at least 150 U/g, for example at least 160 U/g, such as at least 170 U/G 48 h after initiation of germination, provided that at least part of the hull has been removed from the barley kernels prior to initiation of germination. In one embodiment, the barley plant is a hulled barley plant, which has an α-amylase activity of at least 100 U/g, such as at least 110 U/g 48 h after initiation of germination, provided that at least part of the hull has been removed from the barley kernels prior to initiation of germination. In one embodiment, the barley plant is a hulled barley plant, which has a limit dextrinase activity of at least 30 mU/g, such as at least 35 mU/g, for example at least 40 mU/g 48 h after initiation of germination, provided that at least part of the hull has been removed from the barley kernels prior to initiation of germination. In one embodiment, the barley plant is a hulled barley plant, which has a limit dextrinase activity of at least 20 mU/g, provided that at least part of the hull has been removed from the barley kernels prior to initiation of germination. For example, said hull may be removed by mechanical treatment. Said hull may be removed by mechanical treatment in a manner for example resulting in a decrease of the total weight of the barley kernels of at least 2%, such as at least 3%, for example in the range of 3-6%.

In one embodiment the barley plants of the invention may have improved germination under stress conditions. Thus, in one embodiment at least 60%, preferably at least 70%, for example at least 75% of kernels of said barley plant germinates under high water conditions, for example when determined as described in Example 3C.

Barley Plants Comprising More than One Mutation

The invention also provides barley plants comprising more than one mutation. Accordingly, the barley plants of the invention may comprise one or more of the following mutations
 a mutation in one or more α-amylase promoters, for example any of the mutations described herein above in the section "α-amylase and barley plants carrying a mutation in an α-amylase promoter",
 a mutation in the HvHRT gene, for example any of the mutations described herein above in the section "Barley plant carrying a mutation in the HRT gene"
 a mutation in the HvHBL12 gene, for example any of the mutations described herein above in the section "Barley plant carrying a mutation in the HvHBL 12 gene"
 a mutation in the HvWRKY38 gene, for example any of the mutation described herein above in the section "Barley plant carrying a mutation in the WRKY38 gene"

In addition to the mutations described herein the barley plants may also comprise one or more further mutations. Accordingly, the barley plant may comprises one or more of following mutations.

In addition to one or more of the mutations described above, the barley plant may also comprise a mutation in the gene encoding LOX-1 resulting in a total loss of functional LOX-1. Said mutation may for example be any of the mutations described in international patent application WO 2005/087934. For example the barley plant may comprise a gene encoding LOX-1 comprising a premature stop codon, said codon corresponding to base nos. 3572-3574 of SEQ ID NO:2 of WO 2005/087934 or a splice site mutation, said mutation corresponding to base no. 2311 of SEQ ID NO: 6 of SEQ ID NO:2 of WO 2005/087934.

In addition to one or more of the mutations described above, the barley plant may also comprise a mutation in the gene encoding LOX-2 resulting in a total loss of functional LOX-2. Said mutation may for example be any of the mutations described in international patent application WO 2010/075860. For example the barley plant may comprise a gene encoding LOX-2 comprising a mutation at nucleotide position 2689 of SEQ ID NO:1 of WO 2010/075860, leading to formation of a premature stop codon.

In addition to one or more of the mutations described above, the barley plant may also comprise a mutation in the gene encoding MMT resulting in a total loss of functional MMT. Said mutation may for example be any of the mutations described in international patent application WO 2010/063288. For example the barley plant may comprise a gene encoding MMT comprising a G->A mutation of base no. 3076 of SEQ ID NO:3 of WO 2010/063288 or a gene encoding MMT comprising a G->A mutation of base no. 1462 of SEQ ID NO: 16 WO 2010/063288.

In addition to one or more of the mutations described above, the barley plant may also comprise a mutation in the gene encoding CsIF6, wherein said mutant gene encodes mutant CsIF6 protein with reduced CsIF6 activity. Said mutation may for example be any of the mutations described in co-pending application entitled "Cereal plants with improved cell wall properties" assigned to the same applicant and with the same filing date as the present application. For example the barley plant may comprise a gene encoding CsIF6 encoding mutant CsIF6 comprising a G847E mutation, or a G748D mutation or a T7091 mutation of SEQ ID NO:1 or SEQ ID NO:3 of said co-pending application. SEQ ID NO:1 of said co-pending application has GenBank accession number NCBI: EU267181.1.

Plant Products

The invention also provides plant products prepared from a barley plant carrying a mutation in one or more α-amylase promoters, in the HRT gene, in the HBL12 gene and/or in the WRKY38 gene, e.g. any of the barley plants described herein.

The plant product may be any product prepared from a barley plant, for example a food, a feed or a beverage. Thus the plant product may be any of the beverages described herein below in the section "Beverage and method of production thereof". The plant product may also be an aqueous extract of the barley plant and/or malt prepared from kernels of said barley plant, for example the plant product may be wort. Said aqueous extract may for example be prepared as described herein below in the section "Aqueous extract and methods of production thereof".

In one embodiment the plant product may be malt, e.g. a green malt or a kiln dried malt, such as any of the malts described herein below in the section "Green malt, malt and methods of production thereof" or a malt based product, such as malt based beverages. Although the primary use of green malt and/or kiln dried malt is for beverage production, it can also be utilized in other industrial processes, for example as an enzyme source in the baking industry, or in the food industry as a flavouring and colouring agent, e.g. in the form of malt or malt flour or indirectly as a malt syrup, etc. Thus, the plant product according to the invention may be any of the aforementioned products.

In another aspect, the plant products according to the invention comprise, or even consist of syrup, such as a barley syrup, or a barley malt syrup. The plant product may also be an extract of barley or malt. Thus, the plant product may be wort.

Green Malt, Kiln Dried Malt and Methods of Production Thereof

The invention also provides malt prepared from a barley plant carrying a mutation in one or more α-amylase promoters, in the HRT gene, in the HBL12 gene and/or in the WRKY38 gene, for example any of the barley plants described herein. Said malt may be green malt or kiln dried malt prepared from barley grains from a barley plant carrying a mutation in one or more α-amylase promoters, in the HRT gene, in the HBL12 gene and/or in the WRKY38 gene. Said mutation may be any of the mutations described herein above.

Green malt may be prepared by malting, i.e. by germination of cereal grains under controlled environmental conditions. Typically, said germination may comprise a step of steeping barley kernels followed by a step of germination. Steeping and germination may also be performed simultaneously or partly simultaneously. In some embodiments, the production of malt may comprise a step of drying the germinated grains. Said drying step may preferably be kiln drying of the germinated kernels at elevated temperatures. Thus, kiln dried malt may be prepared by subjecting green malt to a step of kiln drying.

Thus, in one embodiment a method of malting may comprise the steps of:
(a) providing kernels of a barley plant, notably a barley plant, carrying a mutation in one or more α-amylase promoters, in the HRT gene, in the HBL12 gene and/or in the WRKY38 gene;
(b) steeping said barley kernels;
(b) germinating said barley kernel; and
(c) drying said germinated barley kernels, preferably by kiln drying.

Germinated barley grains may be prepared by a method comprising the steps of
(a) providing kernels of a barley plant, notably a barley plant, carrying a mutation in one or more α-amylase promoters, in the HRT gene, in the HBL12 gene and/or in the WRKY38 gene;
(b) steeping said barley kernels;
(b) germinating said barley kernel.

The steps of steeping and germinating may be performed at sequentially, simultaneously or partly simultaneously.

In one preferred embodiment steeping and germination is performed simultaneously in a germination process, which comprises incubating barley grains in an aqueous solution typically under aeration for at the most 72 h.

Steeping may be performed by any conventional method known to the skilled person. One non-limiting example involves steeping at a temperature in the range of 10 to 25° C. with alternating dry and wet conditions. During steeping, for example, the barley kernels may be incubated wet for in the range of 30 min to 3 h followed by incubation dry for in the range of 30 min to 3 h and optionally repeating said incubation scheme in the range of 2 to 5 times. The final water content after steeping may, for example, be in the range of 40 to 50%, for example in the range of 40-45%.

The barley plants provided by the invention are characterized by carrying a mutation in one or more α-amylase promoters, in the HRT gene, in the HBL12 gene and/or in the WRKY38 gene. One major advantage of such barley plants is increased activity of hydrolytic enzymes, such as α-amylase and limit dextrinase during germination. Grains of these barley plants may be advantageously germinated in a short germination process, because one aim of malting is induction of sufficient hydrolytic enzyme activity. Interestingly, the barley plants of the invention have a level of hydrolytic enzyme activity early during germination to allow use of short germination processes.

Examples of useful short germination processes are described in international patent application PCT/EP2017/065498, which is incorporated by reference herein. One example of a useful short germination process is a germination process comprising a step where the barley grains are incubated in an aqueous solution typically under aeration, wherein the entire germination process is performed for at the most 72 h.

As described above the germination may comprise a step of incubating grains of a barley plant carrying a mutation in one or more α-amylase promoters, in the HRT gene, in the HBL12 gene and/or in the WRKY38 gene in an aqueous solution under aeration. The barley grains may be incubated in said aqueous solution for sufficient time to allow germination of the majority of said barley grains. The barley grains may also be incubated in said aqueous solution for sufficient time in order to obtain a water content of at least 35%, preferably of at least 37%, for example in the range of 35 to 60%. Typically, the barley grains are incubated in the aqueous solution for at least 20 h, such as at least 24 h. Typically, the grains are incubated in said aqueous solution for at the most 72 h, such as for at the most 60 h, for example for at the most 48 h. Thus, in some embodiments the barley grains are incubated in said aqueous solution for in the range of 20 to 72 h, such as for in the range of 20 to 60 h, for example for in the range of 20 to 48 h, for example for in the range of 20 to 30 h, such as for in the range of 22 to 26 h.

It may be preferred that the barley grains are completely covered by said aqueous solution during the entire incubation.

Said barley grains are frequently incubated in said aqueous solution, while $O_2$ is passed through the aqueous solution. Said $O_2$ may be added to said aqueous solution as pure $O_2$. Frequently, however, said $O_2$ is comprised within a gas mixture. In one embodiment said $O_2$ is comprised within atmospheric air.

In general, at least 2 L, preferably at least 3 L, more preferably at least 4 L, yet more preferably at least 5 L, even more preferably at least 6 L $O_2$ passes through said aqueous solution per kg barley grains per h. The weight of said barley grains is the dry weight. For example, in the range of 2 to 100 L, for example in the range of 2 to 75 L, such as in the range of 2 to 50 L, for example in the range of 4 to 100 L, for example in the range of 4 to 75 L, such as in the range of 4 to 50 L, for example in the range of 6 to 100 L, for example in the range of 6 to 75 L, such as in the range of 6 to 50 L $O_2$ passes through said aqueous solution/barley grain mixture per kg barley grains (dry weight) per h.

As noted above, it is frequently atmospheric air that is passed through the aqueous solution. Thus, the method may comprise passing at least 10 L, preferably at least 15 L, more preferably at least 20 L, yet more preferably at least 25 L, even more preferably at least 30 L atmospheric air through said aqueous solution per kg barley grains per h. The weight of said barley grains is the dry weight. For example, in the range of 10 to 500 L, for example in the range of 10 to 375 L, such as in the range of 10 to 250 L, for example in the range of 20 to 500 L, for example in the range of 20 to 375 L, such as in the range of 20 to 250 L, for example in the range of 30 to 500 L, for example in the range of 30 to 375 L, such as in the range of 30 to 250 L atmospheric air is passed through said aqueous solution per kg barley grains (dry weight) per h.

In some embodiments the step of germination comprises
 a. at least one step of incubating said kernels in an aqueous solution, wherein at least 2 L $O_2$ per kg dry weight barley kernels is passed through said aqueous solution per h; and
 b. at least one step of incubating said barley kernels in air.

In some embodiments, after incubation of the barley grains in said aqueous solution, then the barley grains have a water content of at least 20%, preferably of at least 30%, for example in the range of 30 to 60%, such as in the range of 30 to 50%, for example in the range of 30 to 60%, such as in the range of 30 to 50%.

During said step of incubating said barley kernels in air, at least 2 L $O_2$ per kg dry weight barley kernels may be passed through said barley kernels per h. For example, the same amount of $O_2$ may be lead through the barley kernels during incubation in air as during incubation in said aqueous solution as described above.

The germinated barley kernels prepared by this method are also referred to as green malt herein.

The water content of barley grains may be determined by determining the weight of the barley grains, followed by drying said barley grains and determining the weight of the dried barley grains. The difference in weight of the wet and dry barley grains is considered to be water, and the water content is provided as the weight of the water divided by the total weight of the barley grains (wet barley grains). The water content provided in % is thus a w/w %.

The barley grain may be incubated at any useful temperature, however it may be preferred that incubation is performed at a temperature sufficiently high to allow fast increase in water content.

In particular, in embodiments of the invention wherein the barley grains are incubated at a temperature in the range of 20 to 30° C., then said barley grains may be incubated for in the range of 20 to 48 h.

Germination of grains may also be performed by any conventional method known to the skilled person. One non-limiting example involves germination at a temperature in the range of 10 to 25° C., optionally with changing temperature in the range of 1 to 4 days.

As mentioned above in some embodiments of the invention, the germinated barley grains (i.e. the green malt) may be kiln dried. In some embodiments it is preferred that the green malt is not kiln dried. In particular, it is preferred, that when green malt is prepared by a germination comprising a step of incubating said barley grains in an aqueous solution under aeration, then the green malt is not kiln dried.

If the green malt is kiln dried, this may be done at conventional temperatures, such as at least 75° C., for example in the range of 80 to 90° C., such as in the range of 80 to 85° C. Thus, the malt may, for example be produced by any of the methods described by Hough et al. (1982). However, any other suitable method for producing malt may also be used with the present invention, such as methods for production of specialty malts, including, but not limited to, methods of roasting the malt.

Kiln dried malt and green malt may be further processed, for example by milling. Thus, the plant product according to the invention may be any kind of malt, such as unprocessed malt or milled malt, such as flour. Thus, the plant product may for example be milled, kiln dried malt or milled green malt. Milled malt and flour thereof comprise chemical components of the malt and dead cells that lack the capacity to re-germinate.

In some embodiments the barley is hulled barley, and the method comprises a step of removing at least part of said hull prior to incubating said kernels in an aqueous solution. Hulled cereal grains may be treated to remove hull by subjecting the cereal grains to physical treatment removing hull. Said physical treatment may for example be selected from the group consisting of polishing, sanding, peeling and smoothening. Preferably, the physical treatment results in a loss of the hull. Loss of the hull may be determined as an overall weight loss. Thus, the physical treatment preferably leads to a loss of in the range of 1 to 4%, such as in a loss of in the range of 1.5 to 3.0% of the total weight of the cereal grains.

Aqueous Extract and Methods of Production Thereof

The invention provides barley based beverages as well as methods of preparing the same, wherein the barley plant carries a mutation in one or more α-amylase promoters, in the HRT gene, in the HBL12 gene and/or in the WRKY38 gene, e.g. any of the mutations described herein. The invention also provides aqueous extracts of kernels of barley plants carrying a mutation in one or more α-amylase promoters, in the HRT gene, in the HBL12 gene and/or in the WRKY38 gene. Said aqueous extract may for example be prepared from green malt or kiln dried malt.

Frequently, methods for preparing a beverage comprise a step of preparing an aqueous extract of kernels of the barley plants of the invention and/or of malts prepared from barley plants of the invention.

The aqueous extract may, in general, be prepared by incubating barley flour, flour of green malt and/or flour of kiln dried malt in water or in an aqueous solution. Said aqueous solution is also referred to as "mashing solution" herein. In particular, the aqueous extract may be prepared by mashing.

The present invention also provides a method of producing an aqueous extract, said method comprising the steps of:
 a. providing kernels of a barley plant, wherein said barley plant carry a mutation in one or more α-amylase promoters, in the HRT gene, in the HBL12 gene and/or in the WRKY38 gene, e.g. any of the mutations as described herein;
 b. subjecting the barley kernels to a step of germination thereby obtaining germinated kernels, wherein said step of germination comprises incubating said kernels in an aqueous solution at the most 72 h;
 c. finely dividing said germinated kernels, while said germinated kernels have a water content of at least 20%, with the proviso that said barley kernels do not have a water content below 20 at any time between steps b) and c);

d. preparing an aqueous extract of said milled germinated kernels, thereby producing an aqueous extract of the barley.

The germination step is described in detail in the section above "Green malt, kiln dried malt and method of production thereof".

In general said mashing solution may be water, such as tap water to which one or more additional agents may be added. The additional agents may be present in the aqueous solution from the onset or they may be added during the process of preparing an aqueous extract. Said additional agents may be enzymes. Thus, the mashing solution may comprise one or more enzymes. Said enzymes may be added to the aqueous solution from the onset, or subsequently, during the process.

Said enzymes may, for example, be one or more hydrolytic enzymes. Suitable enzymes include lipases, starch degrading enzymes (e.g. amylases), glucanases [preferably (1-4)- and/or (1,3;1,4)-β-glucanases], and/or xylanases (such as arabinoxylanases), and/or proteases, or enzyme mixtures comprising one or more of the aforementioned enzymes, e.g. Cereflo, Ultraflo, or Ondea Pro (Novozymes). For example, the aqueous solution may comprise one or more hydrolytic enzymes selected from the group consisting of α-amylase, β-amylase, limit dextrinase, pullulanase, β-glucanase (e.g. endo-(1,3;1,4)-β-glucanase or endo-1,4-β-glucanase),xylanase (e.g. endo- or exo-1,4-xylanase, an arabinofuranosidase or a ferulic acid esterase), glucoamylase and protease.

In one embodiment no or only limited amounts of α-amylase is added to said mashing solution.

In one embodiment no or only limited amounts of limit dextrinase and pullulanase is added to said mashing solution.

Said additional agents, preferably of food grade quality, may also be a salt, for example $CaCl_2$), or an acid, for example $H_3PO_4$.

The aqueous extract is generally prepared by incubation of the barley flour, flour of green malt and/or flour of kiln dried malt in the mashing solution at one or more predetermined temperature(s). Said predetermined temperature may also be referred to as "mashing temperature" herein. Said mashing temperatures may for example be conventional temperatures used for mashing. The mashing temperature is in general either kept constant (isothermal mashing), or gradually increased, for example increased in a sequential manner. In either case, soluble substances in the barley grains and/or malt are liberated into said mashing solution thereby forming an aqueous extract.

The mashing temperature(s) are typically temperature(s) in the range of 30 to 90° C., such as in the range of 40 to 85° C., for example in the range of 50 to 85° C. Frequently, incubation with the mashing solution includes a final step of heating to a higher temperature, e.g. to a temperature in the range of 75 to 80° C.

Subsequent to incubation in the aqueous solution in e.g. a mashing vessel, the aqueous solution may be transferred to another container, e.g. a lauter tun and incubated for additional time at elevated temperature.

Non-limiting examples of useful mashing protocols can be found in the literature of brewing, e.g. in Hough et al. (supra).

Mashing (i.e. incubation of the barley flour, flour of green malt and/or flour of kiln dried malt in mashing solution) can occur in the presence of adjuncts, which is understood to comprise any carbohydrate source other than malt or germinated barley grains, such as, but not limited to, barley, barley syrups, or maize, or rice-either as whole kernels or processed products like grits, syrups or starch. All of the aforementioned adjuncts may be used principally as an additional source of extract (syrups are typically dosed during wort heating). The requirements for processing of the adjunct in the brewery depend on the state and type of adjunct used.

After incubation in the mashing solution, the aqueous extract may typically be separated, e.g. through filtration into the aqueous extract and residual non-dissolved solid particles, the latter also denoted "spent grain". Filtering may for example be performed in a lauter tun. Alternatively, the filtering may be filtering through a mash filter. The aqueous extract thus obtained may also be denoted "first wort". Additional liquid, such as water may be added to the spent grains during a process also denoted sparging. After sparging and filtration, a "second wort" may be obtained. Further worts may be prepared by repeating the procedure. Thus, the aqueous extract may be wort, e.g. a first wort, a second wort, a further wort or a combination thereof.

Figure 12:
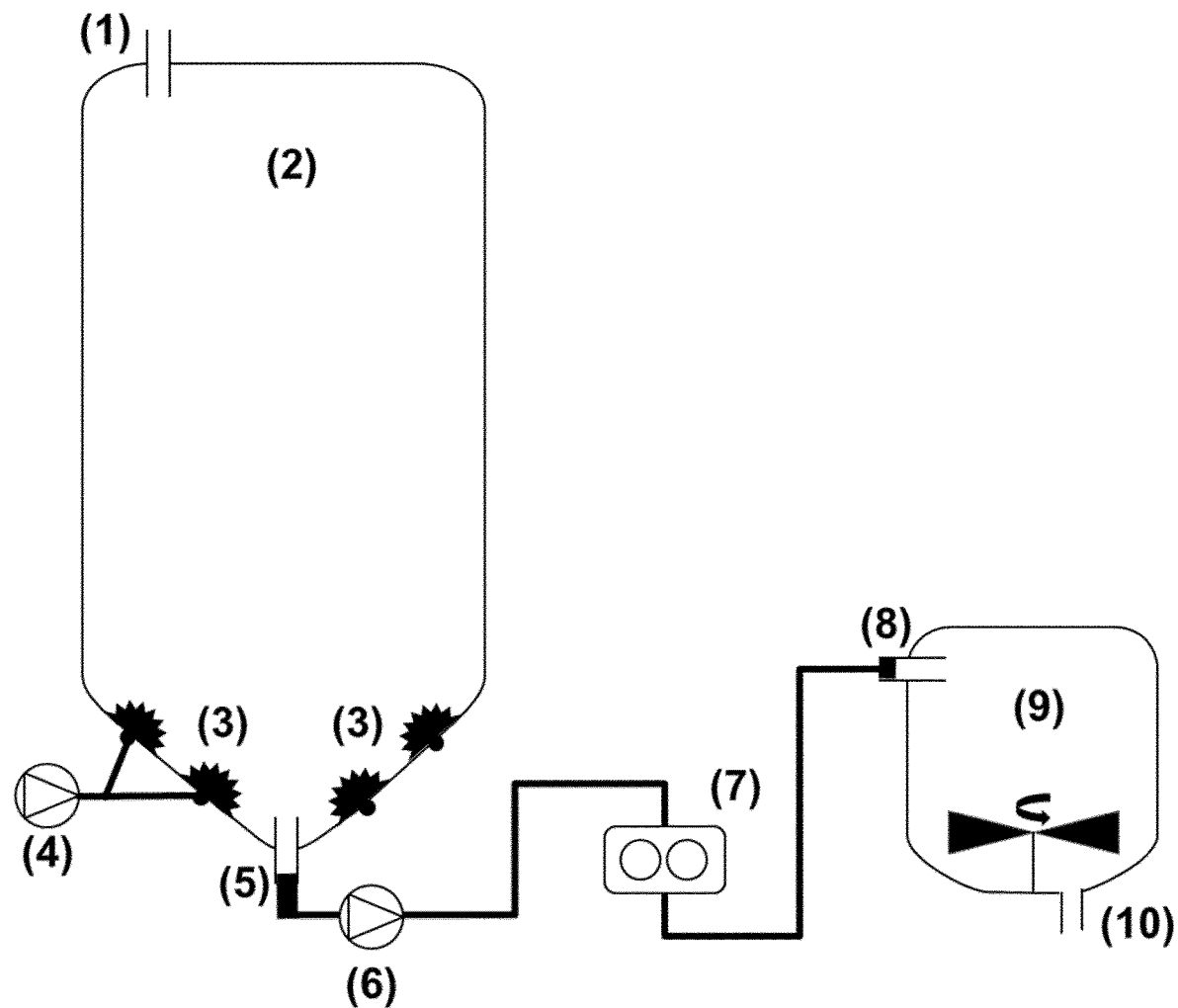
FIG. 12 shows an example of equipment useful for preparing green malt. The equipment comprises a tank (2) in which grains can be immersed in an aqueous solution and aerated continuously. The equipment comprises an inlet for barley grains (1), a tank, e.g. a steeping tank (2); inlets for gas, e.g. sinter stones (3); a pump e.g. an air pump (4); an outlet for barley grains (5); a grain pump (6); an equipment for finely dividing barley grains e.g. a mill (7); an inlet (8); a vessel, e.g. a mashing vessel (9), and; an outlet (10).

The method of preparing an aqueous extract may in one embodiment be performed using any of the apparatuses described in international patent application PCT/EP2017/065498, for example any of the apparatuses described on p. 20-22 therein. A non-limiting example of a useful apparatus is provided herein in FIG. 12.

Beverage and Method of Production Thereof

The present invention also provides barley based beverages and methods of producing such beverages, wherein the beverages are prepared from a barley plant carrying a mutation in one or more α-amylase promoters, in the HRT gene, in the HBL12 gene and/or in the WRKY38 gene, e.g. any of the mutations described herein.

Said beverage may be an alcoholic barley based beverages or non-alcoholic barley based beverages. Alcoholic barley based beverages may for example be beer or a distilled alcohol.

Said beer may be any kind of beer, for example lager or ale. Thus, the beer may for example be selected from the group consisting of Altbier, Amber ale, Barley wine, Berliner Weisse, Bière de Garde, Bitter, Blonde Ale, Bock, Brown ale, California Common, Cream Ale, Dortmunder Export, Doppelbock, Dunkel, Dunkelweizen, Eisbock, Fruit lambic, Golden Ale, Gose, Gueuze, Hefeweizen, Helles, India pale ale, Kolsch, Lambic, Light ale, Maibock, Malt liquor, Mild, Märzenbier, Old ale, Oud bruin, Pale ale, Pilsener, Porter, Red ale, Roggenbier, Saison, Scotch ale, Steam beer, Stout, Schwarzbier, lager, Witbier, Weissbier and Weizenbock.

Said distilled alcohol may be any kind of distilled alcohol. In particular the distilled alcohol may be based on a barley, e.g. a barley malt. Non-limiting examples of such distilled alcohol include whiskey and vodka.

The beverage may be a non-alcoholic beverage, such as a non-alcoholic barley based beverage, e.g. non-alcoholic beer or non-alcoholic malt beverages, such as maltina.

The beverage may for example be prepared by a method comprising the steps of:
(i) Providing kernels of a barley plant according to the invention and/or green malt and/or kiln dried malt prepared from kernels of a barley plant according to the invention (ii) Preparing an aqueous extract of said kernels and/or said green malt and/or said kiln dried malt, e.g. as described herein above in the section preparing aqueous extract (iii) processing said aqueous extract into a beverage.

The aqueous extract may be boiled with or without hops where after it may be referred to as boiled wort. First, second and further worts may be combined, and thereafter subjected to boiling. The aqueous extract may be boiled for any suitable amount of time, e.g. in the range of 60 min to 120 min.

Step (iii) may comprise
a. heating said aqueous extract optionally in the presence of hops or hops extract;
b. cooling the aqueous extract;
c. fermenting said aqueous extract with yeast, thereby producing a fermented beverage.

Step (iii) may in particular comprise fermentation of said aqueous extract, e.g. by fermentation of wort. Thus, the beverage may be prepared by fermentation of the aqueous extract with yeast.

Once the aqueous extract has been prepared it may be processed into beer by any method including conventional brewing methods. Non-limited descriptions of examples of suitable methods for brewing can be found, for example, in publications by Hough et al. (1982). Numerous, regularly updated methods for analyses of barley and beer products are available, for example, but not limited to, American Association of Cereal Chemists (1995), American Society of Brewing Chemists (1992), European Brewery Convention (1998), and Institute of Brewing (1997). It is recognized that many specific procedures are employed for a given brewery, with the most significant variations relating to local consumer preferences. Any such method of producing beer may be used with the present invention.

The first step of producing beer from the aqueous extract preferably involves boiling said aqueous extract as described herein above, followed by a subsequent phase of cooling and optionally whirlpool rest. One or more additional compounds may be added to the aqueous extract, e.g. one or more of the additional compounds described below in the section "Additional compounds". After being cooled, the aqueous extract may be transferred to fermentation tanks containing yeast, e.g. brewing yeast, such as *S. pastorianus* or *S. cerevisiae*. The aqueous extract may be fermented for any suitable time period, in general in the range of 1 to 20 days, such as 1 to 10 days. The fermentation is performed at any useful temperature e.g. at a temperature in the range of 10 to 20° C. The methods may also comprise addition of one or more enzymes, e.g. one or more enzymes may be added to the wort prior to or during fermentation. In particular, said enzyme may be a proline-specific endoprotease. A non-limiting examples of a proline-specific endoprotease is "Brewer's Clarex" available from DSM. In other embodiments, no exogenous enzymes are added during the methods.

During the several-day-long fermentation process, sugar is converted to alcohol and $CO_2$ concomitantly with the development of some flavour substances. The fermentation may be terminated at any desirable time, e.g. once no further drop in % P is observed.

Subsequently, the beer may be further processed, for example chilled. It may also be filtered and/or lagered—a process that develops a pleasant aroma and a less yeast-like flavour. Additives may also be added. Furthermore, $CO_2$ may be added. Finally, the beer may be pasteurized and/or filtered, before it is packaged (e.g. transferred to containers or kegs, bottled or canned). The beer may also be pasteurized by standard methods.

Additional Compounds

The methods of the invention may comprise the step of adding one or more additional compounds. Said additional compounds may for example be a flavor compound, a preservative, a functional ingredient, a color, a sweetener, a pH regulating agent or a salt. The pH regulating agent may for example be a buffer or an acid, such as phosphoric acid.

Functional ingredients may be any ingredient added to obtain a given function. Preferably a functional ingredient renders the beverage healthier. Non-limiting examples of functional ingredients includes vitamins or minerals.

The preservative may be any food grade preservative, for example it may be benzoic acid, sorbic acid, sorbates (e.g. potassium sorbate), sulphites and/or salts thereof.

The additional compound may also be $CO_2$. In particular, $CO_2$ may be added to obtain a carbonated beverage.

The flavour compound to be used with the present invention may be any useful flavour compound. The flavour compound may for example be selected from the group consisting of aromas, plant extracts, plant concentrates, plant parts and herbal infusions. In particular the flavor compounds may be hops.

Method of Preparing a Barley Plant Carrying a Mutation in One or More α-Amylase Promoters, in the HRT Gene, in the HBL12 Gene and/or in the WRKY38 Gene Barley plants carrying a mutation in one or more α-amylase promoters, in the HRT gene, in the HBL12 gene and/or in the WRKY38 gene, e.g. any of the mutations described herein may be prepared in any useful manner.

For example, such barley plants can be prepared by a method comprising the steps of:
subjecting a plurality of barley plants or barley kernels to random mutagenesis, e.g. by irradiation or chemical treatment, e.g. treatment with sodium azide;
identifying barley plants or barley kernels carrying the desired mutation (e.g. a mutation one or more α-amylase promoters, in the HRT gene, in the HBL12 gene and/or in the WRKY38 gene).

Such methods may also include one or more steps of reproducing said barley plants/barley kernels in order to obtain multiple barley plants/kernels each carrying random mutations.

In particular, barley plants carrying a particular mutation may be prepared and identified essentially as described in international patent application PCT/EP2017/065516 using primers and probes designed to identify the desired mutation. A non-limiting example of primers and probes useful for identication of a barley plant carrying a mutation in an α-amylase promoter is provided in Example 13A. A non-limiting example of primers and probes useful for identication of a barley plant carrying a mutation in the HRT gene is provided in Example 2A. Two additional non-limiting examples of primers and probes useful for identification of a barley plant carrying a mutation in the HRT gene are provided in Example 14. A non-limiting example of primers and probes useful for identication of a barley plant carrying a mutation in the HBL12 gene is provided in Example 7A. A non-limiting example of primers and probes useful for identication of a barley plant carrying a mutation in WRKY38 gene is provided in Example 12A. The skilled persons will based on common general knowledge and/or the guidance provided in international patent application PCT/EP2017/065516, which is incorporated herein by reference be able to design useful primers and probes for identification of other mutants.

Barley plants carrying a mutation in one or more α-amylase promoters, in the HRT gene, in the HBL12 gene and/or in the WRKY38 gene may also be prepared using various site directed mutatgenesis methods, which for example can be designed based on the sequence of the α-amylase promoters, HRT gene, HBL12 gene and/or WRKY38 gene provided herein. In one embodiment, the barley plant is prepared using any one of CRISPR, a TALEN, a zinc finger, meganuclease, and a DNA-cutting antibiotic as described in WO 2017/138986. In one embodiment, the barley plant is prepared using CRISPR/cas9 technique, e.g. using RNA-guided Cas9 nuclease. This may be done as described in Lawrenson et al., Genome Biology (2015) 16:258; DOI 10.1186/s13059-015-0826-7 except that the single guide RNA sequence is designed based on the genes sequences provided herein. In one embodiment, the barley plant is prepared using a combination of both TALEN and CRISPR/cas9 techniques, e.g. using RNA-guided Cas9 nuclease. This may be done as described in Holme et al., Plant Mol Biol (2017) 95:111-121; DOI: 10.1007/s11103-017-0640-6 except that the TALEN and single guide RNA sequence are designed based on the genes sequences provided herein.

In one embodiment, the cereal plant is prepared using homology directed repair, a combination of a DNA cutting nuclease and a donor DNA fragment. This may be done as described in Sun et al., Molecular Plant (2016) 9:628-631; DOI: doi.org/10.1016/j.molp.2016.01.001 except that the DNA cutting nuclease is designed based on the genes sequences provided herein and the donor DNA fragment is designed based on the coding sequence of the mutated cereal variant provided herein.

In one embodiment of the invention, the objective is to provide agronomical useful barley plants carrying a mutation in in one or more α-amylase promoters, in the HRT gene, in the HBL12 gene and/or in the WRKY38 gene. In addition to the mutation in the in one or more α-amylase promoters, in the HRT gene, in the HBL12 gene and/or in the WRKY38 gene, there are additional factors which also may be considered in the art of generating a commercial barley variety useful for malting and/or brewing and/or as base for beverages, for example kernel yield and size, and other parameters that relate to malting performance or brewing performance. Since many-if not all-relevant traits have been shown to be under genetic control, the present invention also provides modern, homozygous, high-yielding malting cultivars, which may be prepared from crosses with the barley plants that are disclosed in the present publication. The skilled barley breeder will be able to select and develop barley plants, which-following crossings with other barley plants-will result in superior cultivars. Alternatively, the breeder may utilize plants of the present invention for further mutagenesis to generate new cultivars carrying additional mutations in addition to the mutation in one or more α-amylase promoters, in the HRT gene, in the HBL12 gene and/or in the WRKY38 gene.

The invention also comprise barley plants carrying a mutation in one or more α-amylase promoters, in the HRT gene, in the HBL12 gene and/or in the WRKY38 gene prepared from plant breeding method, including methods of selfing, backcrossing, crossing to populations, and the like. Backcrossing methods can be used with the present invention to introduce into another cultivar the mutation in one or more α-amylase promoters, in the HRT gene, in the HBL12 gene and/or in the WRKY38 gene.

In one embodiment, the invention relates to progeny of the barley plant deposited on 12 Nov. 2018 with NCIMB under the accession number NCIMB 43270 and referred to as "HENZ-2" or progeny of the barley plant deposited on 12 Nov. 2018 with NCIMB under the accession number NCIMB 43271 and referred to as "HENZ-10".

A way to accelerate the process of plant breeding comprises the initial multiplication of generated mutants by application of tissue culture and regeneration techniques. Thus, another aspect of the present invention is to provide cells, which upon growth and differentiation produce barley plants carrying the mutation in one or more α-amylase promoters, in the HRT gene, in the HBL12 gene and/or in the WRKY38 gene. For example, breeding may involve traditional crossings, preparing fertile anther-derived plants or using microspore culture.

In one embodiment the barley plant of the invention has not exclusively been obtained by means of an essentially biological process. Progeny of a barley plant obtained by a technical process is herein considered as not being exclusively obtained by means of an essentially biological process, because the parent plant is obtained by a technical process.

In one embodiment the barley plant carries any of the mutations described herein, wherein said mutation has been induced by chemical and/or physical agents.

In one embodiment the barley plant has been prepared by a method involving a step of induced mutagenesis or said plant is progeny of a plant prepared by a method involving a step of induced mutagenesis. Thus, the barley plant may be a barley plant prepared by a method comprising the following steps or progeny of a plant prepared by a method comprising the following steps:

Mutagenizing barley plants or parts thereof, for example with a chemical mutagenizing agent such as $NaN_3$.
Selecting barley plants carrying any of the mutations described herein.

| Sequences | |
|---|---|
| SEQ ID NO: 1<br>Coding sequence<br>of the HvHRT<br>gene<br>ID# AK362734<br>(cv. Haruna Nijo) | ATGCCTGCGGTCGCCGCTGCCAGATTGAAGCGGGAGGACTGCCCCCGCACCAA<br>ACACGATTCCCTCTTCTCCCCATGGAAGGTTCTTGTCGGGCCGTCGGACTGGG<br>AGGACCACTCCGCCGGCAAGGAGGGGGTCCAGAGGTATCACACACGCAACCTC<br>CCGGACAACTTCCCTGGCCTCTACGAGCTGGGCGTTGCAAGGCCTTCCTATGA<br>TGGTGTCAGGGCTCGCAGAAATCGATCAGTTGTCGTCGTGGTGGTATACCTCG<br>GGCAGGCCGATAATGTCAGGGCGAGGCTCCAGCAGTACGGGCGGACAGGGTCA<br>CACCTGGACACCGGGAATCCGTTGGCTGCTGTCTGTAAAGCTGAGATGAACGC<br>GCTCACGGCAGGACCTGGATTGTTCAGGGAAGTCTTCTCCAGAGGCTACTCTA<br>TGATGTTTCGATGTGCGCTGATGGGTTCCAAAAAGGCAGCTGAGAAGACTGAA<br>GGTCAGCTACTGGGAGTATTTGATTATGCATGGAATAAACTGCAGAATGGTGC<br>GTGTCGTCGCGAAGAAATACTGCTCAAGTTAGAACAGGGAAGCAATAGATTAT<br>CTTTGCTTAGCAGAGTCCGGCACTTAAAACAGAGGGTGTTTGGAGAGAAAGCA<br>GGTATAAAGATTAACAGCAGTGGGTCTGTTGAGATTTCATCTAGCAGTATGAA<br>AAATATGCTTCCAAGAGTCCGTACGTTTGTCGGCTTCAGGCCTCGTTTGGTTA |

| | Sequences |
|---|---|
| | ACTCTGGCGACGATTTAAACGAGGCAAGTGATATTCACCGAAAATGCACACCT<br>CAGGCCAATACTGCTGGTAAACAAGCACATAGAAGGTCTGAAGGATACAAGGT<br>GAAAAAGATCGATGTTATTAAACGGCGAACTGCACCGATAAGAGAAGCCGAAG<br>CTGTTTGTGGAGTAATGCTAGAAGATGGTTCTTCTTGTTTGGAGGATCCAATG<br>GAAGGAAGGAAGAGGTGTGAGTTGCACAAAGGTAGAAGAGTCAGAGTGGCATA<br>CAGTCGCAAAGTATCCTCTTCTAGCTCCACTTGCCAAGTTGCTATTCCAACTG<br>TTGAATCCATACCTCAACAAACTGCTAATCCAAGCAAACGAGATCAAGCCTGG<br>CAAACCAGTGCAGACCAATCCAAAAATCTGTCCACAAATGCAAAGGAGCCATC<br>TTGGCAAAGGAACAGCTTCAAAGCAAATGAGATGAAAATCGGAGAAGCTCCTA<br>CAGAAGATGAAGCATATGGAACCTCCCATGCAGAATCTCAGTTCCACGAAGAT<br>GAGCCTTGTGGAAGGAAGTGGTTTGAGCGGCTCAAAGCACAGAAATCAGCCAA<br>CGCACCATCGTCGAGAGGCCAAGGATGTCAGCCAAGAGAAGCAAACAACGACG<br>CATCAGCCTTATGTGGAGTAGTGACAGATAATGGATACTGCAAACTGGAACCG<br>GTGATAGGAAGGGAAAGATGCGAGGAGCACAGAGGAATTGAGGTCACTGGTGC<br>GTCATCGGCACCATGTTCCGGAAGGTCGGTATTGCCATCTGTCTGTGGAGCTC<br>GGGCATCCGATGGTTCACCTTGCAAGAATCAGCCAATCGCAAGGAGGAAGAGA<br>TGTGCGTTGCACAAAGGTCAAAGAGCGTGCTGCGCCTCCGCGCCATCAGTCAA<br>A |
| SEQ ID NO: 2<br>Protein sequence<br>of HvHRT<br>ID# AK362734 (cv.<br>Haruna Nijo) | MPAVAAARLKREDCPRTKHDSLESPWKVLVGPSDWEDHSAGKEGVQRYHTRNL<br>PDNFPGLYELGVARPSYDGVRARRNRSVVVVVVYLGQADNVRARLQQYGRTGS<br>HLDTGNPLAAVCKAEMNALTAGPGLFREVESRGYSMMERCALMGSKKAAEKTE<br>GQLLGVFDYAWNKLQNGACRREEILLKLEQGSNRLSLLSRVRHLKQRVFGEKA<br>GIKINSSGSVEISSSSMKNMLPRVRTFVGFRPRLVNSGDDLNEASDIHRKCTP<br>QANTAGKQAHRRSEGYKVKKIDVIKRRTAPIREAEAVCGVMLEDGSSCLEDPM<br>EGRKRCELHKGRRVRVAYSRKVSSSSSTCQVAIPTVESIPQQTANPSKRDQAW<br>QTSADQSKNLSTNAKEPSWORNSFKANEMKIGEAPTEDEAYGTSHAESQFHED<br>EPCGRKWFERLKAQKSANAPSSRGOGCQPREANNDASALCGVVTDNGYCKLEP<br>VIGRERCEEHRGIEVTGASSAPCSGRSVLPSVCGARASDGSPCKNQPIARRKR<br>CALHKGQRACCASAPSVK* |
| SEQ ID NO: 3<br>Coding sequence<br>of the HvHRT<br>gene of barley<br>mutant HENZ-2.<br>The exchange of G<br>to A results in a<br>W431Stop<br>mutation of the<br>protein | ATGCCTGCGGTCGCCGCTGCCAGATTGAAGCGGGAGGACTGCCCCCGCACCAA<br>ACACGATTCCCTCTTCTCCCCATGGAAGGTTCTTGTCGGGCCGTCGGACTGGG<br>AGGACCACTCCGCCGGCAAGGAGGGGGTCCAGAGGTATCACACACGCAACCTC<br>CCGGACAACTTCCCTGGCCTCTACGAGCTGGGCGTTGCAAGGCCTTCCTATGA<br>TGGTGTCAGGGCTCGCAGAAATCGATCAGTTGTCGTCGTGGTGGTATACCTCG<br>GGCAGGCCGATAATGTCAGGGCGAGGCTCCAGCAGTACGGGCGGACAGGGTCA<br>CACCTGGACACCGGGAATCCGTTGGCTGCTGTCTGTAAAGCTGAGATGAACGC<br>GCTCACGGCAGGACCTGGATTGTTCAGGGAAGTCTTCTCCAGAGGCTACTCTA<br>TGATGTTTCGATGTGCGCTGATGGGTTCCAAAAAGGCAGCTGAGAAGACTGAA<br>GGTCAGCTACTGGGAGTATTTGATTATGCATGGAATAAACTGCAGAATGGTGC<br>GTGTCGTCGCGAAGAAATACTGCTCAAGTTAGAACAGGGAAGCAATAGATTAT<br>CTTTGCTTAGCAGAGTCCGGCACTTAAAACAGAGGGTGTTTGGAGAGAAAGCA<br>GGTATAAAGATTAACAGCAGTGGGTCTGTTGAGATTTCATCTAGCAGTATGAA<br>AAATATGCTTCCAAGAGTCCGTACGTTTGTCGGCTTCAGGCCTCGTTTGGTTA<br>ACTCTGGCGACGATTTAAACGAGGCAAGTGATATTCACCGAAAATGCACACCT<br>CAGGCCAATACTGCTGGTAAACAAGCACATAGAAGGTCTGAAGGATACAAGGT<br>GAAAAAGATCGATGTTATTAAACGGCGAACTGCACCGATAAGAGAAGCCGAAG<br>CTGTTTGTGGAGTAATGCTAGAAGATGGTTCTTCTTGTTTGGAGGATCCAATG<br>GAAGGAAGGAAGAGGTGTGAGTTGCACAAAGGTAGAAGAGTCAGAGTGGCATA<br>CAGTCGCAAAGTATCCTCTTCTAGCTCCACTTGCCAAGTTGCTATTCCAACTG<br>TTGAATCCATACCTCAACAAACTGCTAATCCAAGCAAACGAGATCAAGCCTGG<br>CAAACCAGTGCAGACCAATCCAAAAATCTGTCCACAAATGCAAAGGAGCCATC<br>TTGGCAAAGGAACAGCTTCAAAGCAAATGAGATGAAAATCGGAGAAGCTCCTA<br>CAGAAGATGAAGCATATGGAACCTCCCATGCAGAATCTCAGTTCCACGAAGAT<br>GAGCCTTGTGGAAGGAAGTGATTTGAGCGGCTCAAAGCACAGAAATCAGCCAA<br>CGCACCATCGTCGAGAGGCCAAGGATGTCAGCCAAGAGAAGCAAACAACGACG<br>CATCAGCCTTATGTGGAGTAGTGACAGATAATGGATACTGCAAACTGGAACCG<br>GTGATAGGAAGGGAAAGATGCGAGGAGCACAGAGGAATTGAGGTCACTGGTGC<br>GTCATCGGCACCATGTTCCGGAAGGTCGGTATTGCCATCTGTCTGTGGAGCTC<br>GGGCATCCGATGGTTCACCTTGCAAGAATCAGCCAATCGCAAGGAGGAAGAGA<br>TGTGCGTTGCACAAAGGTCAAAGAGCGTGCTGCGCCTCCGCGCCATCAGTCAA<br>ATAA |
| SEQ ID NO: 4<br>Sequence of<br>mutant HvHRT of<br>barley mutant<br>HENZ-2. | MPAVAAARLKREDCPRTKHDSLESPWKVLVGPSDWEDHSAGKEGVQRYHTRNL<br>PDNFPGLYELGVARPSYDGVRARRNRSVVVVVVYLGQADNVRARLQQYGRTGS<br>HLDTGNPLAAVCKAEMNALTAGPGLFREVESRGYSMMERCALMGSKKAAEKTE<br>GQLLGVFDYAWNKLQNGACRREEILLKLEQGSNRLSLLSRVRHLKQRVFGEKA<br>GIKINSSGSVEISSSSMKNMLPRVRTFVGFRPRLVNSGDDLNEASDIHRKCTP<br>QANTAGKQAHRRSEGYKVKKIDVIKRRTAPIREAEAVCGVMLEDGSSCLEDPM<br>EGRKRCELHKGRRVRVAYSRKVSSSSSTCQVAIPTVESIPQQTANPSKRDQAW<br>QTSADQSKNLSTNAKEPSWORNSFKANEMKIGEAPTEDEAYGTSHAESQFHED<br>EPCGRK* |
| SEQ ID NO: 5<br>Coding sequence<br>of the HvHBL12 | ATGGAGCAGGGGGAGGAGGACGGGGACTGGATGATGGAGCCGGCGTCGGGGAA<br>GAAGGGCGGGGTGATGATCGACAGGAAGAAGCGCTTCAGCGAGGAGCAGATCA<br>AGTCGCTCGAGTCCATGTTCGCCACGCAGACCAAGCTGGAGCCCCGCCAGAAG |

| | Sequences |
|---|---|
| gene<br>ID# AK376953 (cv.<br>Haruna Nijo) | CTGCAGCTGGCCCGGGAGCTCGGCCTGCAGCCGCGCCAGGTCGCCATCTGGTT<br>CCAGAACAAGCGCGCGCGCTGGAAGTCCAAGCAGCTCGAGCGCCAGTACGCCG<br>CGCTCCGGGACGACTACGACGCCCTCCTCTCCAGCTACGACCAGCTCAAGAAG<br>GACAAGCAAGCGCTCGTCAACCAGCTGGAGAAGCTAGCAGAGATGCTGCGGGA<br>GCCGGGCGGGGCCAAGTGCGGAGATAATGCCGGCGCTGCTGACAGGGACAACA<br>TGCGCCTGGCCGTGGCCGGCATGAGCATGAAGGACGAGTTCGCGGACGCTGCC<br>GGGGCCAGCAAGCTCTACTCGGCGTCTGCCGAGGGCTGCGGCGGCAGCGGCAA<br>GCTCTCCCTCTTCGGCGAGGAGGATGACGACGCGGGCCTCTTCCTCCGGCCCT<br>CGCTGCAGCTGCCAACCGCGCACGACGGCGGCTTCACGGCGTCGGGGCCGGCC<br>GAGTACCAGCAGCAGTCGCCGTCGTCGTTCCCGTTCCACTCGAGCTGGCCGTC<br>GTCCGCGACGGAGCAGACCTGCAGCAGCTCCCAATGGTGGGAATTCGAGTCCC<br>CGAGCGAGTAA |
| SEQ ID NO: 6<br>Protein sequence<br>of HvHBL12<br>ID# AK362734 (cv.<br>Haruna Nijo) | MEQGEEDGDWMMEPASGKKGGVMIDRKKRFSEEQIKSLESMFATQTKLEPRQK<br>LQLARELGLQPRQVAIWFQNKRARWKSKQLERQYAALRDDYDALLSSYDQLKK<br>DKQALVNQLEKLAEMLREPGGAKCGDNAGAADRDNMRLAVAGMSMKDEFADAA<br>GASKLYSASAEGCGGSGKLSLFGEEDDDAGLFLRPSLQLPTAHDGGFTASGPA<br>EYQQQSPSSFPFHSSWPSSATEQTCSSSQWWEFESPSE* |
| SEQ ID NO: 7<br>Genomic DNA<br>sequence ID#<br>morex_contig_568<br>55 (exons in Italic<br>and Bold) | GAGACGGGAGACCCGGCTACGCATGCACGCCACCGCGCTCCATTGGCCGCCCC<br>GTTGCCATCACCGCGCCCATCGCTCCATCCCCGATTAAACTACTCCATATCG<br>CTAGTAAGCAGAAGCAGAATCGATCCATCACACCAAGCTAGCTAGCCTCCTAG<br>CTCGCTCGCTCGCCCGCACACCCGCGATCCATTCTGCTTCTTCCCCTTCCTTC<br>CCACTCCGGATCAGGTGCATGACCACCGGCGAGACCTAGCTAGGTAGGTAGGG<br>AGGGAGGGAGGG*ATGGAGCAGGGGAGGAGGACGGGGACTGGATGATGGAGCC<br>GGCGTCGGGGAAGAAGGGCGGGGTGATGATCGACAGGAAGAAGCGCTTCAGCG<br>AGGAGCAGATCAAGTCGCTAGAGTCCATGTTCGCCACGCAGACCAAGCTGGAG<br>CCCCGCCAGAAGCTGCAGCTGGCCCGGGAGCTCGGCCTGCAGCCGCGCCAGGT<br>CGCCATCTGGTTCCAGAACAAGCGCGCGCGCTGGAAGTCCAAGCAGCTCGAGC<br>GCCAGTACGCCGCGCTTCGGGACGACTACGACGCCCTCCTCTCCAGCTACGAC<br>CAGCTCAAGAAGGACAAGCAAGCGCTCGTCAACCAG*GTATATACTCCTATGTC<br>TGTCTGTCTGTGCTACGTACCGTGTGTTTCTCCGTGCTCTCCGCTCGGTGGCG<br>TGGAGCTCGTGGTGCCTCTGGCTAATGCATGGTCGACGGGTTTCTTGCCTTGC<br>GTGTCCGTGCA*CTGGAGAAGCTAGCAGAGATGCTGCGGGAGCCGGGCGGGGC<br>CAAGTGCGGAGATAATGCCGGCGCTGCTGACAGGGACGACGTGCGCCTGGCCG<br>TGGCCGGCATGAGCATGAAGGACGAGTTCGCGGACGCTGCCGGGGCCAGCAAG<br>CTCTACTCGGCGTCTGCCGAGGGCTGCGGCGGCAGCGGCAAGCTCTCCCTCTT<br>CGGCGAGGACGATGACGACGCGGGCCTCTTCCTCCGGCCCTCGCTGCAGCTGC<br>CAACCGCGCACGACGGCGGCTTCACGGCGTCGGGGCCGGCCGAGTACCAGCAG<br>CAGTCGCCGTCGTCGTTCCCGTTCCACTCGAGCTGGCCGTCGTCCGCGACGGA<br>GCAGACCTGCAGCAGCTCCCAATGGTGGGAATTCGAGTCCCCGAGCGAGTAA*G<br>TAGAGCCATCGGTCAAGCACCATGCAAGGAATCGCCGACGTGATCGACCATGC<br>AACAGATCAGTGTTCCTAACACAGAGCACTATACTGCCGATCGAATCCGTGGA<br>GAAGACGACGGCGCGATCGATCATATGCAACCGAAGATGGTGGTGTCAAGTGT<br>GTACATAGCTCGAAACCCAGGTCTGTCCAGTCCAGTACGTCCAGGCAGCCTCT<br>TCCTTCTCAATCAGCAGTCAGCACGCCATTTTTCTTCACCCTCTTCCTCTTTA<br>AGAATCACTTGCTCTTGTCAATTACCTGCCACACCGTGTAATCCACAGGGAAA<br>CTAGTCACAAAACCAAATTATAGAGACCGATCTTCAGATGCAAGTGCATGCAA<br>CTATTTAGC |
| SEQ ID NO: 8<br>Coding sequence<br>of the mutant<br>HvHBL12 gene of<br>barley mutant<br>HENZ-10.<br>Sequence shows<br>the exchange of G<br>to A thus encoding<br>mutant protein<br>(W228Stop).<br>Based on ID#<br>AK376953 (cv.<br>Haruna Nijo) | ATGGAGCAGGGGAGGAGGACGGGGACTGGATGATGGAGCCGGCGTCGGGGAA<br>GAAGGGCGGGGTGATGATCGACAGGAAGAAGCGCTTCAGCGAGGAGCAGATCA<br>AGTCGCTCGAGTCCATGTTCGCCACGCAGACCAAGCTGGAGCCCCGCCAGAAG<br>CTGCAGCTGGCCCGGGAGCTCGGCCTGCAGCCGCGCCAGGTCGCCATCTGGTT<br>CCAGAACAAGCGCGCGCGCTGGAAGTCCAAGCAGCTCGAGCGCCAGTACGCCG<br>CGCTCCGGGACGACTACGACGCCCTCCTCTCCAGCTACGACCAGCTCAAGAAG<br>GACAAGCAAGCGCTCGTCAACCAGCTGGAGAAGCTAGCAGAGATGCTGCGGGA<br>GCCGGGCGGGGCCAAGTGCGGAGATAATGCCGGCGCTGCTGACAGGGACAACA<br>TGCGCCTGGCCGTGGCCGGCATGAGCATGAAGGACGAGTTCGCGGACGCTGCC<br>GGGGCCAGCAAGCTCTACTCGGCGTCTGCCGAGGGCTGCGGCGGCAGCGGCAA<br>GCTCTCCCTCTTCGGCGAGGAGGATGACGACGCGGGCCTCTTCCTCCGGCCCT<br>CGCTGCAGCTGCCAACCGCGCACGACGGCGGCTTCACGGCGTCGGGGCCGGCC<br>GAGTACCAGCAGCAGTCGCCGTCGTCGTTCCCGTTCCACTCGAGCTG<u>A</u>CCGTC<br>GTCCGCGACGGAGCAGACCTGCAGCAGCTCCCAATGGTGGGAATTCGAGTCCC<br>CGAGCGAGTAA |
| SEQ ID NO: 9<br>Protein sequence<br>of mutant<br>HvHBL 12 from<br>barley mutant<br>HENZ-10. | MEQGEEDGDWMMEPASGKKGGVMIDRKKRFSEEQIKSLESMFATQTKLEPRQK<br>LQLARELGLQPRQVAIWFQNKRARWKSKQLERQYAALRDDYDALLSSYDQLKK<br>DKQALVNQLEKLAEMLREPGGAKCGDNAGAADRDNMRLAVAGMSMKDEFADAA<br>GASKLYSASAEGCGGSGKLSLFGEEDDDAGLFLRPSLQLPTAHDGGFTASGPA<br>EYQQQSPSSFPFHSS* |
| SEQ ID NO: 10<br>Coding sequence<br>of the WRKY38<br>gene | ATGGATCCATGGATGGGCAGCCAGCCATCCCTGAGCCTCGACCTGCACGTCGG<br>CCTACCGCCGATGGGGCACCCGCACCACCACCAGAGCCAATACCAGGCGCCGC<br>CGATGATCGCGCTGGCCAAGCCCAAGATCCTCGTGGAGGAGAACTTCATGCCA<br>CTCAAGAAGGACCCTGAGGTTGCGGTTCTTGAGTCGGAGCTACAGCGGGTGAG |

| Sequences | |
|---|---|
| Accession number AJ536667.1 Barley cv. Ingrid | CGAGGAGAACCGGCGGCTGGGCGAGATGCTCAGGGAGGTGGCCTCCAAGTACG AGGCCCTGCAGGGCCAGTTCACCGACGTGGTCACGGCCGGCGGCAACAACAAC CACTACCACAACCAGCCGTCCTCCGCGTCGGAGGGCGGGTCGGTGTCGCCGTC GAGGAAGCGCAAGAGCGAGGAGAGCCTCGGCACGCCGCCACCGTCGCATACTC AGCAGCAGCACTATGCCGCCGGCCTCGCGTACGCGGTGGCGCCGGACCAGGCG GAGTGCACGTCCGGCGAGCCGTGCAAGCGCATCCGGGAGGAGTGCAAGCCCGT CATCTCCAAGCGCTACGTCCACGCCGACCCCTCCGACCTCAGCCTGGTGGTGA AGGACGGGTACCAATGGCGCAAGTACGGGCAGAAGGTGACCAAGGACAACCCA TGCCCCAGAGCCTACTTCCGGTGCTCCTTCGCCCCCGGCTGCCCCGTCAAGAA GAAGGTGCAGAGGAGCGCCGAGGACAAGACCATACTCGTGGCGACGTACGAGG GCGAGCACAACCACACCCAGCCCCCGCCGTCGCAGCCGCAGCAGCAGAACGAC GGCTCCGGCGCCGGCAAGAACGCCGGGAACGGGAAGCCGCCCCAGGCGCCGGC CACGCCTCACCACCCGCAGCAGCAGCACAAGCAGGAAGCGGCAGCGGTCGTCG TCAGCGGCGAATCGGCCGCGGCGGCGTCCGAGCTGATCCGGCGCAACCTGGCG GAGCAGATGGCCATGACGCTGACGAGGGACCCCAGCTTCAAGGCGGCGCTGGT CACCGCGCTCTCCGGCCGGATCCTCGAGCTCTCGCCGACCAGGGACATCAATT AA |
| SEQ ID NO: 11 Protein sequence of WRKY38 | MDPWMGSQPSLSLDLHVGLPPMGHPHHHQSYQAPPMIALAKPKILVEENEMP LKKDPEVAVLESELQRVSEENRRLGEMLREVASKYEALQGQFTDVVTAGGNNN HYHNQPSSASEGGSVSPSRKRKSEESLGTPPPSHTQQQHYAAGLAYAVAPDQA ECTSGEPCKRIREECKPVISKRYVHADPSDLSLVVKDGYQWRKYGQKVTKDNP CPRAYFRCSFAPGCPVKKKVQRSAEDKTILVATYEGEHNHTQPPPSQPQQQND GSGAGKNAGNGKPPQAPATPHHPQQQHKQEAAAVVVSGESAAAASELIRRNLA EQMAMTLTRDPSFKAALVTALSGRILELSPTRDIN* |
| SEQ ID NO: 12 Protein sequence of WRKY38 | MDPWMGSQPSLSLDLHVGLPPMGHPHHHQSYQAPPMIALAKPKILVEENEMP LKKDPEVAVLESELQRVSEENRRLGEMLREVASKYEALQGQFTDVVTAGGNNN HYHNQPSSASEGGSVSPSRKRKSEESLGTPPPSHTQQQHYAAGLAYAVAPDQA ECTSGEPCKRIREECKPVISKRYVHADPSDLSLVVKDGYQWRKYGQKVTKDNP CPRAYFRCSFAPGCPVKKKVQRSAEDKTILVATYEGEHNHTQPPPSQPQQQND GSGAGKNAGNGKPPQAPATPHHPQQQHKQEAAAVVVSGESAAAASELIRRNLA EQMAMTLTRDPSFKAALVTALSGRILELSPTRDIN |
| SEQ ID NO: 13 Coding sequence of mutant WRKY38 gene of HENZ-50 Based on Accession number AJ536667.1 Barley cv. Ingrid. Sequence shows the exchange of G to A thus encoding mutant protein (W200Stop). | ATGGATCCATGGATGGGCAGCCAGCCATCCCTGAGCCTCGACCTGCACGTCGG CCTACCGCCGATGGGGCACCCGCACCACCACCAGAGCCAATACCAGGCGCCGC CGATGATCGCGCTGGCCAAGCCCAAGATCCTCGTGGAGGAGAACTTCATGCCA CTCAAGAAGGACCCTGAGGTTGCGGTTCTTGAGTCGGAGCTACAGCGGGTGAG CGAGGAGAACCGGCGGCTGGGCGAGATGCTCAGGGAGGTGGCCTCCAAGTACG AGGCCCTGCAGGGCCAGTTCACCGACGTGGTCACGGCCGGCGGCAACAACAAC CACTACCACAACCAGCCGTCCTCCGCGTCGGAGGGCGGGTCGGTGTCGCCGTC GAGGAAGCGCAAGAGCGAGGAGAGCCTCGGCACGCCGCCACCGTCGCATACTC AGCAGCAGCACTATGCCGCCGGCCTCGCGTACGCGGTGGCGCCGGACCAGGCG GAGTGCACGTCCGGCGAGCCGTGCAAGCGCATCCGGGAGGAGTGCAAGCCCGT CATCTCCAAGCGCTACGTCCACGCCGACCCCTCCGACCTCAGCCTGGTGGTGA AGGACGGGTACCAATGACGCAAGTACGGGCAGAAGGTGACCAAGGACAACCCA TGCCCCAGAGCCTACTTCCGGTGCTCCTTCGCCCCCGGCTGCCCCGTCAAGAA GAAGGTGCAGAGGAGCGCCGAGGACAAGACCATACTCGTGGCGACGTACGAGG GCGAGCACAACCACACCCAGCCCCCGCCGTCGCAGCCGCAGCAGCAGAACGAC GGCTCCGGCGCCGGCAAGAACGCCGGGAACGGGAAGCCGCCCCAGGCGCCGGC CACGCCTCACCACCCGCAGCAGCAGCACAAGCAGGAAGCGGCAGCGGTCGTCG TCAGCGGCGAATCGGCCGCGGCGGCGTCCGAGCTGATCCGGCGCAACCTGGCG GAGCAGATGGCCATGACGCTGACGAGGGACCCCAGCTTCAAGGCGGCGCTGGT CACCGCGCTCTCCGGCCGGATCCTCGAGCTCTCGCCGACCAGGGACATCAATT AA |
| SEQ ID NO: 14 Protein sequence of mutant WRKY38 from barley mutant HENZ-50. | MDPWMGSQPSLSLDLHVGLPPMGHPHHHQSYQAPPMIALAKPKILVEENEMP LKKDPEVAVLESELQRVSEENRRLGEMLREVASKYEALQGQFTDVVTAGGNNN HYHNQPSSASEGGSVSPSRKRKSEESLGTPPPSHTQQQHYAAGLAYAVAPDQA ECTSGEPCKRIREECKPVISKRYVHADPSDLSLVVKDGYQ* |

Items

The invention may for example be as defined in the following items:

1. A barley plant or a part thereof with high α-amylase activity, wherein said barley plant
   carries a mutation in the HvHRT gene leading to loss of HvHRT function; and/or
   carries at least one α-amylase gene comprising a mutant α-amylase promoter comprising a mutation in the GARE box; and/or
   carries at least four α-amylase genes comprising a GARE box of the sequence TAACAAA; and/or
   carries at least one α-amylase gene in the amy2 cluster comprising a mutant α-amylase promoter comprising a mutation in the GARE box or which has the sequence TAACAAA; and/or
   carries a mutation in the HvHBL12 gene leading to loss of HvHBL12 function; and/or
   carries at least four α-amylase genes comprising an α-amylase promoter comprising a non-standard tan- dem repeat W-box, wherein said non-standard tandem repeat W-box comprises the sequence (TGAC(C)$_n$(X)$_m$TTGACC) (SEQ ID NO: 38), wherein one or more of the specific nucleotides have been substituted or deleted, and wherein X may be any nucleotide, n is 0 or 1 and m is an integer in the range of 0 to 20; and/or carries at least one α-amylase gene in the amy2 cluster comprising an α-amylase promoter comprising a non-standard tandem repeat W-box;

carries a mutation in the WRKY38 gene leading to loss of WRKY38 function.

2. A barley plant or a part thereof, wherein said barley plant
   a. carries a mutation in the HvHRT gene resulting in a mutant HvHRT gene encoding a mutant HvHRT protein lacking one or more of the amino acids of SEQ ID NO:2 or a mutation resulting in deletion of at least the coding region of the HvHRT gene, wherein the coding region of the HvHRT gene encodes a polypeptide of SEQ ID NO:2; and/or
   b. carries at least one α-amylase gene comprising a mutant α-amylase promoter comprising a mutation in the GARE box; and/or
   c. carries at least four α-amylase genes comprising a GARE box of the sequence TAACAAA; and/or
   d. carries at least one α-amylase gene in the amy2 cluster comprising a mutant α-amylase promoter comprising a mutation in the GARE box or which has the sequence TAACAAA; and/or
   e. carries a mutation in the HvHBL12 gene resulting in a mutant HvHBL12 gene encoding a mutant HvHBL 12 protein lacking one or more of the amino acids of SEQ ID NO:6 or a mutation resulting in deletion of at least the coding region of the HvHBL12 gene, wherein the coding region of the HvHBL12 gene encodes a polypeptide of SEQ ID NO: 6; and/or
   f. carries at least four α-amylase genes comprising an α-amylase promoter comprising a non-standard tandem repeat W-box, wherein said non-standard tandem repeat W-box comprises the sequence (TGAC(C)$_n$(X)$_m$TTGACC) (SEQ ID NO: 38), wherein one or more of the specific nucleotides have been substituted or deleted, and wherein X may be any nucleotide, n is 0 or 1 and m is an integer in the range of 0 to 20; and/or
   g. carries at least one α-amylase gene in the amy2 cluster comprising an α-amylase promoter comprising a non-standard tandem repeat W-box; and/or
   h. carries a mutation in the WRKY38 gene resulting in a mutant WRKY38 gene encoding a mutant WRKY38 protein lacking one or more of the amino acids present in both SEQ ID NO:11 and SEQ ID NO: 12 or a mutation resulting in deletion of at least the coding region of the WRKY38 gene, wherein the coding region of the WRKY38 gene encodes a polypeptide of SEQ ID NO:11 or SEQ ID NO:12.

3. The barley plant according to any one of the preceding items, wherein the said barley plant carries a mutation in the HvHRT gene.

4. The barley plant according to item 3, wherein the mutation is:
   a mutation resulting in a mutant HvHRT gene encoding a mutant HvHRT protein lacking at least the amino acids corresponding to amino acids 527 to 530 of SEQ ID NO:2
   a mutation resulting in deletion of the HvHRT gene 5. The barley plant according to any one of items 3 to 4, wherein the mutation introduces a premature stop codon in the HvHRT gene.

6. The barley plant according to any one of items 3 to 5, wherein the mutation is a mutation in a splice site of the HvHRT gene.

7. The barley plant according to any one of items 3 to 6, wherein the barley plant comprises a mutant HvHRT gene encoding a mutant HvHRT protein lacking at least amino acids 463 to 491 of SEQ ID NO:2.

8. The barley plant according to any one of items 3 to 7, wherein the barley plant comprises a mutant HvHRT gene encoding a mutant HvHRT protein lacking at least amino acids 509 to 539 of SEQ ID NO:2.

9. The barley plant according to any one of items 3 to 8, wherein the barley plant comprises a mutant HvHRT gene encoding a mutant HvHRT protein lacking at least the 21 most C-terminal amino acids, for example at least the 39 most C-terminal amino acids, such as at least the 85 most C-terminal amino acids, for example at least the 100 most C-terminal amino acids of SEQ ID NO:2.

10. The barley plant according to any one of items 3 to 9, wherein the barley plant comprises a mutant HvHRT gene encoding a mutant HvHRT protein lacking at least the 118 most C-terminal amino acids of SEQ ID NO:2.

11. The barley plant according to any one of items 3 to 10, wherein the barley plant comprises a mutant HvHRT gene encoding a truncated HvHRT protein comprising an N-terminal fragment of HvHRT comprising at the most the 526 N-terminal amino acids of SEQ ID NO:2, for example at the most the 508 N-terminal amino acids of SEQ ID NO:2, such as at the most the 462 N-terminal amino acids of SEQ ID NO:2, preferably at the most the 431 N-terminal amino acids of SEQ ID NO:2.

12. The barley plant according to any one of items 3 to 11, wherein the barley plant, comprises a mutant HvHRT gene carrying a premature stop codon in any one of codons 1 to 431.

13. The barley plant according to any one of items 3 to 12, wherein the barley plant, comprises a mutant HvHRT gene carrying a premature stop codon in 431 of SEQ ID NO:1.

14. The barley plant according to any one of items 3 to 13, wherein the barley plant comprises a mutant HvHRT gene encoding a mutant HvHRT protein, wherein said mutant HvHRT protein carries a W431stop mutation of SEQ ID NO: 2.

15. The barley plant according to any one of items 3 to 14, wherein the barley plant comprises a mutant HvHRT gene comprising a G→A mutation of the nucleotide 1293 of the HvHRT coding sequence of SEQ ID NO:1

16. The barley plant according to any one of items 3 to 15, wherein the barley plant is the barley plant deposited under accession number NCIMB 43270 with NCIMB or progeny thereof.

17. The barley plant according to any one of items 3 to 12, wherein the barley plant, comprises a mutant HvHRT gene carrying a premature stop codon in 170 of SEQ ID NO:1.

18. The barley plant according to any one of items 3 to 12, wherein the barley plant comprises a mutant HvHRT gene encoding a mutant HvHRT protein, wherein said mutant HvHRT protein carries a W170stop mutation of SEQ ID NO: 2.

19. The barley plant according to any one of items 3 to 12, wherein the barley plant comprises a mutant HvHRT gene comprising a G→A mutation of the nucleotide 510 of the HvHRT coding sequence of SEQ ID NO:1

20. The barley plant according to any one of items 3 to 12, wherein the barley plant, comprises a mutant HvHRT gene carrying a premature stop codon in 371 of SEQ ID NO:1.
21. The barley plant according to any one of items 3 to 12, wherein the barley plant comprises a mutant HvHRT gene encoding a mutant HvHRT protein, wherein said mutant HvHRT protein carries a W371stop mutation of SEQ ID NO: 2.
22. The barley plant according to any one of items 3 to 12, wherein the barley plant comprises a mutant HvHRT gene comprising a G→A mutation of the nucleotide 1113 of the HvHRT coding sequence of SEQ ID NO:1
23. The barley plant according to any one of items 3 to 22, wherein the barley plant, comprises a mutant HvHRT gene encoding the polypeptide of SEQ ID NO:4.
24. The barley plant according to any one of items 3 to 23, wherein the barley plant, comprises a mutant HvHRT gene comprising the coding sequence of SEQ ID NO: 3.
25. The barley plant according to any one of items 3 to 24, wherein the barley plant comprises less than 10% mutant or wild type HvHRT mRNA compared to a barley plant comprising a wild type HvHRT gene, but otherwise of the same genotype, wherein HvHRT mRNA is RNA encoding a polypeptide of SEQ ID NO: 2 or a functional homologue thereof, and a wild type HvHRT gene is a gene encoding the polypeptide of SEQ ID NO:2 or a functional homologue thereof, wherein said functional homologue shares at least 95% sequence identity with SEQ ID NO:2.
26. The barley plant according to any one of items 2 to 25, wherein the mutation in the HvHRT gene is a mutation causing a total loss of HvHRT function.
27. The barley plant according to any one of the preceding items, wherein the barley plant comprises at least one α-amylase gene comprising a mutant α-amylase promoter comprising a mutation in the GARE box, wherein one of the nucleotides TAACARA have been either substituted or deleted.
28. The barley plant according to any one of the preceding items, wherein the barley plant comprises at least two α-amylase genes, such as at least three α-amylase genes, for example at least 4 α-amylase genes comprising said mutant α-amylase promoter.
29. The barley plant according to any one of the preceding items, wherein said barley plant comprises at least five α-amylase genes comprising a GARE box of the sequence TAACAAA.
30. The barley plant according to any one of the preceding items, wherein said barley plant comprises at least six, such as at least seven α-amylase genes comprising a GARE box of the sequence TAACAAA.
31. The barley plant according to any one of the preceding items, wherein the barley plant is a spring barley variety having a high yield.
32. The barley plant according to any one of the preceding items, wherein said barley plant comprises at least one, such as at least two, for example at least three α-amylase genes in the amy2 cluster comprising a GARE box of the sequence TAACAAA.
33. The barley plant according to any one of items 27 to 32, wherein said barley plant further carries a mutation in the HvHRT gene, wherein said mutation is the mutation according to any one of items 3 to 26.
34. The barley plant according to any one of items 3 to 33, wherein the barley plant has an α-amylase activity of at least 16 U/g 48 h after initiation of germination.
35. The barley plant according to any one of items 3 to 34, wherein the barley plant has an α-amylase activity of at least 140 U/g, such as at least 150 U/g, for example at least 160 U/g, such as at least 170 U/G 48 h after initiation of germination, provided that said barley plant is either hull-less or at least part of the hull has been removed prior to initiation of germination.
36. The barley plant according to any one of items 3 to 35, wherein the barley plant has a limit dextrinase of at least 30 mU/g, such as at least 35 mU/g, for example at least 40 mU/g 48 h after initiation of germination, provided that said barley plant is either hull-less or at least part of the hull has been removed.
37. The barley plant according to any one of items 1 to 2, wherein the said barley plant carries a mutation in the HvHBL12 gene.
38. The barley plant according to item 37, wherein the mutation is:
   a. a mutation resulting in a mutant HvHBL12 gene encoding a mutant HvHBL 12 protein lacking one or more amino acids of SEQ ID NO:6 or a functional homologue thereof sharing at least 95% sequence identity thereto; or
   b. a mutation resulting in deletion of the HvHBL12 gene
39. The barley plant according to any one of items 37 to 38, wherein the mutation introduces a premature stop codon in the HvHBL12 gene.
40. The barley plant according to any one of items 37 to 39, wherein the mutation is a mutation in a splice site of the HvHBL12 gene.
41. The barley plant according to any one of items 37 to 40, wherein the barley plant comprises a mutant HvHBL12 gene encoding a mutant HvHBL12 protein lacking at least the 10 most C-terminal amino acids, such as at least the 20 most C-terminal amino acids of SEQ ID NO:6 or a functional homologue thereof sharing at least 95% sequence identity therewith.
42. The barley plant according to any one of items 37 to 41, wherein the barley plant comprises a mutant HvHBL12 gene encoding a mutant HvHBL12 protein lacking at least the 22 most C-terminal amino acids of SEQ ID NO:6 or a functional homologue thereof sharing at least 95% sequence identity therewith.
43. The barley plant according to any one of items 37 to 42, wherein the barley plant comprises a mutant HvHBL12 gene encoding a truncated HvHBL12 protein comprising an N-terminal fragment of HvHBL12 comprising at the most the 228 N-terminal amino acids of SEQ ID NO:6 or a functional homologue thereof sharing at least 95% sequence identity therewith.
44. The barley plant according to any one of items 37 to 43, wherein the barley plant, comprises a mutant HvHBL12 gene carrying a premature stop codon in any one of codons 1 to 228.
45. The barley plant according to any one of items 37 to 44, wherein the barley plant, comprises a mutant HvHBL12 gene carrying a premature stop codon in 228 of SEQ ID NO:5.
46. The barley plant according to any one of items 37 to 45, wherein the barley plant comprises a mutant HvHBL12 gene encoding a mutant HvHBL12 protein, wherein said mutant HvHBL 12 protein carries a W228stop mutation of SEQ ID NO: 6.

47. The barley plant according to any one of items 37 to 46, wherein the barley plant comprises a mutant HvHBL12 gene comprising a G→A mutation of the nucleotide 684 of the HvHBL12 coding sequence of SEQ ID NO:5.

48. The barley plant according to any one of items 37 to 47, wherein the barley plant is the barley plant deposited under accession number NCIMB 43271 with NCIMB or progeny thereof.

49. The barley plant according to any one of items 37 to 48, wherein the barley plant, comprises a mutant HvHBL12 gene encoding the polypeptide of SEQ ID NO: 9 or of SEQ ID NO:9 carrying one or more of the polymorphisms N141D, M142V or E184D.

50. The barley plant according to any one of items 37 to 49, wherein the barley plant, comprises a mutant HvHBL12 gene comprising the coding sequence of SEQ ID NO:8.

51. The barley plant according to any one of items 37 to 50, wherein the barley plant comprises less than 10% HvHBL12 mRNA compared to a barley plant comprising a wild type HvHBL12 gene, but otherwise of the same genotype, wherein HvHBL12 mRNA is RNA encoding a polypeptide of SEQ ID NO:6 or a functional homologue thereof, and a wild type HvHRT gene is a gene encoding the polypeptide of SEQ ID NO:6 or a functional homologue thereof, wherein said functional homologue shares at least 95% sequence identity with SEQ ID NO: 6.

52. The barley plant according to any one of items 37 to 51, wherein the mutation in the HvHBL12 gene is a mutation causing a total loss of HvHBL12 function.

53. The barley plant according to any one of items 37 to 52, wherein said barley plant further carries a mutation in the HvHRT gene, wherein said mutation is the mutation according to any one of items 3 to 26 and/or said barley further comprises at least one α-amylase gene according to any one of items 27 to 32.

54. The barley plant according to any one of items 1 to 2, wherein the said barley plant carries a mutation in the HvWRKY38 gene.

55. The barley plant according to item 54, wherein the mutation is:
  a. a mutation resulting in a mutant HvWRKY38 gene encoding a mutant HvWRKY38 protein lacking at least one of the amino acids 200 to 206, 220, 226, 250 and/or 252 of SEQ ID NO:11 or SEQ ID NO: 12;
  b. a mutation resulting in deletion of the HvWRKY38 gene 56. The barley plant according to any one of items 54 to 55, wherein the mutation introduces a premature stop codon in the HvWRKY38 gene.

57. The barley plant according to any one of items 54 to 56, wherein the mutation is a mutation in a splice site of the HvWRKY38 gene.

58. The barley plant according to any one of items 54 to 57, wherein the barley plant comprises a mutant HvWRKY38 gene encoding a mutant HvWRKY38 protein lacking at least amino acids 200 to 206 of SEQ ID NO: 11 OR SEQ ID NO: 12.

59. The barley plant according to any one of items 54 to 58, wherein the barley protein lacking at least the 102 most C-terminal amino acids, for example at least the 104 most C-terminal amino acids, such as at least the 128 most C-terminal amino acids, for example at least the 134 most C-terminal amino acids of SEQ ID NO: 11 OR SEQ ID NO: 12.

60. The barley plant according to any one of items 54 to 59, wherein the barley plant comprises a mutant HvWRKY38 gene encoding a mutant HvWRKY38 protein lacking at least the 154 most C-terminal amino acids of SEQ ID NO: 11 OR SEQ ID NO:12.

61. The barley plant according to any one of items 54 to 60, wherein the barley plant comprises a mutant HvWRKY38 gene encoding a truncated HvWRKY38 protein comprising an N-terminal fragment of HvWRKY38 comprising at the most the 251 N-terminal amino acids of SEQ ID NO: 11 OR SEQ ID NO: 12, for example at the most the 249 N-terminal amino acids of SEQ ID NO: 11 OR SEQ ID NO: 12, such as at the most the 225 N-terminal amino acids of SEQ ID NO: 11 OR SEQ ID NO: 12, for example at the most the 219 N-terminal amino acids of SEQ ID NO: 11 OR SEQ ID NO: 12, preferably at the most the 199 N-terminal amino acids of SEQ ID NO: 11 OR SEQ ID NO:12.

62. The barley plant according to any one of items 54 to 61, wherein the barley plant, comprises a mutant HvWRKY38 gene carrying a premature stop codon in any one of codons 1 to 200.

63. The barley plant according to any one of items 54 to 62, wherein the barley plant, comprises a mutant HvWRKY38 gene carrying a premature stop codon in any one of codons 1 to 200 of SEQ ID NO:10.

64. The barley plant according to any one of items 54 to 63, wherein the barley plant, comprises a mutant HvWRKY38 gene carrying a premature stop codon in 200 of SEQ ID NO:10.

65. The barley plant according to any one of items 54 to 64, wherein the barley protein, wherein said mutant HvWRKY38 protein carries a W200stop mutation of SEQ ID NO: 11 or 12.

66. The barley plant according to any one of items 54 to 65, wherein the barley plant comprises a mutant HvWRKY38 gene comprising a G-A mutation of the nucleotide 600 of the HvWRKY38 coding sequence of SEQ ID NO:10.

67. The barley plant according to any one of items 54 to 66, wherein the barley plant, comprises a mutant HvWRKY38 gene encoding the polypeptide of SEQ ID NO: 14 or a polypeptide of SEQ ID NO: 14, wherein amino acid 98 is Met.

68. The barley plant according to any one of items 54 to 67, wherein the barley plant, comprises a mutant HvWRKY38 gene comprising the coding sequence of SEQ ID NO:13.

69. The barley plant according to any one of items 54 to 68, wherein the barley plant comprises less than 10% mutant or wild type HvWRKY38 mRNA compared to a barley plant comprising a wild type HvWRKY38 gene, but otherwise of the same genotype, wherein HvWRKY38 mRNA is RNA encoding a polypeptide of SEQ ID NO: 11 or 12 or a functional homologue thereof, and a wild type HvWRKY38 gene is a gene encoding the polypeptide of SEQ ID NO: 11 or 12 or a functional homologue thereof, wherein said functional homologue shares at least 95% sequence identity with SEQ ID NO:11 or 12.

70. The barley plant according to any one of items 54 to 69, wherein the mutation in the HvWRKY38 gene is a mutation causing a total loss of HvWRKY38 function.

71. The barley plant according to any one of items 54 to 70, wherein said barley plant further carries a mutation in the HvHRT gene, wherein said mutation is the mutation according to any one of items 3 to 26 and/or said barley further comprises at least one α-amylase gene according to any one of items 27 to 32 and/or said barley plant further carries a mutation in the HvHBL12 gene, wherein said mutation is the according to any one of items 37 to 52.

72. The barley plant according to any one of the preceding items, wherein the barley plant comprises at least five α-amylase genes comprising an α-amylase promoter comprising a non-standard tandem repeat W-box.

73. The barley plant according to any one of the preceding items, wherein the barley plant comprises at least six, such as at least seven α-amylase genes comprising an α-amylase promoter comprising a non-standard tandem repeat W-box.

74. The barley plant according to any one of the preceding items, wherein the barley plant is a spring barley variety with a high yield.

75. The barley plant according to any one of the preceding items, wherein said barley plant comprises at least one, such as at least two, for example at least three α-amylase genes in the amy2 cluster comprising a non-standard tandem repeat W-box.

76. The barley plant according to any one of the preceding items, wherein the non-standard tandem repeat W-boxes individually are selected from the group consisting of (TGACR(X)$_m$YTGRCC); (SEQ ID NO: 39)

(TGACR(X)$_m$TTGACC); (SEQ ID NO: 40)

(TGACR(X)$_m$TTGAC); (SEQ ID NO: 41)

(TGAC(C)$_n$(X)$_m$YTGRCC); (SEQ ID NO: 42)

(TGAC(C)$_n$(X)$_m$CTGRCC); (SEQ ID NO: 43)

(TGAC(C)$_n$(X)mYTGGCC); (SEQ ID NO: 44)

(TGAC(C)$_n$(X)$_m$CTGACC); (SEQ ID NO: 45)

(TGAC(C)$_n$(X)$_m$TTGGCC); and (SEQ ID NO: 46)

(TGAC(C)$_n$(X)$_m$TTGATC). (SEQ ID NO: 47)

wherein R is either G or A, Y is either C or T, n is 0 or 1 and m is an integer in the range of 0 to 20.

77. The barley plant according to any one of the preceding items, wherein m is an integer in the range of 0 to 10.

78. The barley plant according to any one of the preceding items, wherein m is an integer in the range of 0 to 6.

79. The barley plant according to any one of the preceding items, wherein one or more α-amylase genes comprises a non-standard tandem repeat W-box individually selected from the following sequences:

TGACGGTCGTATTGACC; (SEQ ID NO: 31)

TGACAGTGGTATTGGCC; (SEQ ID NO: 32)

TGACAGTGGTACTGGCC; (SEQ ID NO: 33)

GTGACAGTGGTATTGGCC; (SEQ ID NO: 34)

TGACGGTCGTATTGATC; (SEQ ID NO: 35)

TGACCGTCGTATTGATC; and (SEQ ID NO: 36)

TTGACTTGATC. (SEQ ID NO: 37)

80. The barley plant according to any one of the preceding items, wherein the barley plant comprises an amy1_1 cluster, wherein at least one of the α-amylase promoters comprises a non-standard tandem repeat W-box comprising the sequence TTGATC.

81. The barley plant according to any one of the preceding items, wherein the barley plant comprises an amy1_1 cluster, wherein at least one of the α-amylase promoters comprises a non-standard tandem repeat W-box comprising the sequence CTGACGGTCGTATTGATC (SEQ ID NO:72).

82. The barley plant according to any one of the preceding items, wherein the barley plant comprises an amy1_1 cluster comprising the sequence shown as "HENZ-43 amy1_1" in FIG. 11A.

83. The barley plant according to any one of items 37 to 82, wherein the barley plant has an α-amylase activity of at least 100 U/g, such as at least 110 U/g 48 h after initiation of germination, provided that said barley plant is either hull-less or at least part of the hull has been removed prior to initiation of germination.

84. The barley plant according to any one of items 37 to 83, wherein the barley plant has a limit dextrinase of at least 20 mU/g 48 h after initiation of germination, provided that said barley plant is either hull-less or at least part of the hull has been removed prior to initiation of said germination.

85. The barley plant according to any one of the preceding items, wherein the barley plant has an α-amylase activity 48 h after initiation of germination, which is at least 105%, such as at least 110%, for example at least 120%, such as at least 150%, for example at least 170% of the α-amylase activity a barley plant, which does not carry said mutation but is otherwise of the same genotype.

86. The barley plant according to any one of the preceding items, wherein the barley plant has a yield, which is at least 90% of the yield of a barley plant not comprising said mutation, but otherwise of the same genotype.

87. The barley plant according to any one of the preceding items, wherein the barley plant has a TKW of at least 38 g, such as of at least 40 g.

88. The barley plant according to any one of the preceding items, wherein the barley plant has a starch content of at least 55% w/w, such as at least 60% w/w.

89. The barley plant according to any one of the preceding items, wherein the barley plant has a protein content of at least 9.5% w/w.

90. The barley plant according to any one of the preceding items, wherein the barley plant has a height, which is at least 90% of the height of a barley plant not comprising said mutation, but otherwise of the same genotype.
91. The barley plant according to any one of the preceding items, wherein the barley plant has a number of ears/m$^2$, which is at least 90% of the number of ears/m$^2$ of a barley plant not comprising said mutation, but otherwise of the same genotype.
92. The barley plant according to any one of the preceding items, wherein the barley plant is not subject to pre-harvest sprouting.
93. The barley plants according to any one of the preceding items, wherein kernels of said barley plant when harvested from barley plants having been subjected to regular spraying with water for 20 days, have a rate of germination which is the same or higher than the rate of germination of kernels of said barley plant not subjected to said spraying and harvested at maturity
94. The barley plant according to any one of the preceding items, wherein said part of the barley plant is kernels.
95. The barley plant according to any one of the preceding items or progeny thereof, wherein the barley plant has not exclusively been obtained by means of an essentially biological method.
96. The barley plant according to any one of the preceding items, wherein the barley plant has been prepared by a method comprising the following steps or is progeny of a plant prepared by a method comprising the following steps:
    Mutagenizing barley plants or parts thereof, for example with a chemical mutagenizing agent such as NaN$_3$.
    Selecting barley plants carrying any of the mutations described herein.
97. The barley plant according to any one of the preceding items, wherein the barley plant comprises at least two of, such as at least three of the following mutations or properties:
    a. carries a mutation in the HvHRT gene leading to loss of HvHRT function; and/or
    b. carries at least one α-amylase gene comprising a mutant α-amylase promoter comprising a mutation in the GARE box; and/or
    c. carries at least four α-amylase genes comprising a GARE box of the sequence TAACAAA; and/or
    d. carries at least one α-amylase gene in the amy2 cluster comprising a mutant α-amylase promoter comprising a mutation in the GARE box or which has the sequence TAACAAA; and/or
    e. carries a mutation in the HvHBL12 gene leading to loss of HvHBL 12 function; and/or
    f. carries at least four α-amylase genes comprising an α-amylase promoter comprising a non-standard tandem repeat W-box, wherein said non-standard tandem repeat W-box comprises the sequence (TGAC(C)$_n$(X)$_m$TTGACC) (SEQ ID NO: 38), wherein one or more of the specific nucleotides have been substituted or deleted, and wherein X may be any nucleotide, n is 0 or 1 and m is an integer in the range of 0 to 20; and/or
    g. carries at least one α-amylase gene in the amy2 cluster comprising an α-amylase promoter comprising a non-standard tandem repeat W-box;
    h. carries a mutation in the WRKY38 gene leading to loss of WRKY38 function.
98. The barley plant according to any one of the preceding items, wherein the barley plant comprises at least two of, such as at least three of the following mutations:
    a. a mutation in one or more α-amylase promoters, for example any of the mutations described herein above in the section "α-amylase and barley plants carrying a mutation in an α-amylase promoter",
    b. a mutation in the HvHRT gene, for example any of the mutations described herein above in the section "Barley plant carrying a mutation in the HRT gene"
    c. a mutation in the HvHBL12 gene, for example any of the mutations described herein above in the section "Barley plant carrying a mutation in the HvHBL12 gene"
    d. a mutation in the HvWRKY38 gene, for example any of the mutation described herein above in the section "Barley plant carrying a mutation in the WRKY38 gene"
99. The barley plant according to any one of the preceding items, wherein the barley plant comprises a mutation in one or more additional genes, for example one or more of the following mutations:
    a. A mutation in the gene encoding LOX-1 resulting in a total loss of functional LOX-1
    b. A mutation in the gene encoding LOX-2 resulting in a total loss of functional LOX-2
    c. A mutation in the gene encoding MMT resulting in a total loss of functional MMT
    d. A mutation in the gene encoding CsIF6, wherein said mutant gene encodes mutant CsIF6 protein with reduced CsIF6 activity.
100. A plant product comprising or prepared from the barley plant according to any one of the preceding items or a part thereof.
101. The plant product according to item 100, wherein the plant product is selected from the group consisting of barley flour, green malt and kiln dried malt.
102. The plant product according to any one of items 100 to 101, wherein the plant product is green malt or kiln dried malt comprising processed kernel(s) of said barley plant.
103. The plant product according to items 100 to 102, wherein the plant product is milled green malt or milled kiln dried malt.
104 The plant product according to items 100 to 101, wherein the plant product is barley flour.
105. The plant product according item 100, wherein the plant product is wort prepared from kernels of said barley plant and/or from green malt or kiln dried malt comprising processed kernel(s) of said barley plant.
106. The plant product according to item 100, wherein the plant product is a beverage prepared from said barley plant of parts thereof.
107. The beverage according to item 106, wherein said beverage is prepared from kernels of said barley plant and/or from green malt or kiln dried malt comprising processed kernel(s) of said barley plant.
108. The beverage according to any one of items 106 to 107, wherein the beverage is beer.
109. A method of preparing green malt, said method comprising the steps of
    (i) providing kernels of a barley plant according to any one of items 1 to 99;
    (ii) steeping said kernels;
    (iii) germinating the steeped kernels under predetermined conditions.

110. A method of preparing kiln dried malt, said method comprising the steps of
(i) providing kernels of a barley plant according to any one of items 1 to 99;
(ii) steeping said kernels;
(iii) germinating the steeped kernels under predetermined conditions;
(iv) drying said germinated kernels.
111. A method of producing a beverage, said method comprising the steps of:
(i) Providing kernels of a barley plant according to any one of items 1 to 99 and/or green malt or kiln dried malt according to item 102 to 103
(ii) Preparing an aqueous extract of said kernels and/or said malt
(iii) processing said aqueous extract into a beverage.
112. A method of producing an aqueous extract, said method comprising the steps of:
a. providing grains of a barley plant according to any one of items 1 to 99;
b. subjecting the barley grains to a step of germination thereby obtaining germinated grains, wherein said step of germination comprises incubating said grains in an aqueous solution until the grains have a water content of at least 30%, wherein at least 2 L $O_2$ per kg dry weight barley grains is passed through said aqueous solution per h;
c. finely dividing said germinated grains, while said germinated grains have a water content of at least 20%, with the proviso that said barley grains do not have a water content below 20 at any time between steps b) and c);
d. preparing an aqueous extract of said finely divided germinated grains, thereby producing an aqueous extract of the barley.
113. The method according to item 112, wherein the grains of the barley are submerged in the aqueous solution during the entire step of germination
114. The method according to any one of items 112 to 113, wherein the step of germination comprises
i. at least one step of incubating said grains in an aqueous solution, wherein at least 2 L $O_2$ per kg dry weight barley grains is passed through said aqueous solution per h; and
ii. at least one step of incubating said barley grains in air.
115. The method according to any one of items 112 to 114, wherein at least 3 L, more preferably at least 4 L, yet more preferably at least 5 L, even more preferably at least 6 L $O_2$ per kg dry weight of barley grains is passed through said aqueous solution per h.
116. The method according to any one of items 112 to 115, wherein said $O_2$ is comprised within a gas mixture, wherein the gas mixture is atmospheric air.
117. The method according to any one of items 112 to 116, wherein the entire step of germination does not exceed 72 h, more preferably does not exceed 60 h, even more preferably does not exceed 54 h.
118. The method according to any one of items 112 to 117, wherein the barley is a hulled barley, and the method comprises a step of removing at least part of said hull prior to incubating said grains in an aqueous solution.
119. A method for producing a beverage, said method comprising the steps of:
(i) preparing an aqueous extract by the method according to any one of items 112 to 118;
(ii) processing said extract into a beverage.
120. The method according to item 119, wherein step (iii) comprises the steps of:
a. heating said aqueous extract optionally in the presence of hops or hops extract;
b. cooling the aqueous extract;
c. fermenting said aqueous extract with yeast, thereby producing a fermented beverage.
121. The method according to any one of items 119 to 120, wherein the beverage is beer.
122. A method of preparing a barley plant with high α-amylase activity, the method comprising the steps of
a) providing barley kernels; and
b) randomly mutagenizing said barley kernels, thereby introducing at least one of the following mutations in at least one barley kernel:
a mutation in the HvHRT gene;
a mutation in one or more α-amylase promoters
a mutation in the HvHBL12 gene
a mutation in the WRKY38 gene
c) Selecting barley kernels or progeny thereof carrying at least one of said mutations.
123. The method according to item 122, wherein the mutation is as defined in any one of items 3 to 26, 27 to 32, 37 to 52, 54 to 70 and 72 to 82.

EXAMPLES

The invention is further illustrated by the following examples, which however should not be construed as limiting for the invention.

Example 1

Barley gene HvHRT is represented in the barley genome version 2012 as CDS under ID #MLOC_51005 (cv. Morex) or ID #AK362734 (cv. Haruna Nijo) and as genomic DNA on morex_contig_368180 (cv. Morex) (IBSC, 2012). In the barley genome version 2017 (Mascher et al., 2017), HvHRT is represented as CDS and protein sequence by ID #HORVU2Hr1G035630. In the barley genome version 2017, HvHRT is located on chromosome 2H at position 150.902.998 bp-150.911.087 bp. In the barley genome version 2017, HvHRT is annotated as effector of transcription2. In the barley genome version 2012, HvHRT is structured in three exons. The original sequence was deposited in NCBI under ID #AJ001317.1.

A barley mutant named HENZ-2 was identified and isolated as described in Examples 2 below. HENZ-2 carries a nucleotide substitution in the barley gene HvHRT resulting in a premature STOP codon in the coding sequence. The coding sequence of the HRT gene of the HENZ-2 mutant is provided herein as SEQ ID NO:3, whereas the sequence of the mutant protein encoded by the mutant HRT gene is provided as SEQ ID NO: 4.

The mutation results in an amino acid exchange from tryptophan 431 to STOP (W431Stop). The mutant background is cv. Paustian. The original mutant isolated was heterozygous for the polymorphism, but was later propagated to obtain homozygous mutants.

Example 2A ddPCR-Based Screening for Barley Mutants with Specific Mutations in the Gene for *Hordeum vulgare* Repressor of Transcription, HRT.

A barley plant carrying a specific mutation in the HvHRT gene was identified using the methods described in international patent application PCT/EP2017/065516.

ddPCR Assay

A unique ddPCR assay was designed, specifically to distinguish between the mutant allele and wild-type allele of HvHRT at nucleotide position 1293 in the wild-type coding sequence SEQ ID NO:1. As outlined above, several genetic sequences of barley HvHRT are available, and ddPCR assay used in this example was based on the genomic sequence of cv. Himalaya GenBank number NCBI: AJ001317.1. The mutant detection probe was complementary to the coding sequence, containing an A base at nucleotide position 1293. The reference detection probe was complementary to the coding sequence, containing a G base at nucleotide position 1293. Two flanking primers were designed to amplify the genomic sequence surrounding nucleotide 1293 in the coding sequence.

The following primers and probes were designed specifically for the HvHRT locus:

```
Target-specific forward primer (SEQ ID NO: 15):
5'- CACGAAGATGAGCCTTG- 3';

Target-specific reverse primer (SEQ ID NO: 16):
5'- TTGGCTGATTTCTGTGC- 3';

Mutant-specific detection probe (SEQ ID NO: 17):
5'- AAGTGATTTGAGCGGCT- 3' - labelled with 6-
carboxyfluorescein (FAM);

Reference-specific detection probe (SEQ ID NO: 18):
5'- AGGAAGTGGTTTGAGCG- 3' - labelled with
hexachlorofluorescein (HEX).
```

A pool of randomly mutagenized barley grains was prepared, followed by preparation of an ordered library as described in international patent application PCT/EP2017/065516 in WS1, WS2 and WS3 on p. 66-69 as well as in Examples 1 to 7. The barley cultivar used for preparing said randomly mutagenized library was barley of cv. Paustian.

Determining Whether a Library Sample Contains Mutated Grains

The next step was to determine whether the library contained the desired mutated grains. The screening was performed essentially as described in international patent application PCT/EP2017/065516 in WS3 and in Examples 3 to 7 of with the following specifics:

The screening was performed on a total of 376 sub pools (designated GLP #1 to GLP #376), together representing approximately 120,000 mutated barley plants.

One 5-µL gDNA sample derived from each sub-pool (designated GT #1-GT #376) was prepared. gDNA samples GT #1-GT #94 were added to individualwells of a microtiter plate, each well also containing 17 µl of the PCR reaction mixture and mixed thoroughly by pipetting up and down.

The microtiter plate for PCR was loaded onto the QX200 Droplet Reader (Bio-Rad) for droplet analysis. The data obtained was analysed using the software QuantaSoft (version v1.7, Bio-Rad). The threshold was determined using the 2-D plot, set at 3700 and 2500 for amplification for Channel 1 and Channel 2 amplitude, respectively. Comparison of the individual values for fractional abundance showed that gDNA (GT #64) provided higher signals than any other sample with respect to mutant detection. The fractional abundance of gDNA (GT #64) was 0.062% compared to 0.012%, the latter representing the average fractional abundance of all of the 94 tested gDNA samples.

Finding Individual Grain(s) Characterized by a Mutation of Interest

Individual barley grains carrying the gene mutation were identified essentially as described in international patent application PCT/EP2017/065516 in WS4 (p. 69-72) and in Examples 8 to 15, including the following consecutively ordered specifics:

1. Based on the analysis of gDNA derived from GT #1-GT #94 with the HvHRT-specific ddPCR assay, it was considered highly likely that the 4500 grains of GLP #64 [corresponding to positive sample gDNA (GT #64)], would comprise one or more grains with the gene mutation of interest.

2. FGLP #64 was established by sequentially removing 96×12 grain samples from GLP #64. Each 12-grain aliquot was placed on a piece of weighing paper, and then consecutively fixed with a pair of forceps, at the same time using an engraving machine (Marathon-3, Saeyang Microtech) equipped with a 1.6-mm drill to drill a small, 2-3 mm deep hole into the endosperm. The rotating movement moved flour from the endosperm onto the top of the grain and the surrounding weighing paper. The 12-grain drilled samples were placed in separate 2-mL wells of a microtiter plate, yielding the secondary sub-pool of drilled barley grains PDGLP #64. The 96 flour samples, each with flour derived from 12 drilled barley grains, were transferred to separate wells of a 1.5-mL microtitre plate (PFGLP #64) keeping a sample numbering system matching that of the drilled grains.

3. Next, PFGLP #64 was subjected to extraction of gDNA using a semi-automated DNA extraction procedure as detailed in the instructions of the NucleoSpin 96 Plant II kit (Macherey-Nagel). Accordingly, each well of the microtitre plate contained gDNA from flour of 12 grains.

4. gDNA derived from PFGLP #64 was analysed as described above. The data was analysed using the software QuantaSoft (version v1.7, Bio-Rad). The threshold was determined using the 2-D plot and set at 3700 for Channel 1 amplitude and 2500 for Channel 2 amplitude. Comparison of the individual values for fractional abundance showed that one well of PFGLP #64 contained a mutant grain. Well C04 showed a fractional abundance of 3.92% indicating the presence of a heterozygous mutant PDGLP #64.

5. All 12 grains from well C04 of PDGLP #64 were germinated. Leaf material from all 12 plantlets was harvested and subjected to DNA extraction using REDExtract (Sigma Aldrich). The gDNA derived from leaf samples was analysed as described above. The data was analysed using the software QuantaSoft (version v1.7, Bio-Rad). The threshold was determined using the 2-D plot and set at 3700 for Channel 1 amplitude and 2500 for Channel 2 amplitude. One plantlet derived from well C04 of PDGLP #64 showed a fractional abundance of 45%, confirming the presence of a heterozygous mutant. Seeds from said plant were propagated and the progeny was crossed to obtain homozygous plants. The homozygous plants were propagated to increase the material. The plants homozygous for the mutation were designated HENZ-2.

Accordingly, the HENZ-2 barley plants contains a G-A mutation of the nucleotide 1293 of the HvHRT coding sequence of SEQ ID NO:1. HENZ-2 thus carries a mutant HvHRT gene encoding mutant HvHRT protein comprising a W431stop mutation of SEQ ID NO:2.

Example 2B

Barley mutant HENZ-2a were obtained essentially as described in Example 2A, except that the barley cultivar used for preparing the randomly mutagenized library was barley of cv. Planet. The same primers and probes were used.

HENZ-2a also contains a G→A mutation of the nucleotide 1293 of the HvHRT coding sequence of SEQ ID NO:1. HENZ-2a thus also carries a mutant HvHRT gene encoding mutant HvHRT protein comprising a W431stop mutation of SEQ ID NO:2.

Thus, whereas HENZ-2 can be considered to have cv. Paustian background, HENZ-2a can be considered to have cv. Planet background.

Example 3A

HENZ-2 barley mutant plants as well as control homozygous barley plants were propagated in the field. The control homozygous plants were obtained from the crosses of the heterozygous mutant described in Example 2A, and the control homozygous plants comprise wild type HvHRT gene encoding HvHRT of SEQ ID NO: 2. Accordingly, the control homozygous plants are believed to be identical to HENZ-2 except that they do not carry the mutation of the HvHRT gene.

The HENZ-2 barley mutant plants as well as control homozygous barley plants were propagated in the field in New Zealand (1 plot) and in Fuhnen (5 individual plots). 3.6 times the TKW were sown in according the standard procedure per 10 m². The plots were treated with 150 kg nitrogen per hectare and fungicide treatments were conducted in according to standard farming procedures. In New Zealand each plot was approx. 2 m², whereas on Fuhnen each plot was approx. 7.5 m². The plots were cultivated in repetitions and HENZ-2 and control were cultivated close to each other. HENZ-2 and control were grown in plots of the same size for comparison. The yield was determined by harvesting barley plants at maturation and determining the weight of the kernels per plot. The kernel weight of 1000 kernels (TKW) was determined by weighing a predetermined number of kernels, and calculating the weight of 1000 kernels. The starch content (Starch) and protein content (Protein) of barley kernels were determined by near-infrared analysis using a Foss Tecator, Infratec 1241 grain analyzer according to manufacturer's instructions (Foss, Denmark). The starch content and the protein content is provided as the % weight of the dry starch or protein of the total kernel dry weight. The average plant height was determined by measuring the plant height of selected plants from bottom (start of first internode, right above the roots) to the top of spike (the barley spike was held upright). The ears per m² were determined by counting the number of ears on plants from a predetermined area and calculating the number of ears per m².

The results are shown in Table 1 below:

TABLE 1

| | Yield Kg/plot | TKW g | Starch % w/w | Protein % w/w | Plant Height cm | Ears/m² |
|---|---|---|---|---|---|---|
| HENZ-2 New Zealand | 1.7 | 40.7 | 62.3 | 11.6 | ND | ND |

TABLE 1-continued

| | Yield Kg/plot | TKW g | Starch % w/w | Protein % w/w | Plant Height cm | Ears/m² |
|---|---|---|---|---|---|---|
| Control New Zealand | 1.6 | 42.6 | 62.3 | 11.6 | ND | ND |
| HENZ-2 Fuhnen | 5.6 | 53.8 | 62.6 | 11.5 | 61.8 | 1033.6 |
| Control Fuhnen | 5.4 | 53.5 | 62.3 | 11.7 | 61.3 | 1068.8 |

As the data of Table 1 shows, there is surprisingly no significant difference in yield, TKW, starch content, protein content, plant height and ears/m² between the HENZ-2 mutant and the control plants.

Example 3B

Pre-harvest sprouting is very undesired, because it leads to immediate loss of seed viability. A pre-harvest sprouting experiment was conducted to evaluate the degree of pre-harvest sprouting for barley mutant HENZ-2. As controls the pre-harvest sprouting of wild type barley of cv. Paustian and cv. Flagship was determined. Barley of cv. Flagship is known to have a high level of pre-harvest sprouting. The experiment was performed as follows. HENZ-2, Paustian and Flagship were grown on the field in individual plots close to each other. At grain maturity a subpart of each plot was harvested (harvest 1). The remaining plot areas were irrigated by spraying water over the plants for 10 min per hour for 12 hours per day for 10 days, then a subpart of each plot area was harvested (harvest 2). The remaining plot area was subjected the same irrigation regime for 10 more days and then harvested (harvest 3). The day after harvest, germination tests were initiated for all three harvests. The germination tests were performed by placing 100 kernels on a filter paper in a 9.5 cm petridish and adding either 3 ml or 5 ml water. The rate of germinated kernels were counted after 3 days incubation, and is provided as % germinated kernels. Barley varieties having a decreased rate of germination between harvest 1 and harvest 2 and 3 are considered to be subject to pre-harvest sprouting, whereas barley varieties having the same or an increased rate between harvest 1 to harvest 2 and 3 are not subject to pre-harvest sprouting. The result is shown in Table 2.

TABLE 2

| | 1. harvest | | 2. harvest | | 3. harvest | | | |
|---|---|---|---|---|---|---|---|---|
| | G.R. (%) 3 ml | G.R. (%) 5 ml | G.R. (%) 3 ml | G.R. (%) 5 ml | G.R. (%) 3 ml | G.R. (%) 5 ml | Diff* 3 ml | Diff* 5 ml |
| HENZ-2 REP1 | 72 | 79 | 98 | 98 | 98 | 98 | 21 | 16 |
| HENZ-2 REP2 | 79 | 83 | 78 | 95 | 95 | 95 | | |
| Paustian REP1 | 67 | 80 | 60 | 97 | 97 | 98 | 24 | 17 |
| Paustian REP2 | 73 | 77 | 94 | 90 | 90 | 92 | | |
| Flagship REP1 | 95 | 96 | 74 | 91 | 81 | 81 | −18 | −18 |
| Flagship REP2 | 99 | 99 | 64 | 85 | 78 | 79 | | |

G.R. indicates the germination rate in %
Diff* indicates the difference between the average germination rate of the first and the third harvest as percentage points.

Both HENZ-2 and cv. Paustian had an increase in the germination rate between the first and the third harvest, and thus none of these barley plants were subject to pre-harvest sprouting. Furthermore, there is no significant difference in the increase in germination rate observed between the first and the third harvest between HENZ-2 and cv. Paustian. In contrast, cv. Flagship had a significant decrease in germination rate and thus as expected, showed pre-harvest sprouting.

Example 3C

Grain material from HENZ-2 barley mutant plants and from barley plants cv. Paustian grown in the field under similar conditions were germinated in a standard germination test:
  Grains were sorted according to size using Pfeuffer grain sorter >grains with sizes 2.5 and 2.8 mm were used
    100 full grains were placed on 2 pieces Whatman (Grade 1, 85 mm, Cat-No. 1001-085) in 90 mm petridishes and 4 ml of aqua dest was added
    Another 100 full grains were placed on 2 pieces Whatman (Grade 1, 85 mm, Cat-No. 1001-085) in 90 mm petridishes and 8 ml of aqua dest was added (high water conditions).
  Petridishes were closed and stored in a dark box covered with a wet cloth at 20° C.
  4 ml petridishes were checked after 24 h, 48 h and 72 h, germinating grains (radicula emergence) were removed from petridish and number of germinated grain noted
  8 ml petridish were checked after 72 h, germinating grain (radicula emergence) were removed from petridish and number of germinated grain noted The results after 72 h are shown in FIG. 1. The grain from wild type and HENZ-2 germinated 99,5% in 4 ml water. This indicates that the material was not dormant. When tested for water sensitivity (8 ml water), HENZ-2 had significantly higher germination rates (80% vs. 40% wild type). This indicates that HENZ-2 performs significantly better under water and oxygen stress as seen in the malt bed or in a tank with airflow as described in Example 4.

Example 4

Figure 2:
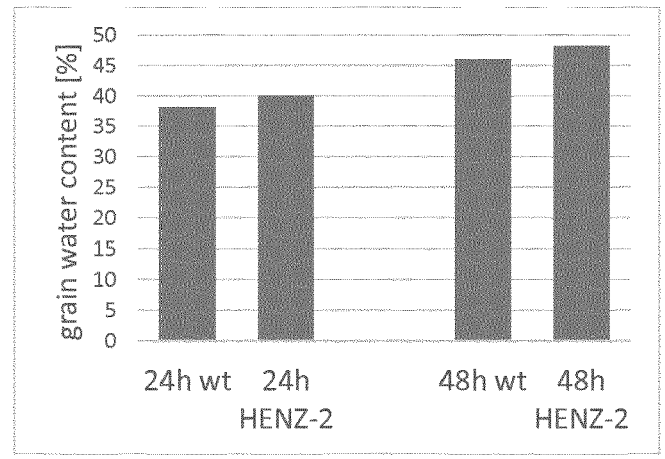
FIG. 2 shows the grain water content of grains of cv. Paustian (wt) and barley mutant HENZ-2 after incubation for 24 h and 48 h in water with an airflow of 90 L/h per kg dry weight of barley grains.

Grain material from HENZ-2 barley mutants and from barley plants cv. Paustian grown in the field under similar conditions were germinated in a tank with water essentially as described in Example 1 of international patent application PCT/EP2017/065498 with the following specifics: 200 g barley grains (dry weigth) were incubated for 48 h in a tank and covered with water containing GA 1 mM, while subjected to an air flow of 90 L/h per kg dry weight of barley grains). The grain water content was measured during germination, after 24 h and 48 h and the results are shown in FIG. 2. HENZ-2 had in both cases higher grain water content compared to wild type indicating advanced germination.

Figure 3:
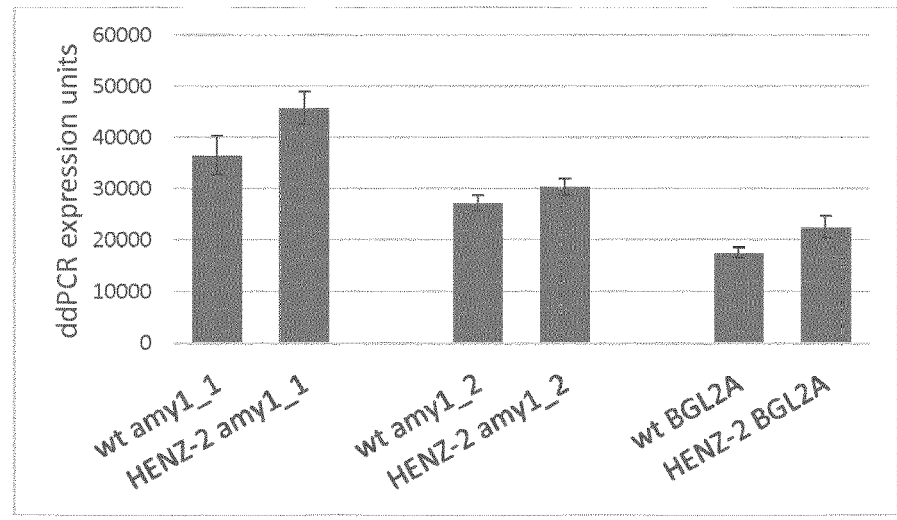
FIG. 3 shows gene expression of α-amylase mRNA encoded by α-amylase genes of the amy1_1 cluster (2 left columns), the amy1_2 cluster (2 middle columns) and of BGL2A+BGL2B mRNA (2 right columns-indicated as "BGL2A") as determined by ddPCR in cv. Paustian (wt) and barley mutant HENZ-2 after incubation for 48 h in water with an airflow of 90 L/h per kg dry weight of barley grains.

Gene expression of α-amylases (amy1_1 and amy1_2) and of β-glucanase 2A and 2B (BGL2A) were measured in the same material after 48 h using ddPCR (Biorad) with primers and probes specific for the indicated genes. The general ddPCR protocol for gene expression described in Example 20 was employed. The primers and probe used for determining BGL2A expression also amplify and detect BGL2B, and thus the combined expression of BGL2A and BGL2B was determined (indicated as "BGL2A" in FIG. 3). The results are shown in FIG. 3. HENZ-2 material showed significantly higher expression of all tested genes indicating advanced germination. The sequence of BGL2A is available under accession number HORVU7Hr1G120450.1.

The activity of α-amylases, β-amylase and limit dextrinase was measured in the same material after 24 h and after 48 h using standard Megazyme assays as follows.
Sample Preparation Prior to enzyme activity analysis the germinated grain samples were milled using a standard Foss Cyclotech mill (Foss, Denmark), equipped with a tungsten carbide grinding ring (Foss 10004463), nickel plated impeller (Foss 1000 2666) and a 1 mm outlet screen (Foss 10001989). All measurements of enzyme activity in germinated barley grains were made within 48 h after milling of the sample.
α-Amylase Activity α-Amylase activity of germinated grains was based on flour prepared as described above in the section "Sample preparation". Assays for determination of α-amylase activity utilized a Ceralpha kit from Megazyme using standard laboratory equipment.

The assays were made according to manufacturer's protocol (K-CERA 01/12), including calculation of xx-amylase activity.
β-Amylase Activity When measuring beta-amylase activity of germinated grains, flour was made as described above in the section "Sample preparation". β-Amylase activity assays followed the recommendations provided with the the Betamyl kit from Megazyme (K-BETA3).
Limit Dextrinase Activity For measurement of limit dextrinase activity in germinated grains, flour was made as described above in the section "Sample preparation". Limit dextrinase activity was determined using a Limit Dextrizyme kit T-LDZ1000 from Megazyme. Assays, including activity measurements, were done according to manufacturer's protocol (T-LDZ1000 07/9).

Figure 4A:
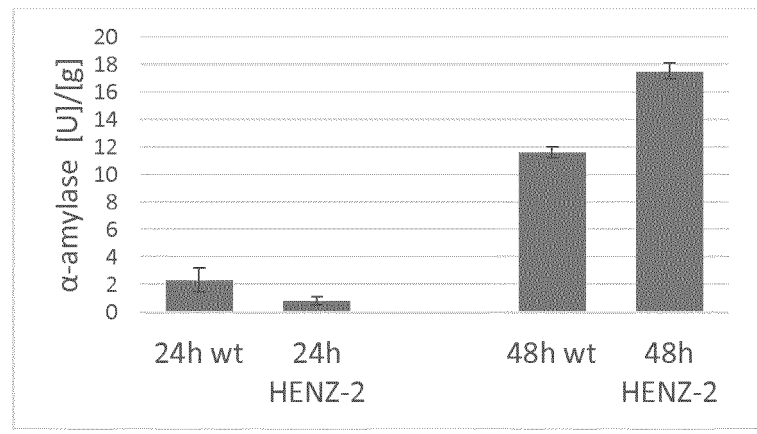
FIG. 4 shows α-amylase activity (FIG. 4A), β-amylase activity (FIG. 4B) and limit dextrinase activity (FIG. 4C) in cv. Paustian (wt) and barley mutant HENZ-2 after incubation for 24 h and 48 h in water with an airflow of 90 L/h per kg dry weight of barley grains.
Figure 4B:
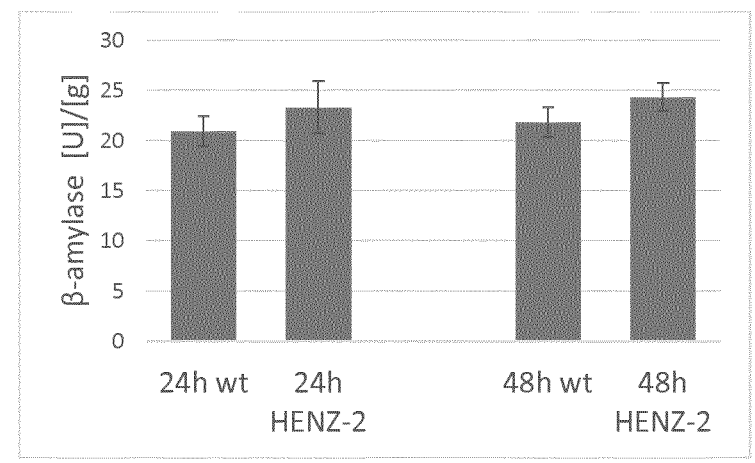
Figure 4C:
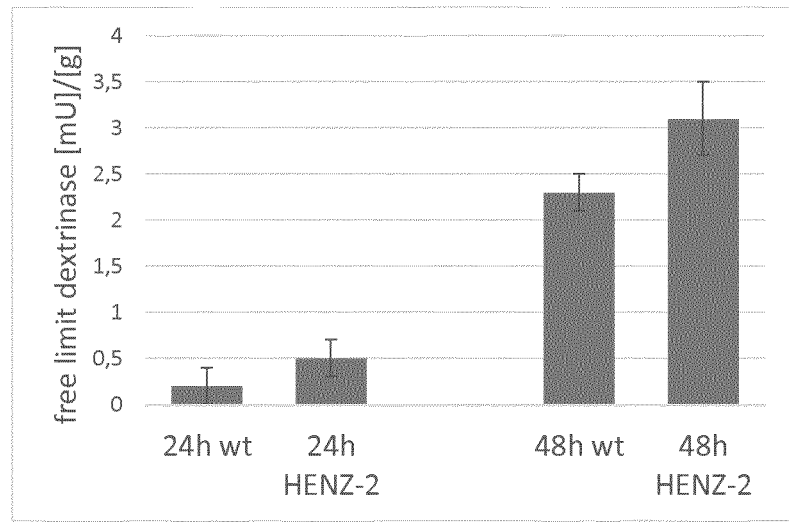

The results are shown in FIG. 4. HENZ-2 material showed significantly higher activity of all tested enzymes indicating advanced germination (exception: α-amylase 24 h sample which is generally low anyways).

Example 5

Figure 5A:
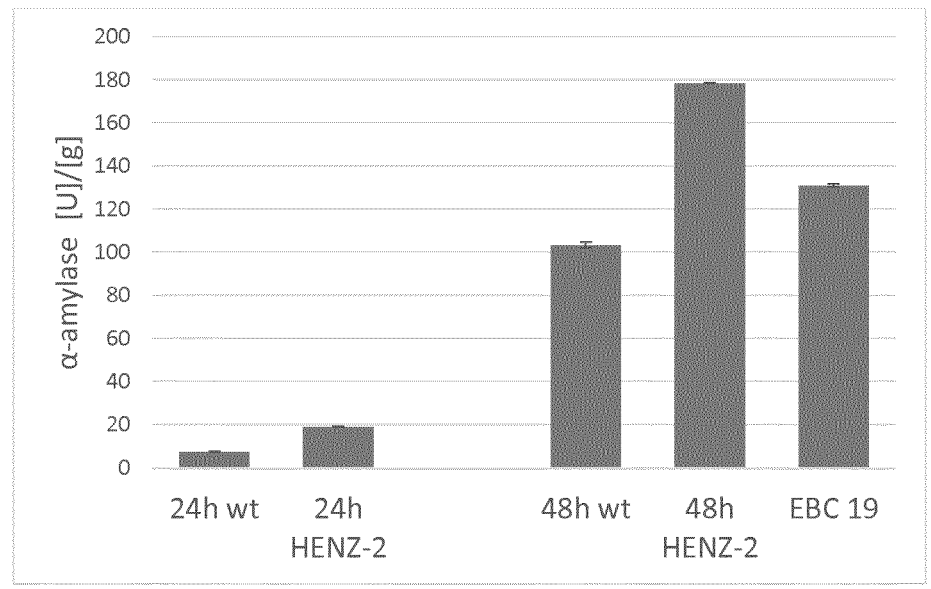
FIG. 5 shows α-amylase activity (FIG. 5A), β-amylase activity (FIG. 5B) and limit dextrinase activity (FIG. 5C) in cv. Paustian (wt) and barley mutant HENZ-2 grains, which have been peeled and incubated for 24 h in water (24 h) or for 24 h in water and 24 h in air (48 h) with an airflow of 90 L/h per kg dry weight of barley grains during said incubation.
Figure 5B:
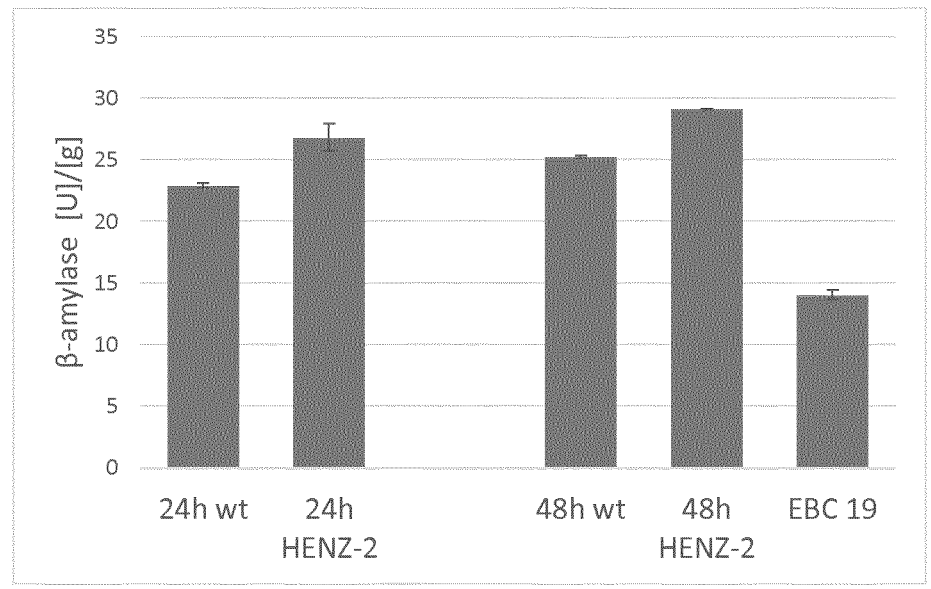
Figure 5C:
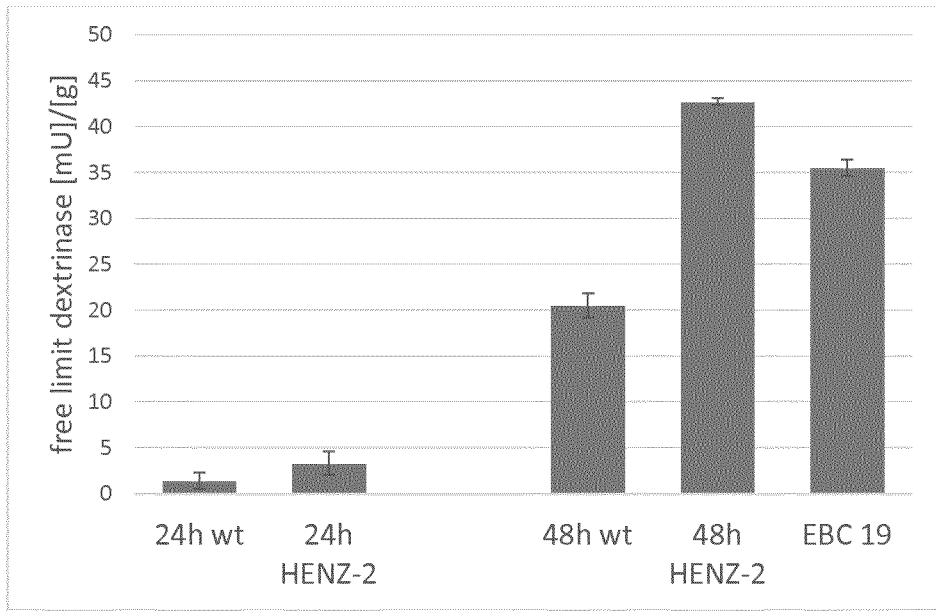

Grain material from HENZ-2 barley mutants and from barley plants cv. Paustian grown in the field under similar conditions were germinated in a tank with water essentially as described in Example 9 of international patent application PCT/EP2017/065498 with the following specifics: 200 g barley grains were subjected to peeling for 1 min as described in Example 8 of international patent application PCT/EP2017/065498. Subsequently, the peeled barley grains were transferred to a tank and covered with 500 ml water containing 0,01% $H_2O_2$, antifoam-204, $GA_3$ 1 mM and incubated for 24 h under aeration with 90 L/h air. This corresponds to 18 L air per h per 100 ml water. Excess water was drained off and the grains were incubated for 24 h with aeration with 90 L/h air). The activity of α-amylases, β-amylase and limit dextrinase was measured 24 h and after 48 h germination using standard Megazyme assays as described in Example 4. In addition the activity of these enzymes in malt prepared according to the EBC 19 standard (obtained from Institute Francais De La Brasserie Et De La Malterie (IFBM), France) was determined. The results are shown in FIG. 5. HENZ-2 material showed significantly higher activity of all tested enzymes indicating advanced germination. Activities measured for HENZ-2 even exceeded the EBC 19 standard.

Example 6

A barley mutant named HENZ-10 was identified and isolated as described below. HENZ-10 carries a nucleotide substitution in the barley gene HvHBL12 resulting in a premature STOP codon in the translation of the HBL12 protein. The amino acid exchange is tryptophan 228 to STOP (W228Stop). The mutant background is a hull-less barley variety (herein also referred to as "Hull-less 1"). Hull-less barley plants in general have higher α-amylase activity during germination compared to hulled barley varieties. The coding sequence of the mutant HvHBL12 gene is provided herein as SEQ ID NO:8, whereas the sequence of the mutant protein encoded by the mutant HvHBL12 gene is provided as SEQ ID NO:9.

The original mutant barley plant isolated was homozygous for the mutation.

Example 7A ddPCR-Based Screening for Barley Mutants with Specific Mutations in the Gene for HvHBL 12.

A barley plant carrying a specific mutation was identified using the methods described in international patent application PCT/EP2017/065516.

ddPCR Assay

A unique ddPCR assay was designed, specifically to distinguish between the mutant allele and wild-type allele of HvHBL 12 at nucleotide position 684 in the wild-type coding sequence (GenBank number NCBI: JX878491.1). Slightly different sequences for HvHBL12 are available, and the ddPCR assay was designed based on GenBank number NCBI: JX878491.1. The mutant detection probe was complementary to the coding sequence, containing an A base at nucleotide position 684 (corresponding to nucleotide 684 of SEQ ID NO:5). The reference detection probe was complementary to the coding sequence, containing a G base at nucleotide position 684. Two flanking primers were designed to amplify the genomic sequence surrounding nucleotide 684 in the coding sequence.

The following primers and probes were designed specifically for the HvHBL12 locus:

```
Target-specific forward primer (SEQ ID NO: 19):
5'- GTCGTCGTTCCCGTT - 3';

Target-specific reverse primer (SEQ ID NO: 20):
5'- CTGCAGGTCTGCTCC - 3';

Mutant-specific detection probe (SEQ ID NO: 21):
5'- ACTCGAGCTGACCGT - 3' - labelled with 6-
carboxyfluorescein (FAM);

Reference-specific detection probe (SEQ ID NO:
22):
5'- CTCGAGCTGGCCGT - 3' - labelled with
hexachlorofluorescein (HEX).
```

A pool of randomly mutagenized barley grains was prepared, followed by preparation of an ordered library as described in international patent application PCT/EP2017/065516 in WS1 and WS2 on p. 66-67 as well as in Examples 1 to 2. The barley cultivar used for preparing said randomly mutagenized library was barley of the type Hull-less 1.

Determining Whether a Library Sample Contains Mutated Grains

The next step was to determine whether the library contained the desired mutated grains. The screening was performed essentially as described in international patent application PCT/EP2017/065516 in WS3 (p. 67-69) and in Examples 3 to 7 with the following specifics:

The screening was performed with a total of 376 sub pools (designated GLP #1 to GLP #376), representing approximately 120,000 mutated barley plants.

One 5-μL gDNA sample derived from each subpool (designated GT #1-GT #376) was prepared. gDNA samples GT #283-GT #376 were added to individual wells of a microtiter plate, each well also containing 17 μl of the PCR reaction mixture and mixed thoroughly by pipetting up and down.

The microtiter plate for PCR was loaded onto the QX200 Droplet Reader (Bio-Rad) for droplet analysis. The data obtained was analysed using the software QuantaSoft (version v1.7, Bio-Rad). The threshold was determined using the 2-D plot, set at 3500 and 1500 for amplification for Channel 1 and Channel 2 amplitude, respectively. Comparison of the individual values for fractional abundance showed that gDNA (GT #291) provided higher signals than any other sample with respect to mutant detection. The fractional abundance of gDNA (GT #291) was 0.105% compared to 0.0094%, the latter representing the average fractional abundance of all of the 94 tested gDNA samples.

Finding Individual Grain(s) Characterized by a Mutation of Interest

Individual barley grains carrying a gene mutation were identified essentially as described in international patent application PCT/EP2017/065516 in WS4 (p. 69-72) and in Examples 8 to 15, including the following consecutively ordered specifics:

6. Based on the analysis of gDNA derived from GT #283-GT #376 with a HvHBL12-specific ddPCR assay, it was considered highly likely that the 4500 grains of GLP #291 [corresponding to positive sample gDNA (GT #291)], would comprise one or more grains with the gene mutation of interest.

7. FGLP #291 was established by sequentially removing 96×12 grain samples from GLP #291. Each 12-grain aliquot was placed on a piece of weighing paper, and then consecutively fixed with a pair of forceps, at the same time using an engraving machine (Marathon-3, Saeyang Microtech) equipped with a 1.6-mm drill to drill a small, 2-3 mm deep hole into the endosperm. The rotating movement moved flour from the endosperm onto the top of the grain and the surrounding weighing paper. The 12-grain drilled samples were placed in separate 2-mL wells of a microtiter plate, yielding the secondary sub-pool of drilled barley grains PDGLP #291. The 96 flour samples, each with flour derived from 12 drilled barley grains, were transferred to separate wells of a 1.5-mL microtitre plate (PFGLP #291) keeping a sample numbering system matching that of the drilled grains.

8. Next, PFGLP #291 was subjected to extraction of gDNA using a semi-automated DNA extraction procedure as detailed in the instructions of the NucleoSpin 96 Plant II kit (Macherey-Nagel). Accordingly, each well of the microtitre plate contained gDNA from flour of 12 grains.

9. gDNA derived from PFGLP #291 was analysed as described above. The data was analysed using the software QuantaSoft (version v1.7, Bio-Rad). The threshold was determined using the 2-D plot and set at 4000 for Channel 1 amplitude and 1500 for Channel 2 amplitude. Three individual wells in the microtitre plate (E03, E11, G01) were identified that showed a fractional abundance of 12.5%, 4.42% and 7.3%, all indicating the presence of three individual mutants in 3 independent wells of PDGLP #291.

10. All 12 grains from well G01 of PDGLP #291 were germinated. Leaf material from all 12 plantlets was harvested and subjected to DNA extraction using REDExtract (Sigma Aldrich). The gDNA derived from leaf samples was analysed as described above. The data was analysed using the software QuantaSoft (version v1.7, Bio-Rad). The threshold was determined using the 2-D plot and set at 6000 for Channel 1 amplitude and 2000 for Channel 2 amplitude. One plantlet derived from well H01 of PDGLP #291 showed a fractional abundance of 96.9%, confirming the presence of a homozygous mutant. Said plant was propagated to increase the material. The plants homozygous for the mutation were designated HENZ-10.

Accordingly, the HENZ-10 barley plants contains a G→A mutation of the nucleotide 684 of the HvHBL12 coding sequence (SEQ ID NO:5). HENZ-10 thus comprises a HvHBL12 gene containing the coding sequence SEQ ID NO:8. HENZ-10 thus carries a mutant HvHBL12 gene encoding mutant HvHBL12 protein comprising a W228stop mutation.

Example 7B

Barley mutant HENZ-61 was obtained essentially as described in Example 7A, except the barley cultivar used for preparing the randomly mutagenized library was barley of cv. Planet. The same primers and probes were used.

HENZ-61 also comprises a HvHBL12 gene containing the coding sequence SEQ ID NO: 8. HENZ-61 thus also carries a mutant HvHBL12 gene encoding mutant HvHBL 12 protein comprising a W228stop mutation.

Thus, whereas HENZ-10 can be considered to have Hull-less 1 background, HENZ-61 can be considered to have cv. Planet background.

Example 8A

Figure 10:
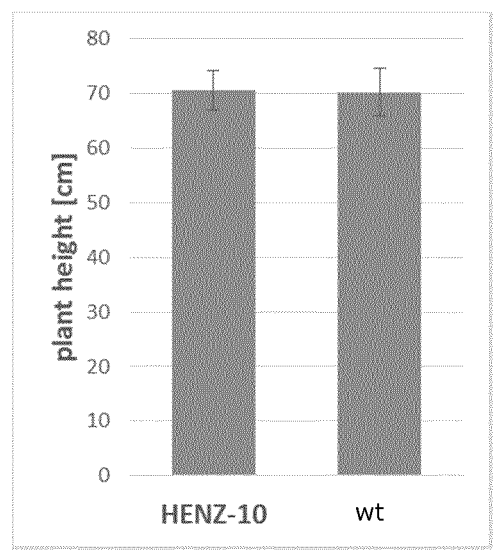
FIG. 10 shows the plant height of Hull-less 1 (wt) and barley mutant HENZ-10 after cultivation in the field under similar conditions.

HENZ-10 barley mutant plants and Hull-less 1 barley plants were cultivated in plots in the field under similar conditions. Various agronomic features were determined including average plant height. The HENZ-10 barley mutant plants appeared healthy on visual inspection. The average plant height was determined by measuring the plant height of selected plants per plot in five individual field plots from bottom (start of first internode, right above the roots) to the top of spike (the barley spike was held upright). The results are shown in FIG. 10. Interestingly, no difference in plant height was observed between the HENZ barley mutant plants and the parent Hull-less 1 barley plants.

HENZ-10 barley mutant plants as well as Hull-less 1 barley plants were propagated in the field in New Zealand (1 plot) and in Fuhnen (5 individual plots). Propagation, plot sizes etc. were essentially as described above in Example 3A. The yield, the kernel weight of 1000 kernels (TKW), the starch content (Starch) (as % dry starch of total kernel dry weight), the protein content (Protein) (as % dry protein of total kernel dry weigth), the plant height and the ears per m$^2$ were determined as described in Example 3A above.

TABLE 3

| | Yield Kg/plot | TKW g | Starch % w/w | Protein % w/w | Plant Height cm | Ears/m$^2$ |
|---|---|---|---|---|---|---|
| HENZ-10 New Zealand | 1.9 | 42.2 | 65.1 | 12.1 | ND | ND |
| Hull-less 1 New Zealand | 1.8 | 43.3 | 65.8 | 11.4 | ND | ND |
| HENZ-10 Fuhnen | 4.8 | 46.3 | 62.8 | 12.9 | 70.6 | 995.2 |
| Hull-less 1 Fuhnen | 5.2 | 48.2 | 63.9 | 12.1 | 70.2 | 1030.4 |

As the data of Table 1 shows, there is surprisingly no significant difference in yield, TKW, starch content, protein and plant height between the HENZ-10 mutant and the control plants.

Example 8B

HENZ-61 barley mutant plants as well as wild type barley plants of cv. Planet were propagated in the field in individual, but near-by plots. The yield, the kernel weight of 1000 kernels (TKW), the starch content (Starch), the protein content (protein), the plant height and the ears per m$^2$ are determined as described in Example 3A above. HENZ-61 barley mutant plants are expected to have yield, kernel weight of 1000 kernels (TKW), starch content (Starch), protein content (protein), plant height and/or ears per m$^2$ similar to cv. Planet.

Example 9

Grain material from HENZ-10 barley mutant plants and from the Hull-less 1 barley plants grown in the field under similar conditions were germinated in a standard germination test in petridishes as follows:
  Grains were sorted according to size using Pfeuffer grain sorter >grains with sizes 2.5 and 2.8 mm were used
  100 full grains were placed on 2 pieces Whatman (Grade 1, 85 mm, Cat-No. 1001-085) in 90 mm petridishes and 4 ml of aqua dest was added
  Another 100 full grains were placed on 2 pieces Whatman (Grade 1, 85 mm, Cat-No. 1001-085) in 90 mm petridishes and 8 ml of aqua dest was added.
  Petridishes were closed and stored in a dark box covered with a wet cloth at 20° C.
  4 ml petridishes were checked after 24 h, 48 h and 72 h, germinating grains (radicula emergence) were removed from petridish and number of germinated grain noted
  8 ml petridish were checked after 72 h, germinating grain (radicula emergence) were removed from petridish and number of germinated grain noted.

Figure 6:
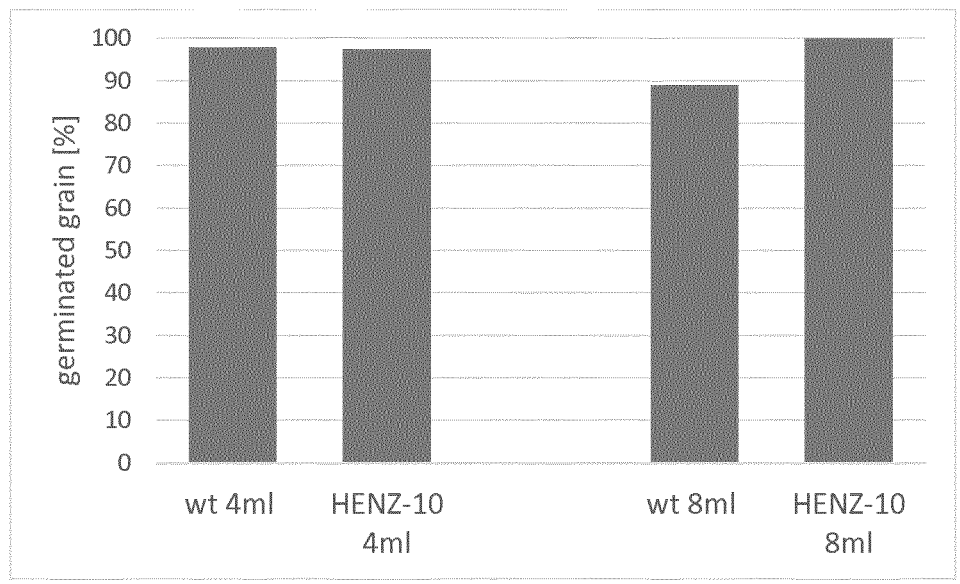
FIG. 6 shows % germinated grains of cv. Hull-less 1 (wt) and barley mutant HENZ-10 after standard germination test in the presence of either 4 ml (left columns) or 8 ml (right columns) of water.

The results after 72 h are shown in FIG. 6. The grain from wild type Hull-less 1 and HENZ-10 germinated to 98 and 97,5%, respectively, in 4 ml water. This indicates that the material was not dormant. When tested for water sensitivity (8 ml water), HENZ-10 had significantly higher germination rates (100% vs. 89% wild type). This indicates that HENZ-10 performs better under water and oxygen stress-conditions that can be found in the malt bed or in a tank with airflow as described in Example 4.

Example 10

Figure 7:
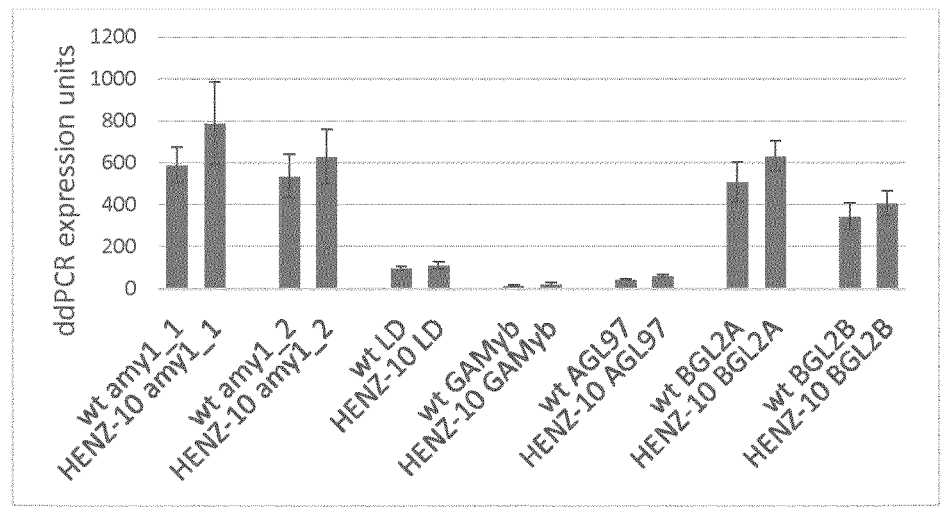
FIG. 7 shows gene expression of α-amylase mRNA encoded by α-amylase genes of the amy1_1 cluster, the amy1_2 cluster, limit dextrinase mRNA (LD), AGL97 mRNA, BGL2A mRNA and BGL2B mRNA as determined by ddPCR in cv. Hull-less 1 (wt) and barley mutant HENZ-10 after 48 h incubation in water.

Grain material from HENZ-10 barley mutants and from Hull-less 1 barley plants grown in the field under similar conditions were germinated in an Erlenmeyer flask filled with water on a shaker for 48 h at room temperature. Gene expressions of α-amylases (amy1_1 and amy1_2), limit dextrinase (LD), α-glucosidase 97 (AGL97) and of β-glucanase 2A and 2B (BGL2A and BGL2B) were measured after 48 h using the ddPCR using primers and probes specific for the indicated genes. The results are shown in FIG. 7. The sequence of BGL2B us available under HORVU1Hr1G057680.1. HENZ-10 material showed increased expression of all tested genes indicating advanced germination compared to its Hull-less 1 wild type parent. It should be noted that in Hull-less 1 barley, the endosperm modification starts earlier compared to many hulled wild type barley cultivars as e.g. indicated by an early, high α-amylase activity. It is thus notable, that HENZ-10 showed increased expression of all tested genes compared to Hull-less 1. Thus, despite Hull-less 1 already having early, high α-amylase, HENZ-10 never-the-less has an even higher α-amylase activity.

Example 11

Figure 8:
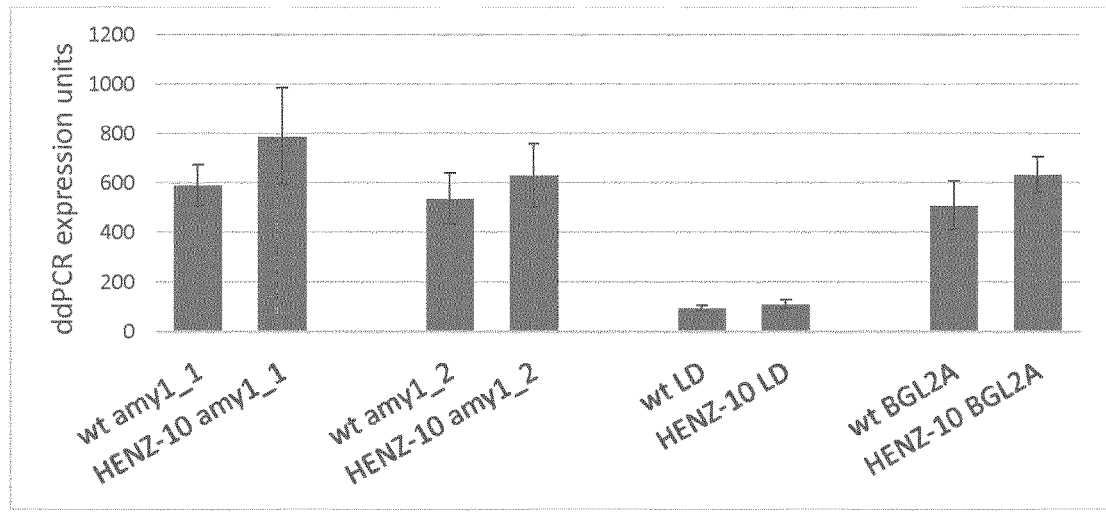
FIG. 8 shows gene expression of α-amylase mRNA encoded by α-amylase genes of the amy1_1 cluster, the amy1_2 cluster, limit dextrinase mRNA (LD) and of BGL2A mRNA in cv. Hull-less 1 (wt) and barley mutant HENZ-10 after incubation in water with an airflow of 90 L/h per kg dry weight of barley grains as determined by ddPCR.

Grain material from HENZ-10 barley mutants and from Hull-less 1 barley plants grown in the field under similar conditions were germinated in a tank with water essentially as described in Example 1 of international patent application PCT/EP2017/065498 with the following specifics: 200 g barley grains (dry weigth) were incubated for 48 h in a tank and covered with water containing GA 1 mM, while subjected to an air flow of 90 L/h, Gene expression of α-amylases (amy1_1 and amy1_2), limit dextrinase (LD) and of β-glucanase 2A (BGL2A) was measured after 48 h by ddPCR using primers and probes specific for the indicated genes. The general ddPCR protocol for gene expression described in Example 20 was employed. The results are shown in FIG. 8. HENZ-10 material showed significantly higher expression of all tested genes indicating advanced germination compared to wild type Hull-less 1 barley.

Figure 9A:
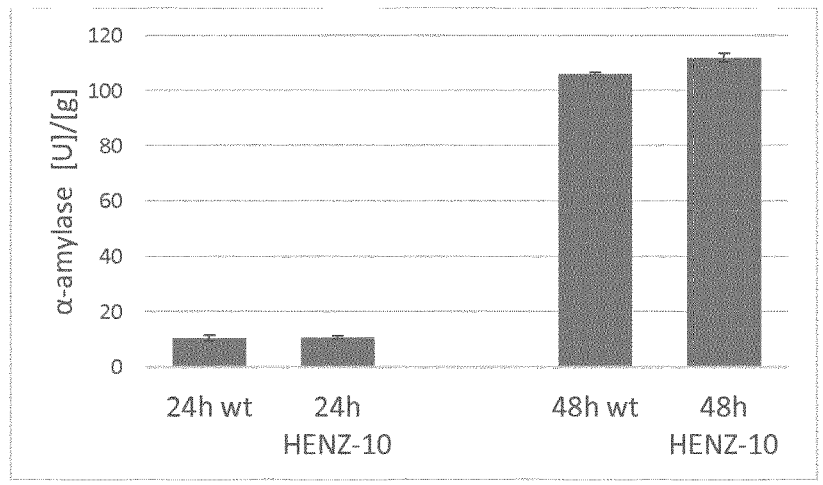
FIG. 9 shows α-amylase activity (FIG. 9A), β-amylase activity (FIG. 9B) and limit dextrinase activity (FIG. 9C) in Hull-less 1 (wt) and barley mutant HENZ-10 after incubation for 24 h and 48 h in water with an airflow of 90 L/h per kg dry weight of barley grains.
Figure 9B:
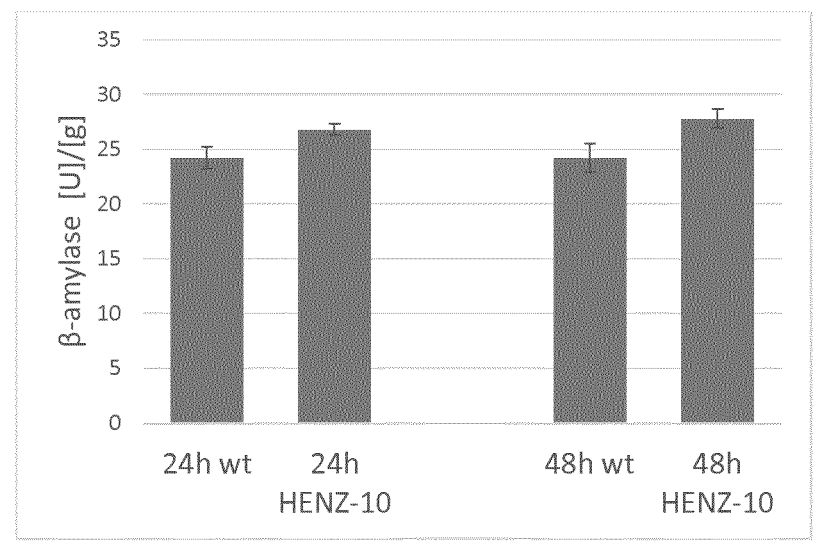
Figure 9C:
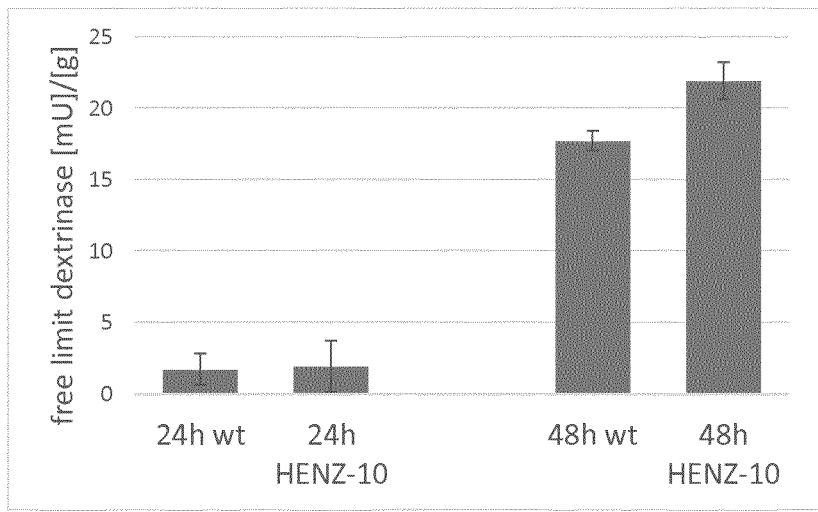

The activities of α-amylases, β-amylase and limit dextrinase were measured in the same material after 24 h and after 48 h using standard Megazyme assays as described in Example 4. The results are shown in FIG. 9. HENZ-10 material showed higher activity of all tested enzymes indicating advanced germination.

Example 12A

A barley plant named HENZ-50 was identified and isolated essentially as described in Example 2A above. HENZ-50 carries a nucleotide substitution in the barley gene WKRY38 resulting in a gene containing a premature STOP in the coding sequence. Thus, HENZ-50 carries a G→A mutation of nucleotide 600 of the coding sequence of HVWRKY38 (SEQ ID NO:10). The coding sequence of WRKY38 from barley cv.

Ingrid is provided herein as SEQ ID NO:10. Two different wild type polypeptide sequences WRKY38 from barley are provided as SEQ ID NO: 11 and SEQ ID NO: 12. The HENZ-50 barley plant carries a point mutation causing a premature STOP (W200Stop) in the barley gene HvWRKY38. The mutation is positioned at the beginning of the WKRY motif signature sequence WRKYGQK (aa 200-206 of SEQ ID NO: 11 or 12). The mutant HvWRKY38 gene of HENZ-50 encodes a mutant HvWRKY38 protein with the sequence SEQ ID NO:14.

The HENZ-50 barley mutant plant was identified in a barley cv. Planet M2 mutant population prepared by random mutagenesis essentially as described in Example 2A. The HENZ-50 was identified and isolated essentially as described in Example 2A herein above except that the following primers and probes were used for the ddPCR assay:

```
Target-specific Forward Primer
                                        (SEQ ID NO: 23)
5'-CTCAGCCTGGTGGTG-3'

Target-specific Reverse Primer
                                        (SEQ ID NO: 24)
5'-TGTCCTTGGTCACCTTC-3'

Mutant-specific detection Probe
                                        (SEQ ID NO: 25)
5'-CCAATGACGCAAGTACG-3' - labelled with FAM Reference specific detection Probe
                                        (SEQ ID NO: 26)
5'-TACCAATGGCGCAAGTA-3' labelled with HEX.
```

Example 12B

Barley mutant HENZ-50 and wildtype barley of cv. Planet are grown in the greenhouse in Denmark under similar conditions. 100 grains of each are germinated in 250 ml Erlenmeyer flasks filled with 100 ml deionized water, sealed with parafilm, and placed on a shaker 250 rpm. During germination, grains are constantly submerged in H₂O. No air is supplied apart from air in the flask.

The activity of α-amylase is measured after 72 h from the start of germination (i.e. from the time the grains were submerged in water) using the standard Megazyme assay as described in Example 4.

HENZ-50 is expected to have significantly higher α-amylase activity compared to cv. Planet.

Example 13A

A barley plant named HENZ-43 was identified and isolated essentially as described in Example 2A above. HENZ-43 carries a nucleotide substitution in the promoter of barley α-amylase gene of the amy1_1 cluster. The mutation results in a mutation of the tandem repeat W-box resulting in a non-standard tandem repeat W-box of the following sequence: TGACGGTCGTATTGATC (SEQ ID NO:35). In other words, in HENZ-43 the wild type TTGACC sequence of an amy1_1 gene was modified to TTGATC. FIG. 11A shows an alignment between partial sequences of various wild type α-amylase promoters and a partial sequence of the promoter of barley α-amylase gene of the amy1_1 cluster of the HENZ-43 mutant.

The HENZ-43 barley mutant plant was identified and isolated essentially as described in Example 2A except that the barley cultivar used for preparing the randomly mutagenized library was barley of cv. Planet and except that the following primers and probes were used for the ddPCR assay:

```
Target specific Forward Primer
                                        (SEQ ID NO: 27)
5'-AAACAGAGGTTGAGGATAAC-3'

Target specific Reverse Primer
                                        (SEQ ID NO: 28)
5'-GCCTTCGCCTTCCAT-3'
```

-continued

```
Mutant specific detection Probe
                                         (SEQ ID NO: 29)
5'-AGGCACCGATCAATACG-3'- labelled with FAM Reference specific detection Probe
                                         (SEQ ID NO: 30)
5'-AAGGCACCGGTCAATAC- 3' - labelled with HEX.
```

Example 13B

HENZ-43 barley mutant plants as well as wild type barley plants of cv. Planet are propagated in the field in individual, but near-by plots. The yield, the kernel weight of 1000 kernels (TKW), the starch content (Starch), the protein content (protein), the plant height and the ears per $m^2$ are determined as described in Example 3A above.

HENZ-43 barley mutant plants are expected to have yield, kernel weight of 1000 kernels (TKW), starch content (Starch), protein content (protein), plant height and/or ears per $m^2$ similar to cv. Planet.

Example 14

Two barley plants named HENZ-53 and HENZ-54 were identified and isolated essentially as described in Example 2A above.

HENZ-53 carries a G→A mutation of nucleotide 510 of the coding sequence of HvHRT (SEQ ID NO:1). HENZ-53 thus carries a mutant HvHRT gene encoding mutant HvHRT protein comprising a W170Stop mutation.

The HENZ-53 barley mutant plant was identified and isolated essentially as described in Example 2A herein above except that the barley cultivar used for preparing said randomly mutagenized library was barley of the type Planet and except that the following primers and probes were used for the ddPCR assay:

```
Target specific Forward Primer
                                         (SEQ ID NO: 73)
5'- GTCAGCTACTGGGAGTATT-3'

Target specific Reverse Primer
                                         (SEQ ID NO: 74)
5'- TCTTCGCGACGACAC-3'

Mutant specific detection Probe
                                         (SEQ ID NO: 75)
5'- TGCATGAAATAAACTGCAGA-3'- labelled with FAM ™

Reference specific detection Probe
                                         (SEQ ID NO: 76)
5'- TGCATGGAATAAACTGCAG- 3' - labelled with HEX ™.
```

HENZ-54 carries a G→A mutation of nucleotide 1113 of the coding sequence of HVHRT (SEQ ID NO:1). HENZ-54 thus carries a mutant HvHRT gene encoding mutant HvHRT protein comprising a W371Stop mutation.

The HENZ-54 barley mutant plant was identified and isolated essentially as described in Example 2A herein above except that the barley cultivar used for preparing said randomly mutagenized library was barley of the type Planet and except that the following primers and probes were used for the ddPCR assay:

```
Target specific Forward Primer
                                         (SEQ ID NO: 77)
5'- TGCTAATCCAAGCAAACG-3'
```

-continued

```
Target specific Reverse Primer
                                         (SEQ ID NO: 78)
5'- TTTGTGGACAGATTTTTGGA-3'

Mutant specific detection Probe
                                         (SEQ ID NO: 79)
5'-AGCCTGACAAACCAGTG-3'- labelled with FAM ™

Reference specific detection Probe
                                         (SEQ ID NO: 80)
5'- AAGCCTGGCAAACCAG- 3' - labelled with HEX ™
```

Example 15

Barley mutant HENZ-2, wild type barley of cv. Paustian, barley mutant HENZ-10 and wild type barley Hull-less 1 barley were grown in the field in New Zealand under similar conditions. 100 grains from each barley were germinated in 250 ml Erlenmeyer flasks filled with 100 ml deionized water, sealed with parafilm, placed on a shaker 250 rpm. During germination, grains were constantly submerged in $H_2O$. Air was led through the water with an air flow of 9 L/h per 100 ml water. Grains were incubated in water under aeration for 48 h or 72 h.

The activity of α-amylase was measured after 48 h and 72 h from the start of germination (i.e. from the time the grains were submerged in water) using the standard Megazyme assay as described in Example 4.

Figure 13A:
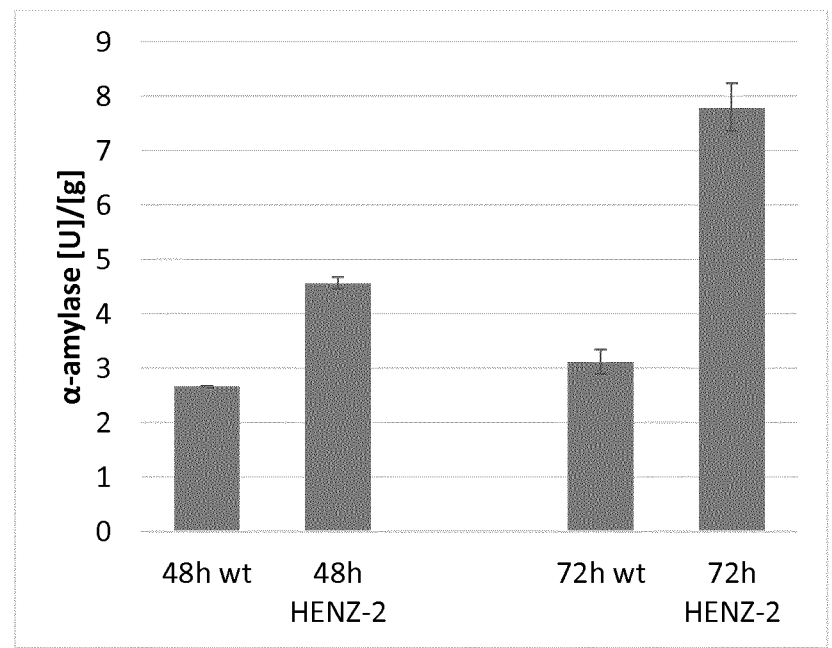
Figure 13B:
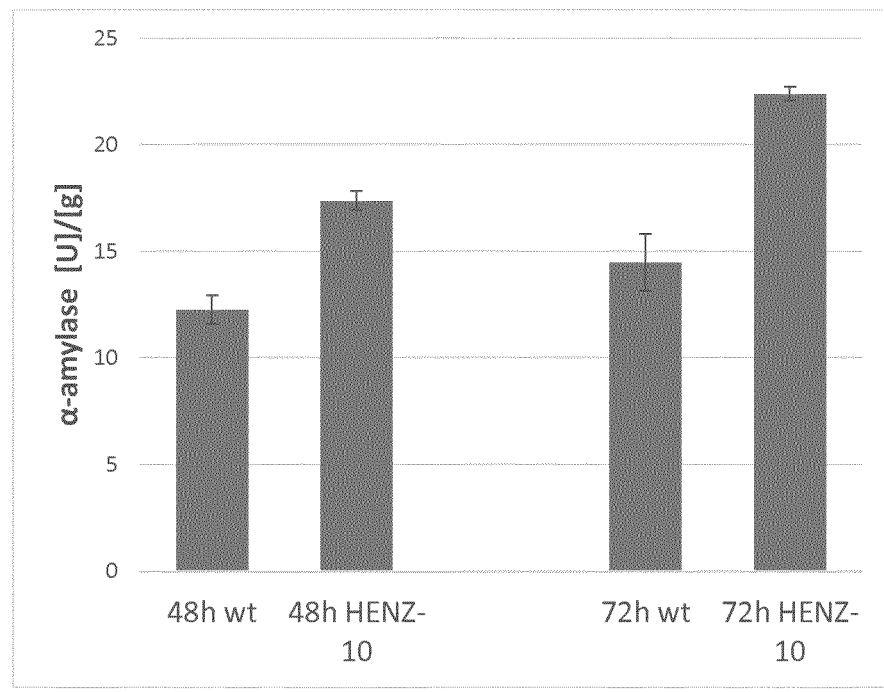
FIG. 13B shows α-amylase activity of barley mutant HENZ-10 and barley wild type Hull-less 1 (wt).

The results are shown in FIGS. 13A and 13B. FIG. 13A shows the α-amylase activity of HENZ-2 and cv. Paustian (wt). FIG. 13B shows the α-amylase activity of HENZ-10 and Hull-less 1 barley (wt). Both HENZ-2 and HENZ-10 has increased α-amylase activity compared to the respective wild type controls.

Example 16

Barley mutant HENZ-10 and wild type barley Hull-less 1 were grown in the field in New Zealand under similar conditions. 100 grains of each barley were germinated in 250 ml Erlenmeyer flasks filled with 100 ml deionized water, sealed with parafilm, placed on a shaker 250 rpm. During germination, grains were constantly submerged in $H_2O$. No air was supplied apart from air in the flask.

The activity of α-amylase was measured after 24 h, 48 h and 72 h from the start of germination (i.e. from the time the grains were submerged in water) using the standard Megazyme assay as described in Example 4.

Figure 14:
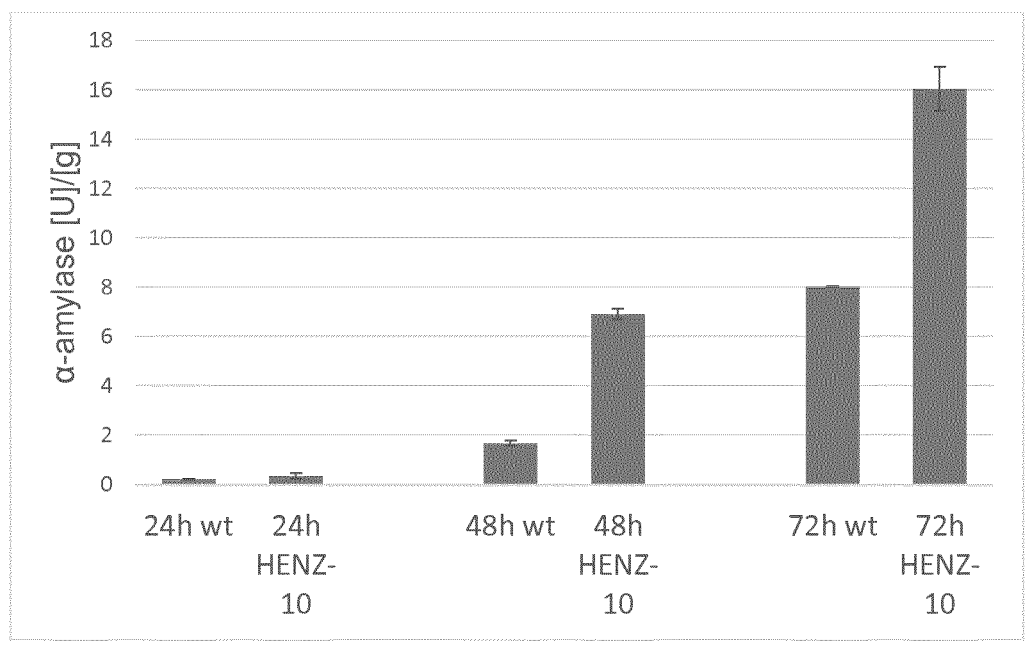
FIG. 14 shows α-amylase activity in barley grains germinating under submersion in water without airflow at 24 h, 48 h and 72 h after start of germination in barley mutant HENZ-10 and barley wild type Hull-less 1 (wt).

The results are shown in FIG. 14. FIG. 14 shows the α-amylase activity of HENZ-10 and Hull-less 1 barley (wt). HENZ-10 has significantly increased α-amylase activity, in particular after 72 h.

Example 17

Barley mutant HENZ-2a, barley mutant HENZ-54, barley mutant HENZ-43 and wildtype barley of cv. Planet were grown in the greenhouse in Denmark under similar conditions. 100 grains of each barley were germinated in 250 ml Erlenmeyer flasks filled with 100 ml deionized water, sealed with parafilm, placed on a shaker 250 rpm. During germination, grains were constantly submerged in $H_2O$. No air was supplied apart from air in the flask.

The activity of α-amylase was measured after 72 h from the start of germination (i.e. from the time the grains were submerged in water) using the standard Megazyme assay as described in Example 4.

Figure 15:
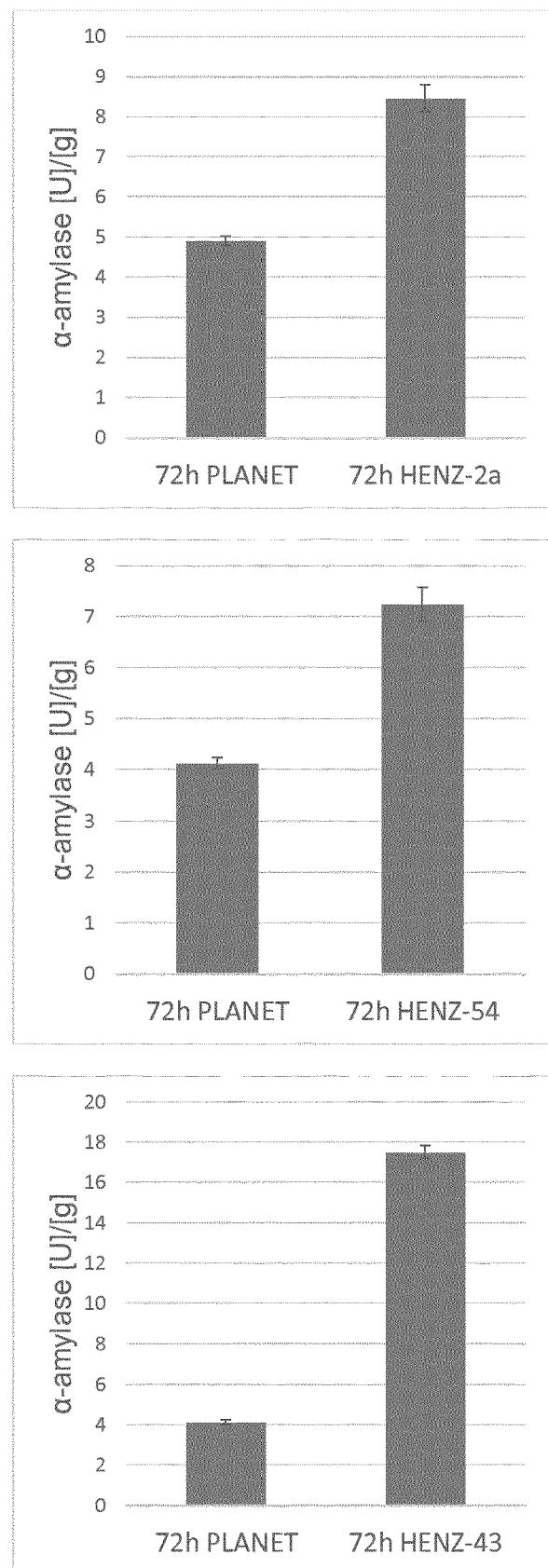
FIG. 15 shows α-amylase activity in barley grains germinating under submersion in water without airflow 72 h after start of germination.

The results are shown in FIG. 15, showing α-amylase activity of HENZ-2a in the upper panel, HENZ-54 in the middle panel and HENZ-43 in the bottom panel. HENZ-2a, HENZ-54 and HENZ-43 all have significantly increased α-amylase activity.

Example 18

Grains were obtained from HENZ-2 mutant barley and from the control homozygous barley plants described in Example 3A grown under similar conditions.

50 grains per line were imbibed for 24 hours in conical flask at 20° C. (reaching water content ~40%). Imbibed grains were transferred to a petri dish (2 ml $H_2O$) and allowed to germinate. Samples were collected at 0, 12, 24 and 48 hours following imbibition, i.e. from the time grains were transferred to the petri dish. Three biological replicates per time point were prepared in individual petri dishes. cDNA was synthesized from 300 ng total RNA and subsequently diluted 10×. Three technical cDNA replicates per sample were prepared (so total 9 replicates per line per treatment).

Expression of mRNA from the amy1_1, amy1_2 and amy2 genes was determined by ddPCR using the following primers and probes. The general ddPCR protocol for gene expression described in Example 20 was employed. All assays were designed in the 3' end of the cDNA sequence in question.

| Target | Forward primer 5'-3' | Reverse primer 5'-3' | Probe 5'-3' |
|---|---|---|---|
| amy-1 | GACTGGGGCCTGAAG (SEQ ID NO: 81) | GTGCCGGGTCCTGAC (SEQ ID NO: 82) | AGATCGATCGCCTGGTGTC (SEQ ID NO: 83) |
| amy1-2 | AGATCGATCGTCTGGTG (SEQ ID NO: 84) | TCCATGATCTGCAGCTTG (SEQ ID NO: 85) | TCAATCAGGACCCGACAGG (SEQ ID NO: 86) |
| amy2 | CGAGCTCAAGGAGTGG (SEQ ID NO: 87) | CGTCGATGTACACCTTG (SEQ ID NO: 88) | AAGAGCGACCTCGGCTTC (SEQ ID NO: 89) |

Figure 16A:
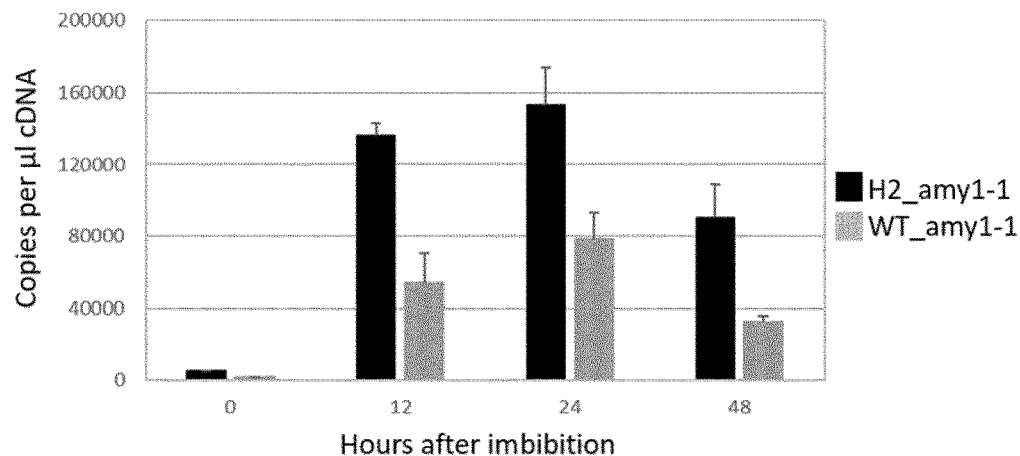
FIG. 16 shows gene expression of α-amylase mRNA encoded by α-amylase genes of the amy1_1 cluster (FIG. 16A), the amy1_2 gene (FIG. 16B), and the amy2 cluster (FIG. 16C) as determined by RT ddPCR in germinating grains of barley mutant HENZ-2 and control homozygous barley plants (WT) at 0, 12 h, 24 h and 48 h after start of germination.
Figure 16B:
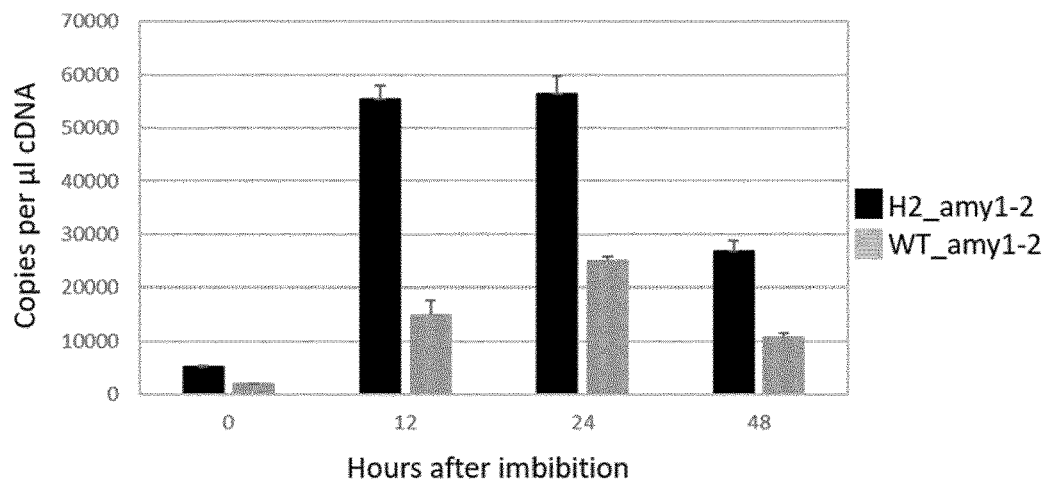
Figure 16C:
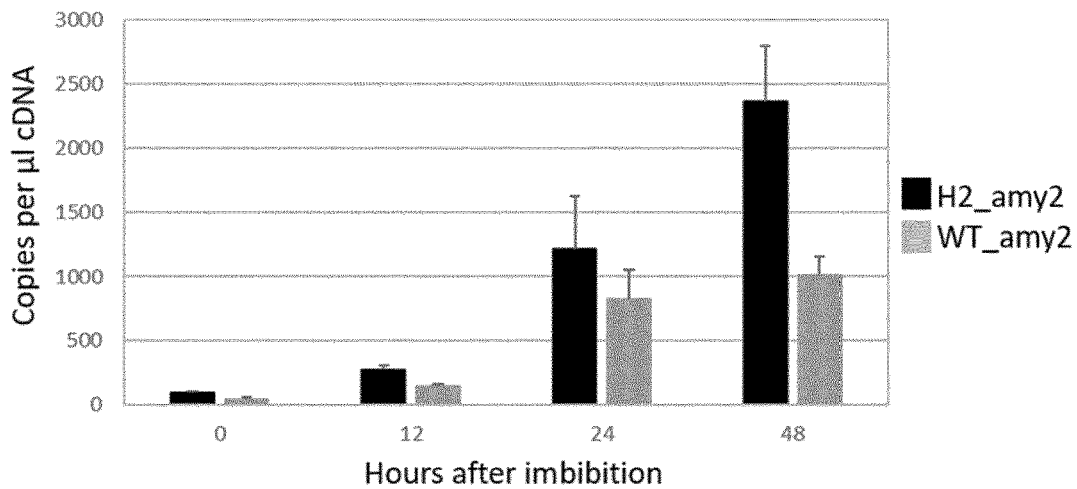
Figure 18:
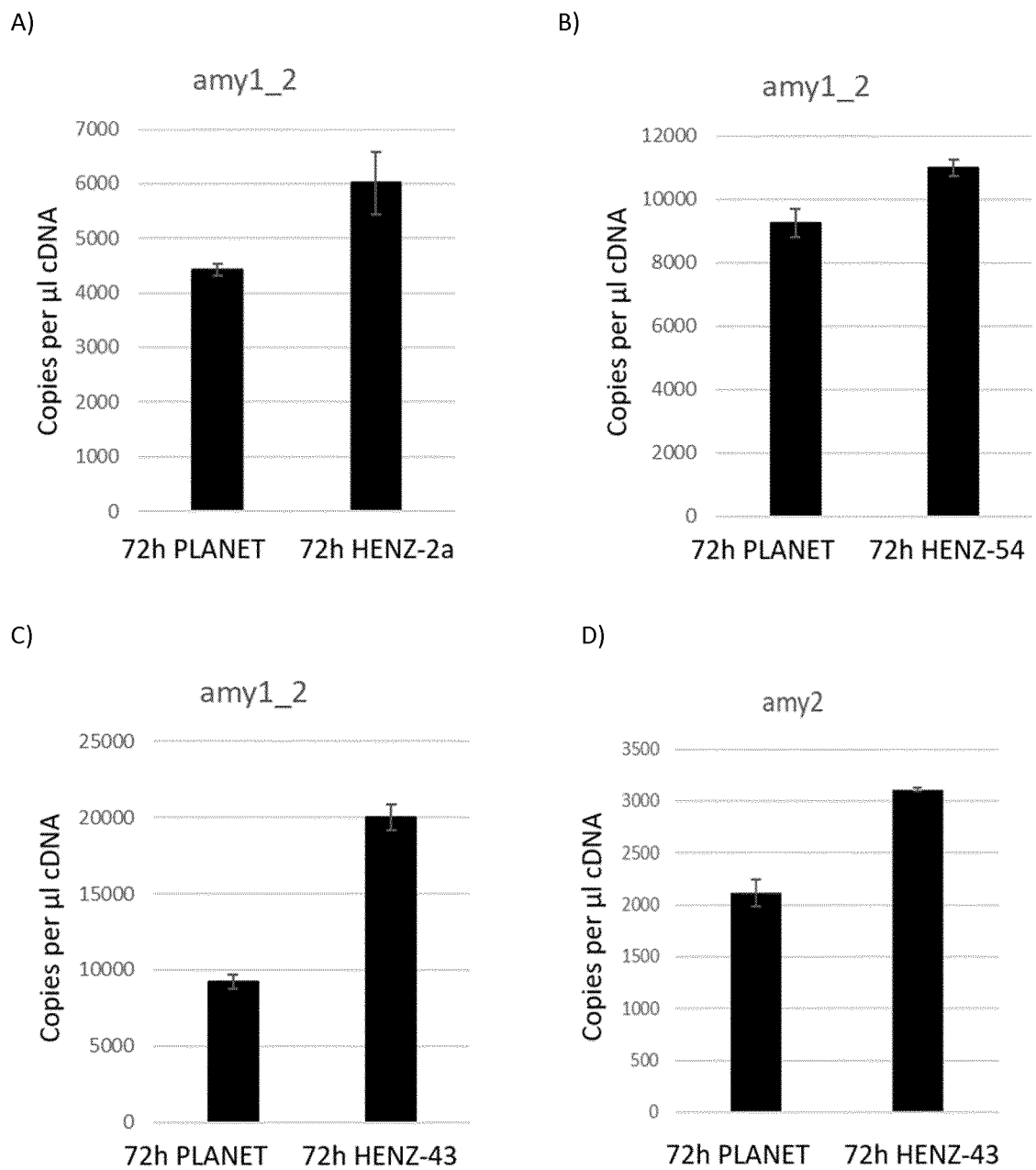
FIG. 18 shows gene expression after 72 h germination of α-amylase mRNA encoded by α-amylase genes of the amy1_2 gene (FIGS. 18A, 18B and 18C) and the amy2 cluster FIG. 18D) as determined by RT ddPCR in germinating grains of barley mutant HENZ-2a and wild type barley of cv Planet (FIG. 18A), of barley mutant HENZ-54 and wild type barley of cv Planet (FIG. 18B) and of barley mutant HENZ-43 and wild type barley of cv Planet (FIGS. 18C and 18D).
Figure 19:
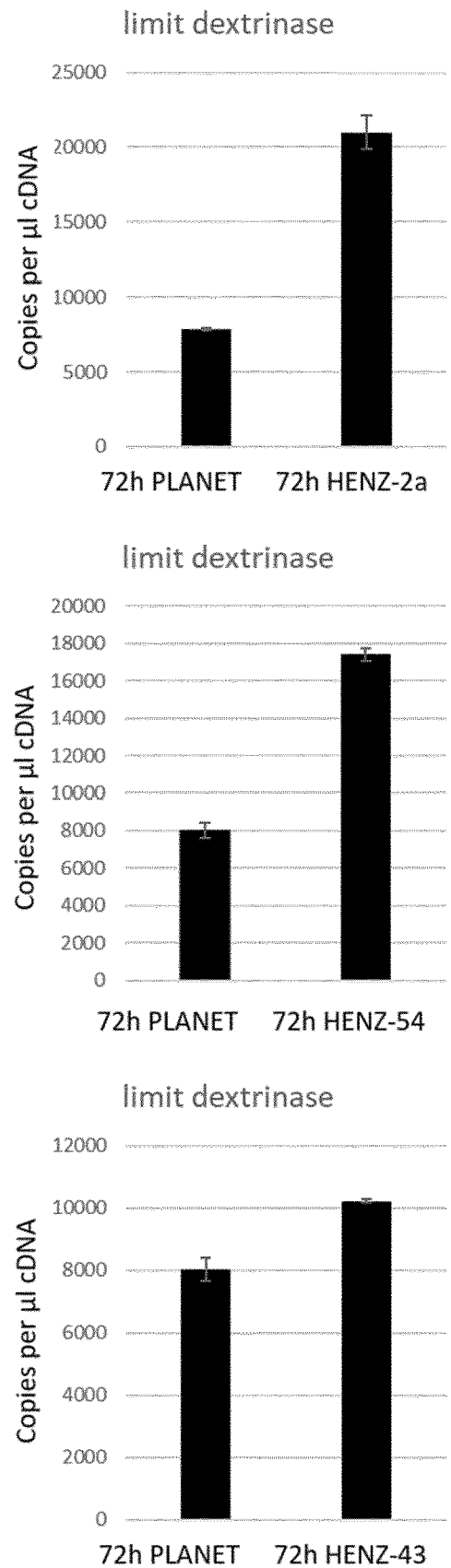
FIG. 19 shows expression after 72 h of limit dextrinase mRNA as determined by RT ddPCR in germinating grains of barley mutant HENZ-2a and wild type barley of cv Planet (upper panel), of barley mutant HENZ-54 and wild type barley of cv Planet (middle panel) and of barley mutant HENZ-43 and wild type barley of cv Planet (lower panel).

The results are shown in FIG. 16. The control is designated "WT" in the figure. HENZ-2 had increased transcript levels of all amy genes analyzed compared to the control. Amy1 expression was seemingly affected earlier than amy2 expression.

Example 19

Grain material from barley mutant HENZ-2a, barley mutant HENZ-54, barley mutant HENZ-43 and wild type barley of cv. Planet grown in the greenhouse in Denmark under similar conditions was used. 100 grains were germinated in 250 ml Erlenmeyer flasks filled with 100 ml $H_2O$, sealed with parafilm, placed on a shaker 250 rpm. During germination, grains were constantly submerged in $H_2O$. No air was supplied apart from air in the flask.

Gene expression of α-amylases (amy1_1, amy1_2 and amy2), limit dextrinase (LD) and expression of both β-glucanase 2A and 2B (together denoted "bg/2") was measured after 72 h by ddPCR using the primers and probes indicated below. Both β-glucanase 2A and 2B can be amplified and detected using the same primers and probes.

| Target | Forward primer 5'-3' | Reverse primer 5'-3' | Probe 5'-3' |
|---|---|---|---|
| amy1-1 | GACTGGGGCCTGAAG (SEQ ID NO: 81) | GTGCCGGGTCCTGAC (SEQ ID NO: 82) | AGATCGATCGCCTGGTGTC (SEQ ID NO: 83) |
| amy1-2 | AGATCGATCGTCTGGTG SEQ ID NO: 84) | TCCATGATCTGCAGCTTG (SEQ ID NO: 85) | TCAATCAGGACCCGACAGG (SEQ ID NO: 86) |
| amy2 | CGAGCTCAAGGAGTGG (SEQ ID NO: 87) | CGTCGATGTACACCTTG (SEQ ID NO: 88) | AAGAGCGACCTCGGCTTC (SEQ ID NO: 89) |
| Bgl2 | TACCAGAACCTGTTCGAC (SEQ ID NO: 90) | ACACCACCAGCTTCAC (SEQ ID NO: 91) | ACCGTGGACGCCTTCTAC (SEQ ID NO: 92) |
| LD | CTTCGATGGGGTTTGAAC (SEQ ID NO: 93) | CCGATTTCCTCACCAAAG (SEQ ID NO: 94) | CCTGTGCAGGTGAATTCATCA (SEQ ID NO: 95) |

The results are shown in FIGS. 17 to 20. HENZ-2a, HENZ-54 and HENZ-43 all had increased expression from amy1_1, amy1_2 and amy2, of limit dextrinase (LD) and from the bgl2 gene.

Example 20

Gene expression was determined by ddPCR using standard methods. More specifically RNA was generally extracted from lyophilized grain flour (~50 mg) using first a Trizol (Qiagen #15596026) protocol, followed by clean-up with the Aurum™ Total RNA Mini Kit (Bio-Rad #7326820). cDNA was synthesized using the iScript™ cDNA Synthesis Kit from Bio-Rad (#1708891).

For ddPCR analysis, each sample was mixed with primers, probe(s) (labelled with FAM or HEX), ddPCR reaction component, ddPCR Supermix (no dUTP) and water (Bio-Rad). The samples were mixed, before droplet generation (Bio-Rad QX200™ Automated Droplet Generator #1864101). The droplet plate is incubated on a thermal cycler.

The presence of FAM and/or HEX positive droplets is detected on the Bio-Rad QX200™ droplet reader and analysed using the Quantasoft software from Bio-Rad.

REFERENCES

1. Fiona J. Woodger, Frank Gubler, Barry J. Pogson and John V. Jacobsen, A Mak-like kinase is a repressor of GAMYB in barley aleurone, The Plant Journal (2003) 33, 707-717
2. Laura S. Green, Ellen Mosleth Faergestad3, Andrew Poole, and Peter M. Chandler, Grain Development Mutants of Barley, Plant Physiol. (1997) 114:203-212
3. Gubler, F., Kalla, R., Roberts, J. K., & Jacobsen, J. V. (1995). Gibberellin-regulated expression of a myb gene in barley aleurone cells: evidence for Myb transactivation of a high-pI alpha-amylase gene promoter. The Plant Cell, 7 (11), 1879-1891.
4. International Barley Genome Sequencing Consortium (IBSC). (2012). A physical, genetic and functional sequence assembly of the barley genome. *Nature,* 491 (7426). 711-716.
5. Jia, Q., Zhang, X. Q., Westcott, S., Broughton, S., Cakir, M., Yang, J., . . . & Li, C. (2011). Expression level of a gibberellin 20-oxidase gene is associated with multiple agronomic and quality traits in barley. Theoretical and Applied Genetics, 122 (8), 1451-1460.
6. Mascher, M., Gundlach, H., Himmelbach, A., Beier, S., Twardziok, S. O., Wicker, T., . . . & Bayer, M. (2017). A chromosome conformation capture ordered sequence of the barley genome. Nature, 544 (7651), 427-433.Nakata M, Fukamatsu Y, Miyashita T, Hakata M, Kimura R, Nakata Y, Kuroda M, Yamaguchi T and Yamakawa H (2017) High Temperature-Induced Expression of Rice_-Amylases in Developing Endosperm Produces Chalky Grains. Front. Plant Sci. 8:2089. doi: 10.3389/fpls.2017.02089
7. Raventós, D., Skriver, K., Schlein, M., Karnahl, K., Rogers, S. W., Rogers, J. C., & Mundy, J. (1998). HRT, a novel zinc finger, transcriptional repressor from barley. Journal of Biological Chemistry, 273 (36), 23313-23320.Schwarz et al., 2004, J. Am. Soc. Brew. Chem. 62 (4): 147-154
8. Son, O., Hur, Y. S., Kim, Y. K., Lee, H. J., Kim, S., Kim, M. R., . . . & Park, J. (2010). ATHB12, an ABA-inducible homeodomain-leucine zipper (HD-Zip) protein of *Arabidopsis*, negatively regulates the growth of the inflorescence stem by decreasing the expression of a gibberellin 20-oxidase gene. Plant and *Cell Physiology.* 51 (9), 1537-1547.
9. Valdès. A. E., Övernäs, E., Johansson, H., Rada-Iglesias, A., & Engström, P. (2012). The homeodomain-leucine zipper (HD-Zip) class I transcription factors ATHB7 and ATHB12 modulate abscisic acid signalling by regulating protein phosphatase 2C and abscisic acid receptor gene activities. *Plant molecular biology,* 80 (4-5), 405-418.
10. Zou et al. (2008) Interactions of Two Transcriptional Repressors and Two Transcriptional activators in Modulating Gibberellin Signaling in Aleurone Cells, Plant Physiology,, Vol. 148, pp. 176-186

The invention claimed is:

1. A barley plant or a part thereof, wherein said barley plant carries a mutation in the HvHRT gene resulting in a mutant HvHRT gene encoding a mutant HvHRT protein comprising the amino acid sequence of SEQ ID NO: 2 modified by a W431 stop mutation or a W371 stop mutation, and wherein said part of the barley plant is a kernel, embryo, germinated kernel, leaf, stem, root, flower, milled barley plant, or milled barley kernel.

2. The barley plant according to claim 1, wherein the said barley plant comprises a mutant HvHRT gene comprising a premature stop codon in codon 431 or codon 371 of SEQ ID NO: 1.

3. The barley plant according to claim 1, wherein the barley plant comprises a mutant HvHRT gene comprising a G→A mutation of the nucleotide 1293 of the HvHRT coding sequence of SEQ ID NO:1.

4. The barley plant according to claim 1, wherein the barley plant has an α-amylase activity of at least 100 U/g, such as at least 110 U/g 48 h after initiation of germination, provided that said barley plant is either hull-less or at least part of the hull has been removed prior to initiation of germination.

5. The barley plant according to claim 1, wherein the barley plant has a limit dextrinase of at least 20 mU/g 48 h after initiation of germination, provided that said barley plant is either hull-less or at least part of the hull has been removed prior to initiation of said germination.

6. The barley plant according to claim 1, wherein the barley plant comprises a mutation in one or more additional genes:
    a) a loss of function mutation in the gene encoding LOX-1 resulting in a total loss of functional LOX-1;
    b) a loss of function mutation in the gene encoding LOX-2 resulting in a total loss of functional LOX-2;
    c) a loss of function mutation in the gene encoding MMT resulting in a total loss of functional MMT; and/or
    d) a loss of function mutation in the gene encoding CslF6, wherein said mutant gene encodes mutant CslF6 protein with reduced CslF6 activity.

7. A plant product comprising or prepared from the barley plant according to claim 1, wherein said plant product is selected from the group consisting of barley flour, green malt and kiln dried malt; wherein the plant product comprises the mutant HvHRT gene.

8. The plant product according to claim 7, wherein the plant product is milled green malt or milled kiln dried malt; wherein the plant product comprises the mutant HvHRT gene.

9. A method of producing an aqueous extract, said method comprising the steps of:
    a) providing grains of a barley plant according to claim 1;
    b) subjecting the barley grains to a step of germination thereby obtaining germinated grains, wherein said step of germination comprises incubating said grains in an aqueous solution until the grains have a water content of at least 30%, wherein at least 2 L O2 per kg dry weight barley grains is passed through said aqueous solution per hour;
    c) finely dividing said germinated grains, while said germinated grains have a water content of at least 20%, with the proviso that said barley grains do not have a water content below 20 at any time between steps b) and c); and
    d) preparing an aqueous extract of said finely divided germinated grains, thereby producing an aqueous extract of the barley.

10. A method for producing a beverage, said method comprising the steps of:
    (i) preparing an aqueous extract by the method according to claim 9; and
    (ii) processing said extract into a beverage.

11. A method for producing a beverage, said method comprising the steps of:
    i) preparing an aqueous extract from kernels and/or malt of a barley plant according to claim 1, and
    ii) processing said extract into a beverage.

* * * * *